(12) United States Patent (10) Patent No.: US 7,734,476 B2
Wildman et al. (45) Date of Patent: Jun. 8, 2010

(54) UNIVERSAL COMMUNICATIONS, MONITORING, TRACKING, AND CONTROL SYSTEM FOR A HEALTHCARE FACILITY

(75) Inventors: Timothy D. Wildman, Metamora, IN (US); Carl W. Riley, Milan, IN (US); Craig A. McNeely, Columbus, IN (US); Thomas M. Fleck, Batesville, IN (US); Dennis J. Gallant, Harrison, OH (US); Keith A. Huster, Sunman, IN (US)

(73) Assignee: Hill-Rom Services, Inc., Wilmington, DE (US)

( * ) Notice: Subject to any disclaimer, the term of this patent is extended or adjusted under 35 U.S.C. 154(b) by 1790 days.

(21) Appl. No.: 10/673,980

(22) Filed: Sep. 29, 2003

(65) Prior Publication Data

US 2004/0193449 A1 Sep. 30, 2004

Related U.S. Application Data

(60) Provisional application No. 60/414,057, filed on Sep. 27, 2002.

(51) Int. Cl.
G06Q 10/00 (2006.01)
G06Q 50/00 (2006.01)
(52) U.S. Cl. ......................................................... 705/2
(58) Field of Classification Search ...................... 705/2, 705/4, 29; 235/385, 462.46; 340/10.1, 286.07, 340/539.16; 709/223
See application file for complete search history.

(56) References Cited

U.S. PATENT DOCUMENTS 2,976,419 A 3/1961 Menke et al.
3,439,320 A 4/1969 Ward
3,478,344 A 11/1969 Schwitzgebel et al.

(Continued)

FOREIGN PATENT DOCUMENTS

GB 2 193 359 2/1988

(Continued)

OTHER PUBLICATIONS

Great New Product: Infrared Locator, Teleconnect, Feb. 1986.

(Continued)

*Primary Examiner*—Jerry O'Connor
*Assistant Examiner*—John A Pauls
(74) *Attorney, Agent, or Firm*—Barnes & Thornburg LLP

(57) ABSTRACT

A system for a facility including a server coupled to a database, a plurality of tags coupled to a plurality of assets, each tag being configured to transmit a tag ID that is uniquely associated in the database with data describing the asset, a plurality of first transceivers for receiving tag IDs and transmitting the tag IDs and a transceiver ID to the server, which is configured to update the database with location information for the asset to indicate that the asset is adjacent the transceiver, and a plurality of portable client devices configured to wirelessly transmit to the server a client device ID that is uniquely associated in the database with a user of the client device, whereby, in response to receipt of the client device ID, the server is configured to update the database with location information for the user to indicate a location of the user.

36 Claims, 45 Drawing Sheets

U.S. PATENT DOCUMENTS

| | | | |
|---|---|---|---|
| 3,696,384 A | 10/1972 | Lester | |
| 3,714,573 A | 1/1973 | Grossman | |
| 3,739,329 A | 6/1973 | Lester | |
| 3,805,227 A | 4/1974 | Lester | |
| 3,805,265 A | 4/1974 | Lester | |
| 3,988,724 A | 10/1976 | Anderson | |
| 4,151,407 A | 4/1979 | McBride et al. | |
| 4,216,462 A | 8/1980 | McGrath et al. | |
| 4,225,953 A | 9/1980 | Simon et al. | |
| 4,275,385 A | 6/1981 | White | |
| 4,598,275 A | 7/1986 | Ross et al. | |
| 4,601,064 A | 7/1986 | Shipley | |
| 4,649,385 A | 3/1987 | Aires et al. | |
| 4,688,026 A * | 8/1987 | Scribner et al. | 235/385 |
| 4,706,689 A | 11/1987 | Man | |
| 4,728,928 A | 3/1988 | Shipley | |
| 4,740,792 A | 4/1988 | Sagey et al. | |
| 4,837,568 A | 6/1989 | Snaper | |
| 4,843,640 A | 6/1989 | Juengel | |
| 4,885,571 A | 12/1989 | Pauley et al. | |
| 4,955,000 A | 9/1990 | Nastrom | |
| 4,967,195 A | 10/1990 | Shipley | |
| 4,979,217 A | 12/1990 | Shipley | |
| 4,981,141 A | 1/1991 | Segalowitz | |
| 4,990,892 A | 2/1991 | Guest et al. | |
| 5,012,113 A | 4/1991 | Valentine et al. | |
| 5,014,040 A | 5/1991 | Weaver et al. | |
| 5,027,314 A | 6/1991 | Linwood et al. | |
| 5,036,852 A | 8/1991 | Leishman | |
| 5,038,800 A | 8/1991 | Oba | |
| 5,051,741 A | 9/1991 | Wesby | |
| 5,062,151 A | 10/1991 | Shipley | |
| 5,119,104 A | 6/1992 | Heller | |
| 5,153,584 A | 10/1992 | Engira | |
| 5,214,421 A | 5/1993 | Vernon et al. | |
| 5,218,344 A | 6/1993 | Ricketts | |
| 5,226,090 A | 7/1993 | Kimura | |
| 5,231,991 A | 8/1993 | Nelson | |
| 5,245,314 A | 9/1993 | Kah, Jr. | |
| 5,266,944 A | 11/1993 | Carroll et al. | |
| 5,291,399 A | 3/1994 | Chaco | |
| 5,317,309 A | 5/1994 | Vercellotti et al. | |
| 5,319,191 A | 6/1994 | Crimmins | |
| 5,319,363 A | 6/1994 | Welch et al. | |
| 5,341,412 A | 8/1994 | Ramot et al. | |
| 5,351,149 A | 9/1994 | Crimmins | |
| 5,363,425 A | 11/1994 | Mufti et al. | |
| 5,374,921 A | 12/1994 | Martin et al. | |
| 5,387,993 A | 2/1995 | Heller et al. | |
| 5,390,238 A | 2/1995 | Kirk et al. | |
| 5,396,224 A | 3/1995 | Dukes et al. | |
| 5,402,469 A | 3/1995 | Hopper et al. | |
| 5,412,715 A | 5/1995 | Volpe | |
| 5,417,222 A | 5/1995 | Dempsey et al. | |
| 5,421,177 A | 6/1995 | Sieber et al. | |
| 5,426,425 A | 6/1995 | Conrad et al. | |
| 5,455,851 A | 10/1995 | Chaco et al. | |
| 5,458,123 A | 10/1995 | Unger | |
| 5,461,665 A | 10/1995 | Shur et al. | |
| 5,465,082 A | 11/1995 | Chaco | |
| 5,471,404 A | 11/1995 | Mazer | |
| 5,493,283 A | 2/1996 | Hopper et al. | |
| 5,504,477 A | 4/1996 | Whitright et al. | |
| 5,515,426 A | 5/1996 | Yacenda et al. | |
| 5,525,967 A | 6/1996 | Azizi et al. | |
| 5,534,876 A | 7/1996 | Erickson et al. | |
| 5,541,585 A | 7/1996 | Duhame et al. | |
| 5,548,637 A | 8/1996 | Heller et al. | |
| 5,561,412 A * | 10/1996 | Novak et al. | 340/286.07 |
| 5,572,195 A | 11/1996 | Heller et al. | |
| 5,572,653 A | 11/1996 | DeTemple et al. | |
| 5,576,952 A | 11/1996 | Stutman et al. | |
| 5,588,009 A | 12/1996 | Will | |
| 5,589,821 A | 12/1996 | Sallen et al. | |
| 5,590,648 A | 1/1997 | Mitchell et al. | |
| 5,594,786 A | 1/1997 | Chaco et al. | |
| 5,600,108 A | 2/1997 | Newham | |
| 5,621,384 A | 4/1997 | Crimmins et al. | |
| 5,627,524 A | 5/1997 | Fredrickson et al. | |
| 5,629,678 A | 5/1997 | Gargano et al. | |
| 5,633,742 A | 5/1997 | Shipley | |
| 5,635,907 A | 6/1997 | Bernard et al. | |
| 5,640,002 A | 6/1997 | Ruppert et al. | |
| 5,640,157 A | 6/1997 | Langeraar | |
| 5,652,570 A | 7/1997 | Lepkofker | |
| 5,682,139 A | 10/1997 | Pradeep et al. | |
| 5,682,142 A | 10/1997 | Loosmore et al. | |
| 5,686,888 A | 11/1997 | Welles, II et al. | |
| 5,689,229 A | 11/1997 | Chaco et al. | |
| 5,714,932 A | 2/1998 | Castellon et al. | |
| 5,722,599 A | 3/1998 | Fries | |
| 5,729,196 A | 3/1998 | Aljadeff et al. | |
| 5,731,757 A | 3/1998 | Layson, Jr. | |
| 5,732,711 A | 3/1998 | Fitzpatrick | |
| 5,742,233 A | 4/1998 | Hoffman et al. | |
| 5,745,037 A | 4/1998 | Guthrie et al. | |
| 5,745,272 A | 4/1998 | Shipley | |
| 5,748,084 A | 5/1998 | Isikoff | |
| 5,748,148 A | 5/1998 | Heiser et al. | |
| 5,751,246 A | 5/1998 | Hertel | |
| 5,754,125 A | 5/1998 | Pearce | |
| 5,760,687 A | 6/1998 | Cousy | |
| 5,767,788 A | 6/1998 | Ness | |
| 5,771,003 A | 6/1998 | Seymour | |
| 5,793,861 A | 8/1998 | Haigh | |
| 5,815,566 A | 9/1998 | Ramot et al. | |
| 5,818,617 A | 10/1998 | Shipley | |
| 5,822,418 A | 10/1998 | Yacenda et al. | |
| 5,822,544 A | 10/1998 | Chaco et al. | |
| 5,825,283 A | 10/1998 | Camhi | |
| 5,828,306 A | 10/1998 | Curran | |
| 5,831,533 A | 11/1998 | Kanno | |
| 5,835,907 A | 11/1998 | Newman | |
| 5,838,223 A | 11/1998 | Gallant et al. | |
| 5,838,472 A | 11/1998 | Welch et al. | |
| 5,920,287 A | 7/1999 | Belcher et al. | |
| 5,949,335 A * | 9/1999 | Maynard | 340/572.1 |
| 5,959,529 A | 9/1999 | Kail, IV | |
| 6,009,333 A | 12/1999 | Chaco | |
| 6,037,879 A | 3/2000 | Tuttle | |
| 6,040,773 A | 3/2000 | Vega et al. | |
| 6,091,332 A | 7/2000 | Eberhardt et al. | |
| 6,097,301 A | 8/2000 | Tuttle | |
| 6,100,804 A | 8/2000 | Brady et al. | |
| 6,101,390 A | 8/2000 | Jayaraman et al. | |
| 6,104,311 A | 8/2000 | Lastinger | |
| 6,114,962 A | 9/2000 | Wiklof et al. | |
| 6,118,379 A | 9/2000 | Kodukula et al. | |
| 6,121,878 A | 9/2000 | Brady et al. | |
| 6,127,917 A * | 10/2000 | Tuttle | 340/10.1 |
| 6,127,928 A | 10/2000 | Issacman et al. | |
| 6,130,612 A | 10/2000 | Castellano et al. | |
| 6,131,067 A | 10/2000 | Girerd et al. | |
| 6,133,832 A | 10/2000 | Winder et al. | |
| 6,133,837 A | 10/2000 | Riley | |
| 6,137,411 A | 10/2000 | Tyren | |
| 6,137,412 A | 10/2000 | Herzer | |
| 6,144,301 A | 11/2000 | Frieden | |
| 6,147,592 A | 11/2000 | Ulrich et al. | |
| 6,150,921 A | 11/2000 | Werb et al. | |
| 6,150,948 A | 11/2000 | Watkins | |
| 6,154,139 A | 11/2000 | Heller | |
| 6,177,861 B1 | 1/2001 | MacLellan et al. | |
| 6,204,764 B1 | 3/2001 | Maloney | |

| | | | |
|---|---|---|---|
| 6,204,765 B1 | 3/2001 | Brady et al. | |
| 6,204,813 B1 | 3/2001 | Wadell et al. | |
| 6,211,781 B1 | 4/2001 | McDonald | |
| 6,252,512 B1 | 6/2001 | Riley | |
| 6,259,355 B1 | 7/2001 | Chaco et al. | |
| 6,344,794 B1 * | 2/2002 | Ulrich et al. | 340/539.16 |
| 6,353,413 B1 | 3/2002 | White et al. | |
| 2001/0051905 A1 * | 12/2001 | Lucas | 705/29 |
| 2002/0059425 A1 * | 5/2002 | Belfiore et al. | 709/226 |
| 2002/0092912 A1 * | 7/2002 | Hamilton et al. | 235/462.46 |

FOREIGN PATENT DOCUMENTS

| | | |
|---|---|---|
| GB | 2 230 365 | 10/1990 |
| GB | 2 265 038 | 9/1993 |
| WO | WO 92/09178 | 5/1992 |

OTHER PUBLICATIONS

T.H. Ooi, "Low Cost RF Identification and Locating System," IEEE Trans. On Consumer Electronics, No. 4, Nov. 1989, pp. 831-839.

United Identifications Systems Corp., Infra-Com, 1989.

The Computer for the 21st Century, Mark Weiser, Scientific American, Sep. 1991.

The Clock With SEKURMED, 1991.

Infant Monitoring System, Sekurmed.

Keeping Track of Alzheimer and Dementia Prone Patients Just Got Easier, Security Tag Systems, Inc.

* cited by examiner

Current Patient Data Screen...

| Tag ID | Name | Versus ID (Initials) | Room Number | Condition | Primary Doctor Tag ID | Prim |
|---|---|---|---|---|---|---|
| 23963884 | Bob Null | | 6566 | Critical | 23963942 | Craig |
| 23963883 | Dave Newkirk | DN | | Stable | 15732535 | Joe |
| 23963924 | James Taylor | | 507 | Poor | 15732535 | Joe |
| 23963950 | Julie Sailor | | 110 | Fair | 23963942 | Craig |
| 23963888 | Srieker Dhana | | 303 | Stable | 23963949 | Cour |
| 23963927 | Test Patient #1 | | 501 | Critical | 23963949 | Cour |
| 23963927 | Test Patient #2 | | 502 | Stable | 15732535 | Joe |
| 23963927 | Test Patient #3 | | 503 | Critical | 15732535 | Joe |
| 23963928 | Test Patient #4 | | 504 | Stable | 23963949 | Cour |
| 23963925 | Test Patient #5 | | 505 | Fair | 23963942 | Craig |
| 23963925 | Test Patient #6 | | 506 | Fair | 23963942 | Craig |
| 23963885 | Vilal Dhana | | 302 | Stable | 15732535 | Joe |

Refresh — 527

Exit

FIG. 24

Current Personnel Data Screen...

| Tag ID | Name | Versus ID (Initials) | Category | Certifications | Qualified Skills |
|---|---|---|---|---|---|
| 10 | AA | | RN | | |
| 11 | AB | | RN | | |
| 20 | BA | | LPN | | |
| 21 | BB | | LPN | | |
| 23963927 | Bria Sailors | | Staff | None | |
| 23963926 | Brok Sailor | | Staff | None | |
| 30 | CA | | RSP | | |
| 31 | CB | | RSP | | |
| 23963949 | Court Sailor | | DR | All | Some |
| 23963942 | Craig McNeely | CM | DR | Surgeon | MD PHD |
| 40 | DA | | PHY | | |
| 41 | DB | | PHY | | |
| 50 | EA | | Staff | | |
| 51 | FA | | Visitor | | |
| 15732535 | Joe DePrisco | | DR | MD,PHD,PDQ | All |
| 23963924 | Julie Sailor | | RN | All | All |

Refresh    Exit

FIG. 26

Patient Form #2 10:46 ok

Therapy Needs:

Allergies:

Family Members:

Comments Log:

Add New Comment:

UNIVERSAL COMMUNICATIONS, MONITORING, TRACKING, AND CONTROL SYSTEM FOR A HEALTHCARE FACILITY

CROSS-REFERENCE TO RELATED PATENT APPLICATIONS

This application claims the benefit of U.S. Provisional Patent Application Ser. No. 60/414,057, filed Sep. 27, 2002 which is hereby expressly incorporated herein by reference.

TECHNICAL FIELD OF THE INVENTION

The present invention relates generally to monitoring systems for improving communications and personnel and asset management in a healthcare facility.

BACKGROUND AND SUMMARY OF THE INVENTION

Caregivers such as physicians, nurses and other staff in a hospital ward, hospital wing, or other healthcare facility generally work under high pressure, high stress and long hours. These caregivers should be highly responsive to patient needs, in non-emergency as well as emergency situations. Due to ever-increasing costs of healthcare and other economic practicalities, efficient deployment of the caregivers in a healthcare facility is desired, particularly at night when the number of caregivers is typically maintained at a minimum. Nevertheless, optimizing efficiency is of secondary importance relative to the primary objective of providing a high level of healthcare. Accordingly, it is desirable to increase the efficiency of caregivers and improve the healthcare provided to patients.

The present invention provides a wholly integrated, universal communications, tracking, monitoring and control system for a healthcare facility. The system permits direct wireless communication among personnel, wireless access to continuously updated, stored information relating to patients, personnel and other assets, covert or automatic collection of information relating to the movement and status of such patients, personnel and other assets, and control (either manually or automatically) of equipment and environmental features of the facility based on activities and/or the movement or status of patients, personnel or other assets.

Additional features and advantages of the present invention will be evident from the following description of the drawings and exemplary embodiments.

BRIEF DESCRIPTION OF THE DRAWINGS

FIGS. 20-33 are screen shots generated by asset monitoring and control software operated by a computing device of the system shown in FIGS. 1 and 2.

FIGS. 34-43 are screen shots generated by communications and asset tracking and control software operated by a client device in accordance with the principles of the present invention.

DETAILED DESCRIPTION OF EXEMPLARY EMBODIMENTS

Figure 1:
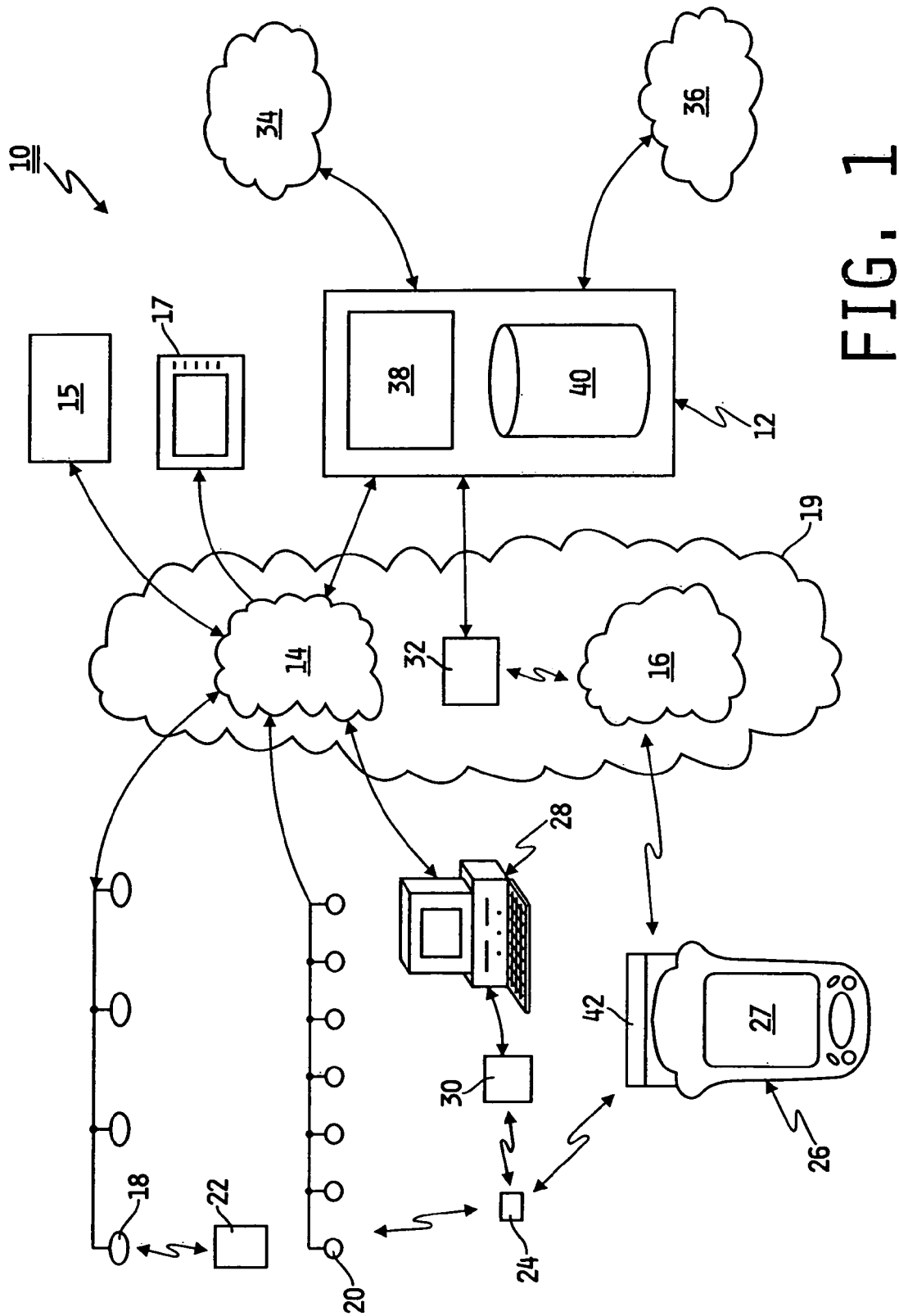
FIG. 1 is a conceptual diagram of a system according to the present invention.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the appended claims.

FIG. 1 shows components of a system according to one embodiment of the present invention. System 10 of FIG. 1 generally includes a server 12, a first network 14, a second network 16, a plurality of first transceivers 18 connected to first network 14, a plurality of second transceivers 20 connected to first network 14, a plurality of active tags 22 (only one shown), a plurality of passive tags 24 (only one shown), a plurality of client devices 26 (only one shown), a plurality of work stations 28 (only one shown), each connected to an interface 30 and to first network 14, and a plurality of routers 32 connected to second network 16 and server 12. As is also shown in FIG. 1, server 12 may further be coupled to a hospital information system network, network 34, and another communications network 36 external to the facility in which system 10 is installed, for example, the internet. Also coupled to network 14 are a plurality of other systems collectively designated 15 (as further described below) and a plurality of display devices 17 (only one shown) such as monitors, electronic white boards, etc.

Server 12 may be any of a variety of conventional computing devices such as a mainframe computer, a workstation computer, a personal computer, etc. As will be apparent to one skilled in the art, server 12 may be selected based on speed, memory capacity, and other performance characteristics necessary for providing the communications and data handling functions described herein. Server 12 is depicted as a single device having logic software 38 and a database 40, both of which are stored in a conventional storage media (not shown) coupled to server 12. It should be understood, however, that server 12 may be implemented as a plurality of separate servers connected together over a network. Also, database 40 may include multiple databases (each containing a different type or amount of information). Database 40 may further be a distributed database, having portions stored in a plurality of different locations. For simplicity, server 12 is referred to herein as a single, central server having a single database 40.

Network 14 and network 16 may be implemented as a single network (indicated in FIG. 1 as network 19) that is wired, wireless, or a combination of wired and wireless. In one embodiment of the invention, network 14 is a wired network such as a conventional wired Ethernet. Accordingly, transceivers 18, transceivers 20, workstations 28, other systems 15 and displays 17 are coupled to network 14 using conventional wire technology. In such an embodiment, network 16 is a wireless communication network such as a wireless Ethernet conforming to the 802.11(b) communications standard. As such, network 16 includes a plurality of conventional access points (not shown) positioned at various locations throughout the facility such as in patient rooms, hallways, or other locations. As is well known in the art, the spacing between such access points should be such that wireless devices in communication with network 16 will always be within range of an access point, thereby providing complete coverage of the facility or a section of the facility. Network 16 is in communication with server 12 via routers 32 which process communications between network 16 and server 12 according to principles that are well known in the art.

Transceivers 18 are of the type suitable for an equipment and/or personnel locating and tracking system. In one embodiment of the invention, transceivers 18 are of the type suitable for use with active tags 22 that periodically transmit an identification signal to receivers (not shown) in transceivers 18 using active IR, active RF, or other suitable communications technology. Transmitters (not shown) in transceivers 18 similarly transmit signals to active tags 22 using active communications technology. As is well known in the art, transceivers 18 are mounted at various locations throughout the facility such as in patient rooms, hallways, and other locations. The location of each transceiver 18 is known by server 12. Thus, when a particular transceiver 18 receives an identification signal from an active tag 22 and forwards a message to server 12 via network 14 including the identification signal, server 12 can determine that active tag 22 is within range of the particular transceiver 18. Thus, server 12 can access database 40 to determine which person or piece of equipment has been associated with the active tag 22 that transmitted the identification signal. The location of the associated person or piece of equipment may then be updated as being in proximity of the particular transceiver 18 (e.g., within a particular patient room).

Transceivers 18 and transceivers 20 are shown as two separate sets of transceivers to indicate two different types of locating technology. In one embodiment of the invention, transceivers 20 are RFID transceivers suitable for communications with RFID tags 24 using either passive or active RFID technology. A full description of suitable transceivers and RFID tags is included in co-pending U.S. patent application Ser. No. 10/154,644, entitled "A WASTE SEGREGATION COMPLIANCE SYSTEM," filed May 24, 2002, the disclosure of which is hereby expressly incorporated herein by reference. As further described herein, transceivers 20 may be mounted at various locations throughout the facility such as near or on hygiene equipment, waste disposal equipment, patient beds, door jams, care zones adjacent patient beds, family zones within patient rooms, openings in walls though which supplies are passed (as further described herein), facility shipping and receiving areas, hallways, nursing stations, and any other desired location within the facility. As is also further described herein, RFID tags 24 may be mounted to items worn or carried by people, equipment, and supplies of any type (collectively referred to herein as assets). Each RFID tag 24 is associated in database 40 with the asset to which the tag is assigned based on the unique identification signal generated by the tag. Transceivers 20 receive these identification signals from RFID tags 24, and transmit messages to server 12 via network 14 that identify RFID tags 24 within range of transceivers 20. Since the location of each transceiver 20 and the association between RFID tags 24 and the assets to which they are assigned are known (and stored in database 40), server 12 can access database 40 to determine (and/or update) the location of each asset having an RFID tag 24 as further described herein.

Additional details concerning the structure and function of suitable systems for locating and tracking assets and to support various other features of the present invention are disclosed in U.S. Pat. No. 5,561,412, U.S. Pat. No. 6,344,794, co-pending U.S. patent application Ser. No. 09/751,241, entitled "PERSONNEL AND ASSET TRACKING METHOD AND APPARATUS," filed Dec. 29, 2000, co-pending U.S. patent application Ser. No. 09/699,796, entitled "HYGIENE MONITORING SYSTEM," filed Oct. 30, 2000, and co-pending U.S. Provisional Patent Application S/No. 60/462,216, entitled "ARTICLE LOCATING AND TRACKING APPARATUS AND METHOD," filed Apr. 11, 2003, the disclosures of which are hereby incorporated by reference. Additional location and tracking systems are disclosed in U.S. Pat. Nos. 4,275,385; 4,601,064; Re. 35,035; 5,633,742; 5,745,272; 5,818,617; 5,119,104; 5,387,993; 5,548,637; 5,572,195; 5,291,399; 5,455,851; 5,465,082; 5,515,426; 5,594,786; 5,689,229; 5,822,418; 5,822,544; 5,699,038 and 5,838,223, the disclosures of which are hereby expressly incorporated herein by reference.

Client device 26 may include any of a variety of conventional portable computing and communication devices including laptops, tablet PCs, pocket PCs, mobile PCs, and PDAs. Client device 26 includes wireless functionality for communications over network 16. Accordingly, client device 26 includes a transceiver module, a microphone, and a speaker (none shown). One suitable client device 26 is a Compaq IPAQ H3600, H3700 and H3800 Series Pocket PC with a Compaq IPAQ Pocket PC Wireless Pack for 802.11x wireless (e.g., Wi-Fi) or GSM/GPRS Networks. Client device 26 further includes a display 27, and an RFID interface 42 for reading information from RFID tags 24 and writing information to RFID tags 24 as is further described below. RFID interface 42 may be any of a variety of conventional RFID read/write devices such as those available from Northern Apex of Indiana, and is coupled to client device 26 according to principles that are well known in the art. While both client device 26 and workstation 28 are described herein as including RFID interfaces 30, 42, is should be understood that bar code technology (or other suitable technology) could readily be used instead of or in addition to RFID technology.

Client device 26 may be configured as a thin client such that client device 26 obtains information as needed from server 12 via network 16, and only a minimal amount of data is actually stored in the memory (not shown) of client device 26. It should be understood, however, that client devices 26 may alternatively store information obtained by system 10 in a distributed database configuration as mentioned above. In such an embodiment, client devices 26 may share information over network 16 rather than access information stored in a central location such as database 40. It should also be understood that client devices 26 may communicate directly with one another without accessing an access point of network 16 so long as the client devices 26 are within range of one another. This communication may include text, audio and/or video content. Additionally, client device 26 may include a cellular telephone or pager to permit direct communications with systems that are external to the facility (such as cell phone networks). It is also within the scope of the invention to interface either of networks 14, 16 with a PBX to permit communications between client devices 26 using the 802.11 (b) or another wireless communication standard and conventional telephones using the Plain Old Telephone System (POTS).

Finally, client devices 26 may also include one of tags 22, 24 to permit locating and tracking of client devices 26 (in addition to any tags 22, 24 worn by the user of a client device 26). This feature could be a theft deterrent or used as a reminder for charging the battery (not shown) of client device 26. For example, if a client device tag 22, 24 is detected by an appropriate transceiver 18, 20 at an exit to the facility, software 38 of server 12 could be configured to activate an alarm, transmit a message to security personnel, or otherwise automatically respond to the potential theft. As another example, a battery charging station for client devices 26 may include an appropriate transceiver 18, 20 for detecting the presence of client devices 26. Software 38 may be configured to transmit a message to appropriate personnel to retrieve a client device 26 from its known location if the client device 26 is not detected at the battery charging station at a certain time (e.g., within one hour after the shift of the person associated with the client device 26). It should be understood that some information relating to the location of client device 26 may be obtained simply by determining the access point used by client device 26 to connect to network 16. Such information is transmitted to server 12 which, based on the known locations of the access points, can determine a general area (corresponding to the reception area of the access point) in which client device 26 is operating.

Workstations 28 may also include any suitable type of computing device having sufficient performance characteristics to function as described herein. In one embodiment of the invention, workstations 28 are PCs at essentially fixed locations throughout the facility. For example, workstations 28 may be located in an admissions area, at nurse stations throughout the facility, in administrative areas, etc. Some or all of workstations 28 may be coupled to an RFID interface 30 similar to RFID interface 42 described above. Workstations 28 may also be configured to function as thin client devices, and primarily access information from server 12 via network 14. Alternatively, workstations 28 may be configured to function in a server-like fashion, collecting information directly via an input device such as a keyboard, and from a plurality of transceivers 18, 20 in proximity to workstation 28. In such an embodiment, each workstation 28 may communicate information with server 12 and other workstations 28, while maintaining a database of information corresponding to the components of system 10 in proximity to (or otherwise associated with) workstation 28.

Figure 2:
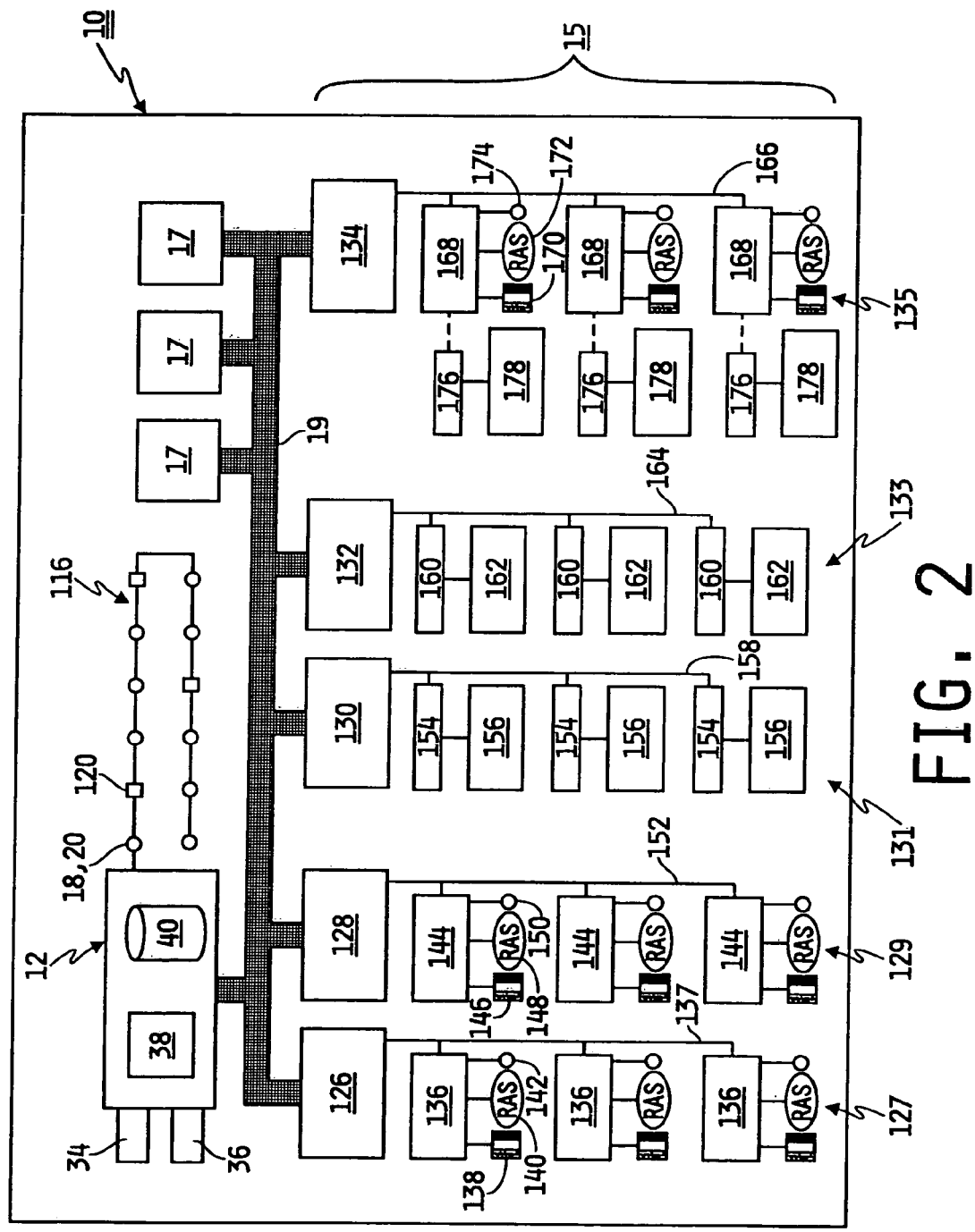
FIG. 2 is a conceptual diagram of an expanded system according to the present invention.

As should be apparent from the foregoing, other systems 15 connected to network 14 may provide additional information to server 12 or enhance the functionality of system 10. FIG. 2 depicts such an architecture of system 10. System 10 includes an enterprise server 12 that may correspond to the central server 12 described above. Enterprise server 12 is coupled to networks 34, 36 as described above. Server 12 is further coupled to a network 116 that includes transceivers 18 and/or transceivers 20 and manual data input devices 120 such as keypads, keyboards, touch screens, voice activated input devices, barcode readers, biometric recognition devices, etc. Server 12 of system 10 is coupled to a plurality of other servers (described below) and display devices 17 by network 19 described above. Display devices 17 may be monitors, electronic whiteboards, computer displays, displays of client devices 26, or any other type of device for displaying information. Network 19 may correspond to networks 14, 16 of system 10 or any other suitable local area or wide area network.

The plurality of additional servers connected to network 19 include a first nurse call server 126 of a first communications system 127, a second nurse call server 128 of a second communications system 129, a first equipment monitoring server 130 of a first monitoring system 131, a second equipment monitoring server 132 of a second equipment monitoring system 133, and a universal server 134 of a combined communications and equipment monitoring system 135. First nurse call server 126 may be a server such as that used in the COMposer® communication system available from Hill-Rom. Some details of the COMposer® communication system are disclosed in U.S. Pat. No. 5,561,412, U.S. Pat. No. 5,699,038, and U.S. Pat. No. 5,838,223, which are hereby expressly incorporated herein by reference. As explained in the COMposer® patents, first nurse call server 126 is coupled via a DXP switching network 137 to a plurality of room boards 136 located in patient rooms. Each room board 136 is coupled to an indicator light 138, a room audio station (RAS 140), and a plurality of input and output devices such as other lights, switches, and sensors (collectively referred to by the designation 142). Essentially, first nurse call server 126 controls communications among caregivers and patients and provides various status indications of certain conditions. For example, first nurse call server 126 may receive a nurse call request generated by a patient at an input device 142 such as a nurse call button. The signal may be transmitted to first nurse call server 126 via room board 136. First nurse call server 126 may then transmit a signal to a pager (not shown) carried by the appropriate caregiver. First nurse call server 126 may further cause room board 136 to change the appearance of indicator light 138 (positioned, for example, outside the patient's room) to indicate that the patient has placed a call to receive assistance from a caregiver. The caregiver may respond to the call by using an intercom system (part of first nurse call server 126) to contact the patient through RAS 140 (including a speaker, microphone and a display) located in the patient's room.

Another of the input devices 142 coupled to room board 136 is a code blue switch (not shown), activation of which results in automatic transmission by first nurse call server 126 of notification signals to appropriate caregivers, and a change in the appearance of indicator light 138 to indicate a code blue situation. Information describing any and all of the communication traffic and other functions performed by first communication system 127 controlled by first nurse call server 126 may be provided to server 12 via network 19. This information may permit system 10 to notify appropriate personnel of certain conditions or otherwise automatically respond to certain conditions as further described herein.

Second communications system 129 is similar to first communications system 127. Second communications system 129 may be the COMlinx™ communications system available from Hill-Rom and described in the COMlinx™ Enterprise Solutions User's Guide and System Configuration Guide, and the Nurse Communication Module Installation and Service Guide, all of which are hereby expressly incorporated herein by reference. System 129 includes components that are similar to those of system 127, including room controllers 144 located in patient rooms. Each room controller 144 is connected to an indicator light 146, a RAS 148, and a plurality of input and output devices collectively referred to by designation 150. Room controllers 144 are connected to second nurse call server 128 by a data and voice network 152. Second nurse call server 128 may provide similar information to server 12 as that provided by first nurse call server 126.

First equipment monitoring server 130 of first equipment monitoring system 131 is connected to a plurality of data acquisition and display devices (DADDs 154) which in turn are coupled to fetal monitoring equipment 156. Each DADD 154 is coupled to a data network 158. First equipment monitoring system 131 may be an obstetrical patient data management system such as the WatchChild system available from Hill-Rom and described in the WatchChild User's Guide and System Configuration Guide, which are hereby expressly incorporated herein by reference. First equipment monitoring server 130 may therefore provide information to server 12 via network 19 describing the output of the various fetal monitoring equipment 156.

Second equipment monitoring system 133 is simply a more generalized version of first equipment monitoring system 131. More particularly, second equipment monitoring server 132 is coupled via data network 164 to a plurality of DADDs 160 configured to receive, display, and transfer information from any of a plurality of different monitoring equipment 162 such as cardiac monitoring equipment, etc. Accordingly, second equipment monitoring server 132 may provide information to server 12 via network 19 describing the output of the various other monitoring equipment 162.

Universal server 134 of combined communications and equipment monitoring system 135 is coupled via data and voice network 166 to a plurality of room controllers 168 located in a plurality of patient rooms. Room controllers 168 are coupled to indicator lights 170, RASs 172, and a plurality of input and output devices collectively referred to by designation 174. Room controllers 168 are further coupled to one or more DADDs 176 in the room, which in turn are coupled to a plurality of other devices 178 such as monitors, beds, and other equipment in the room. Accordingly, universal server 134 receives information including communications information and equipment output and status information in the manner described above with reference to the other systems coupled to network 19. As such, universal server 134 may provide any of the above-described information to server 12 via network 19 in the manner described above. It should be noted that the connection between RASs 172 and room controllers 168 and between DADDs 176 and room controllers 168 are indicated by dotted lines to denote wireless connections. Any of the connections between the various components, however, could readily be implemented using wired or wireless technology.

Additionally, a plurality of patient point of care devices may be coupled to network 19 such as those disclosed in co-pending U.S. patent application Ser. No. 10/211,451, entitled "Point of Care Computer System," filed Aug. 2, 2002, and hereby expressly incorporated herein by reference. As described in the '451 application, such point of care devices may provide information regarding meals, entertainment uses, scheduling, and messaging that may readily by stored on database 40, and accessed by appropriate facility personnel using, for example, client devices 26 or workstations 28, for responding to patient needs, billing for goods and services, or otherwise monitoring and/or controlling a patient's use of the features provided by the point of care device.

Moreover, any combination of the above-described systems (and any number of systems of the same type) may be coupled to server 12 via network 19. It is further within the scope of the invention to couple multiple systems 10 together over a network such as network 36. In such an embodiment, a data warehouse may be provided wherein multiple facilities share information from their respective databases 40 with a central database at the data warehouse. The data warehouse may include an automatic archival function wherein certain data is saved to a permanent storage media, and a reporting feature wherein reports relating to the operations of the facilities are generated and automatically transmitted to the facilities.

Figure 3:
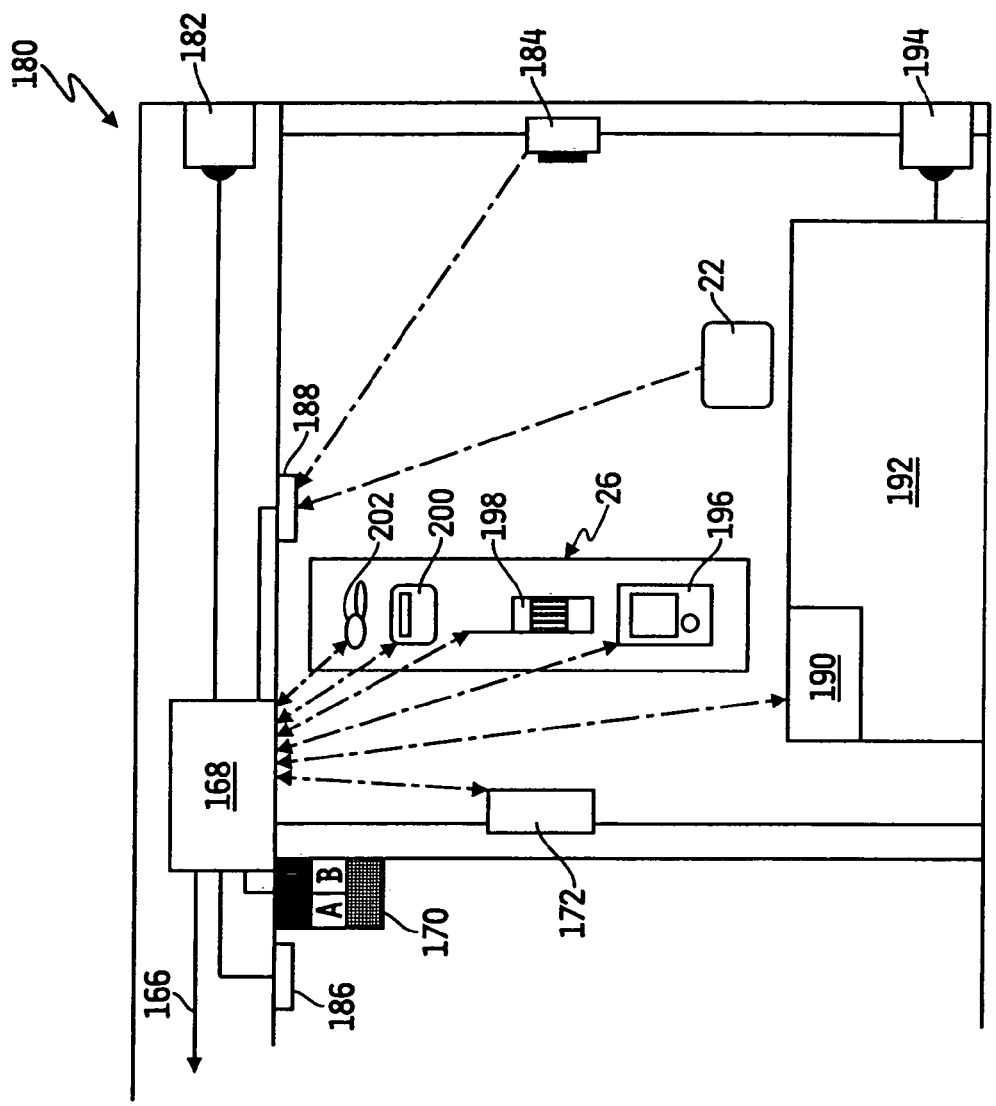
FIG. 3 is a conceptual, side elevational view of a room including a plurality of components of the system shown in FIG. 2.

FIG. 3 depicts a room 180 incorporating some of the above-described components of system 10. More specifically, room 180 depicts an example of a portion of combined communications and equipment monitoring system 135. Room 180 includes a room controller 168 powered by an AC power outlet 182 and/or a DC power back-up system (not shown). As also shown in FIG. 2, room controller 168 is coupled to a data and voice network 166, an indicator light 170, and a RAS 172. The plurality of input and output devices 174 of FIG. 2 are depicted in FIG. 3 as a wall switch 184, a first sensor 186, a second sensor 188, and a client device 26. DADD 176 and device 178 of FIG. 2 are depicted in FIG. 3 as a bed station 190 mounted to a bed 192 powered by an AC power outlet 194.

Sensors 186, 188 may be of the same technology as either of transceivers 18 or 20. Sensors 186, 188 are associated with room controller 168 because they are used to perform certain nurse call locating activities. For example, when a caregiver enters room 180 wearing active tag 22, sensor 188 receives an identification signal from active tag 22 and transmits a signal to room controller 168, which is forwarded to universal server 134. Room controller 168 may respond to the identification signal from sensor 188 by, for example, changing the activated status of indicator light 170 to indicate that a caregiver is in room 180. Sensor 186 may similarly sense the caregiver leaving room 180 and cause room controller 168 to change the activated status of indicator light 170 to indicate that a caregiver is no longer in room 180. Of course, the location information about the caregiver may also be forwarded from universal server 134 via network 19 to server 12. Additionally, sensor 188 may be configured to receive a wireless signal from wall switch 184 such as a nurse call signal or a code blue signal.

Client device 26, as depicted in FIG. 3, includes the combined functions of a pocket PC 196 (generically referred to as a handheld computer), a wireless telephone 198, a pager 200, and a headset 202. Of course, as shown in FIG. 1, client device 26 may further include an RFID interface 42 for reading information from and writing information to RFID tags 24 as further described below.

Figure 4:
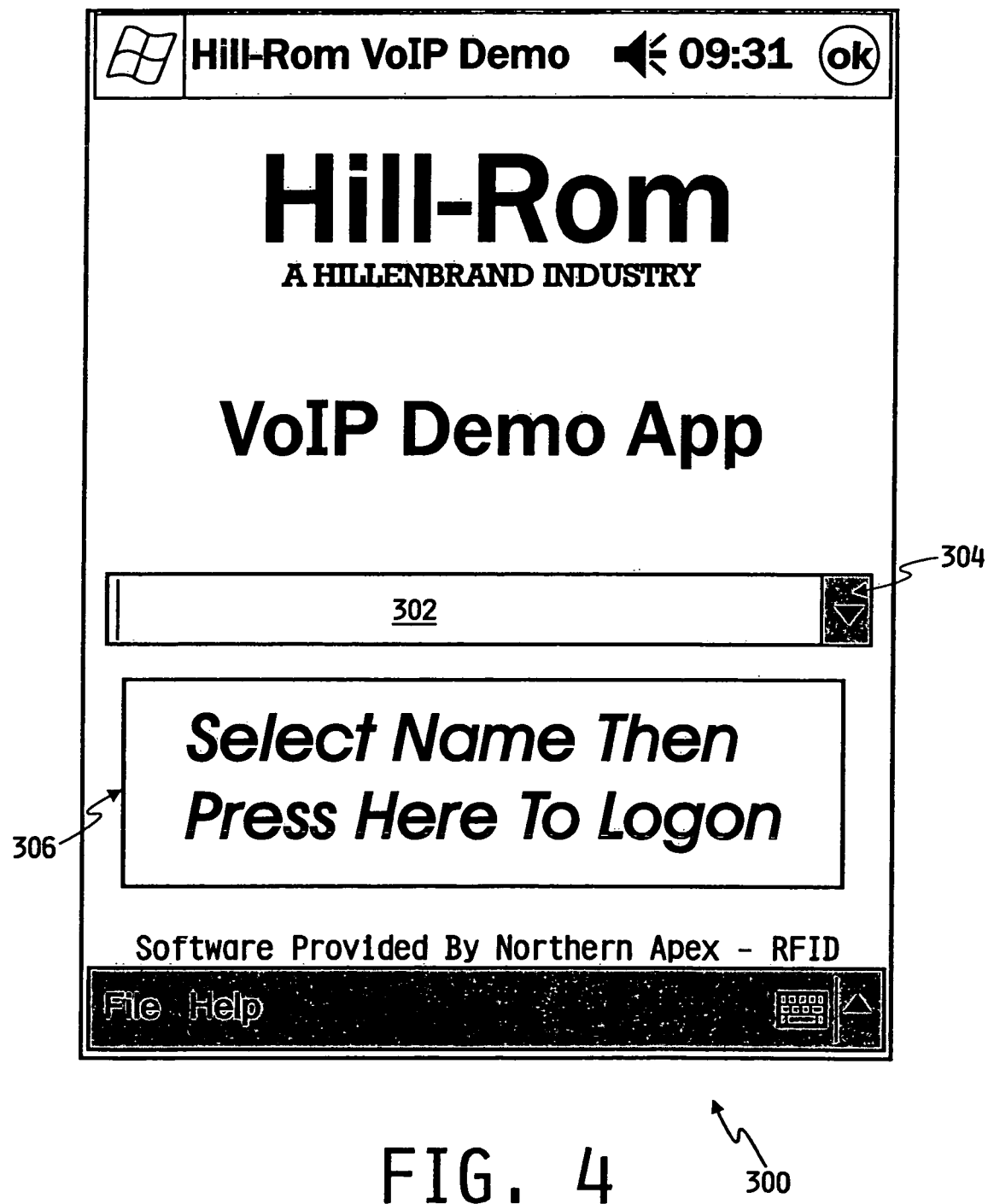
FIGS. 4-19 are screen shots generated by communications software operated by a client device in accordance with the principles of the present invention.

The voice over IP communications features provided by client device 26 are further depicted in FIGS. 4-19. Each of the screens depicted in these figures are generated on display 27 of client device 26 during operation. FIG. 4 depicts a log on screen generated on display 27 of client device 26 when power is applied to client device 26. As shown, screen 300 includes a pull down menu bar 302 activated by button 304, and a message area 306 prompting the user to select a name and activate message area 306 to log on to network 16. It should be understood that the software executed by client device 26 may be configured to automatically log a user on to network 16. More specifically, RFID interface 42 may be used to read an RFID tag 24 associated with or worn by a user to obtain information identifying the user stored in the memory of RFID tag 24. This identification information may be compared to a list of approved users stored in database 40 of server 12. If server 12 determines that the user associated with RFID tag 24 is an authorized user, server 12 may automatically log the user on to network 16. Otherwise, the user activates button 304 on touch sensitive display 27 of client device 26 to obtain a list of authorized users.

Figure 5:
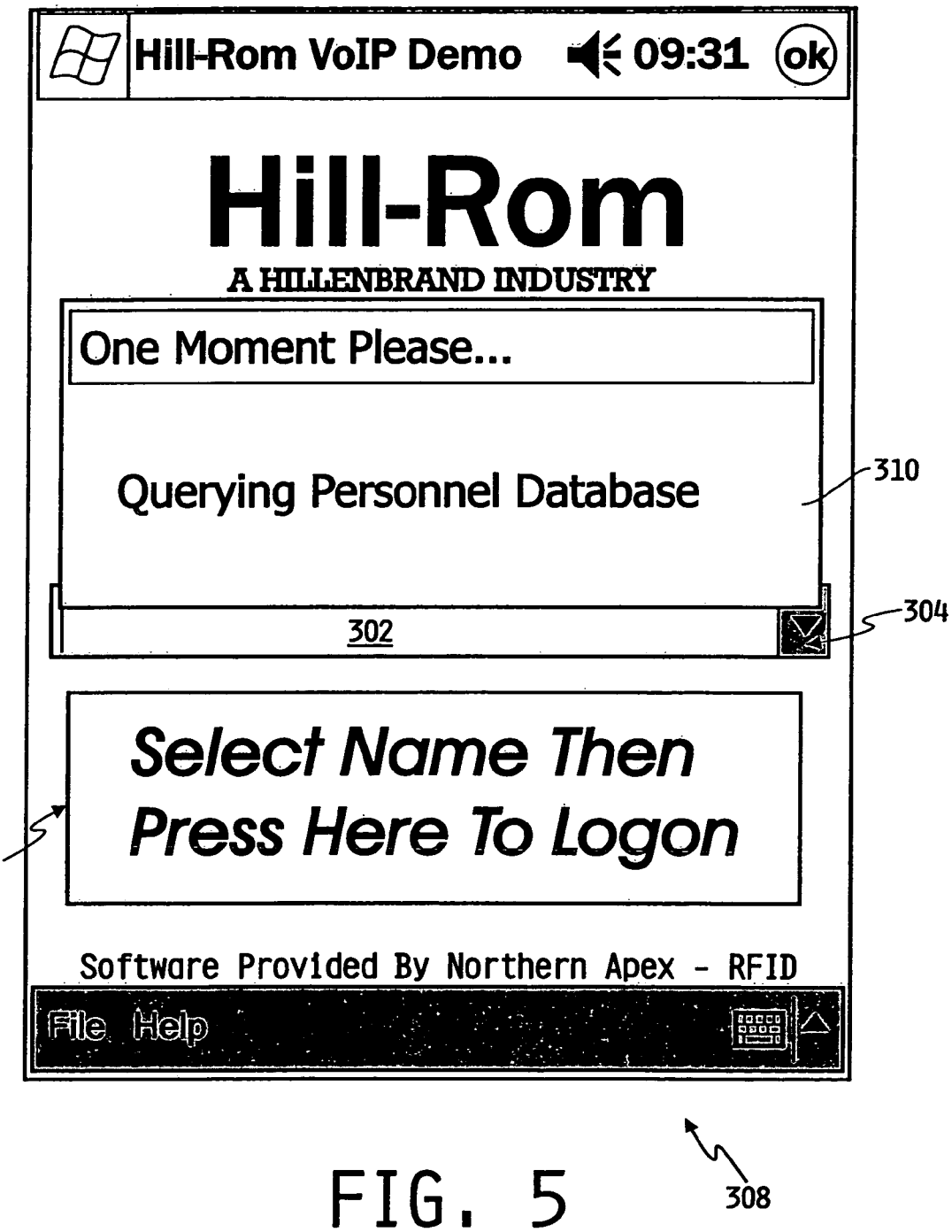
Figure 6:
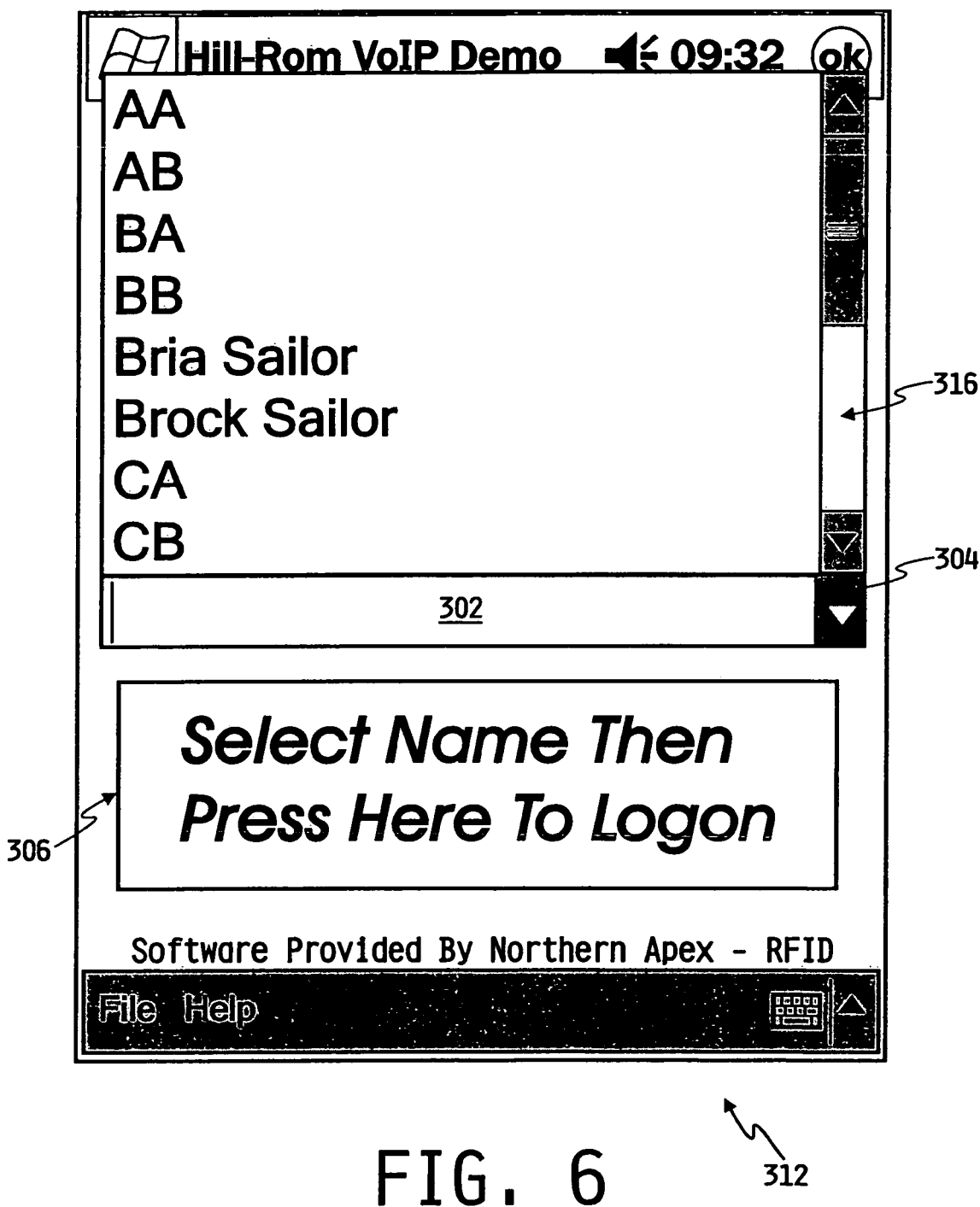

FIG. 5 depicts a temporarily displayed screen 308 that is identical to screen 300 except that a pop-up message area 310 is generated to indicate to the user that server 12 is accessing database 40 to obtain a list of pre-authorized users of network 16. After server 12 accesses the pre-authorized list of users, client device 26 generates screen 312 of FIG. 6. Screen 312 includes a message area 314 that displays the list of authorized users. Screen 312 also includes a conventional scroll bar 316 to enable the user to scroll through the list in area 314. To log on, the user selects his or her name from the list in area 314, then activates area 306 as prompted by screen 312.

Figure 7:
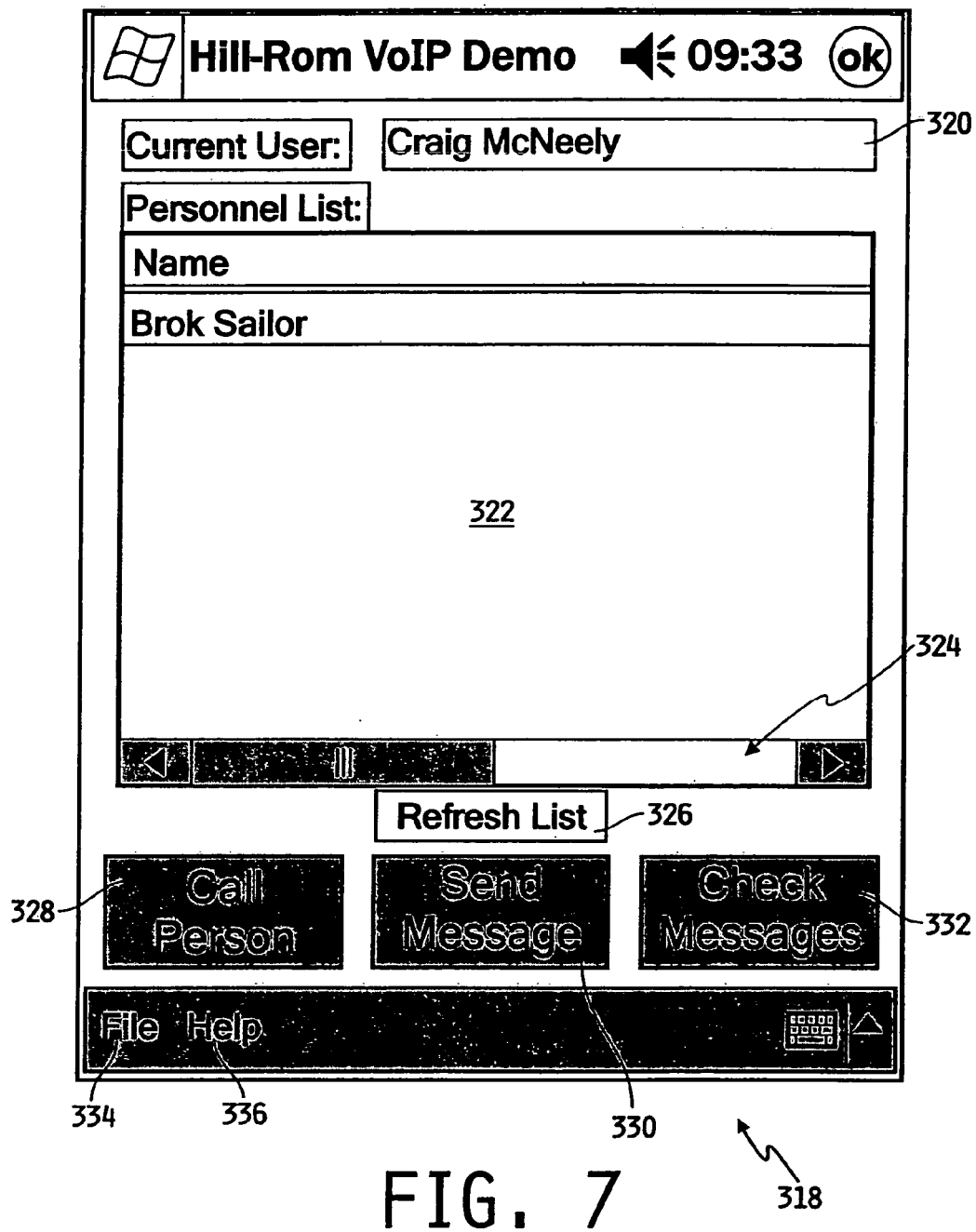

After logging on, the user is presented with main screen 318 as shown in FIG. 7. It should be understood, however, that security measures such as requiring a password may readily be implemented using client device 26. Main screen 318 includes a current user area 320 which displays the name of the current user (i.e., the name selected from the list in area 314 of FIG. 6). Screen 318 also includes a personnel list area 322, a scroll bar 324, a refresh list button 326, a call person button 328, a send message button 330, a check messages button 332, a file drop down menu 334 and a help drop down menu 336. Personnel list 322 lists the names of all other users logged on to network 16. In this example, Craig McNeely has logged on to network 16 as the current user, and Brok Sailor is displayed as the only other user logged on to network 16. Scroll bar 324 is provided to permit the current user to scroll through the list of other users logged on to network 16. As users log on to and log off of network 16, the list displayed in area 322 may be automatically updated by server 12. Alternatively, the current user may be required to periodically update or refresh the list of other users by activating refresh list button 326. As will be further described below, some of the functions of client device 26 are activated using the call person button 328, send message button 330, and check messages button 332.

Figure 8:
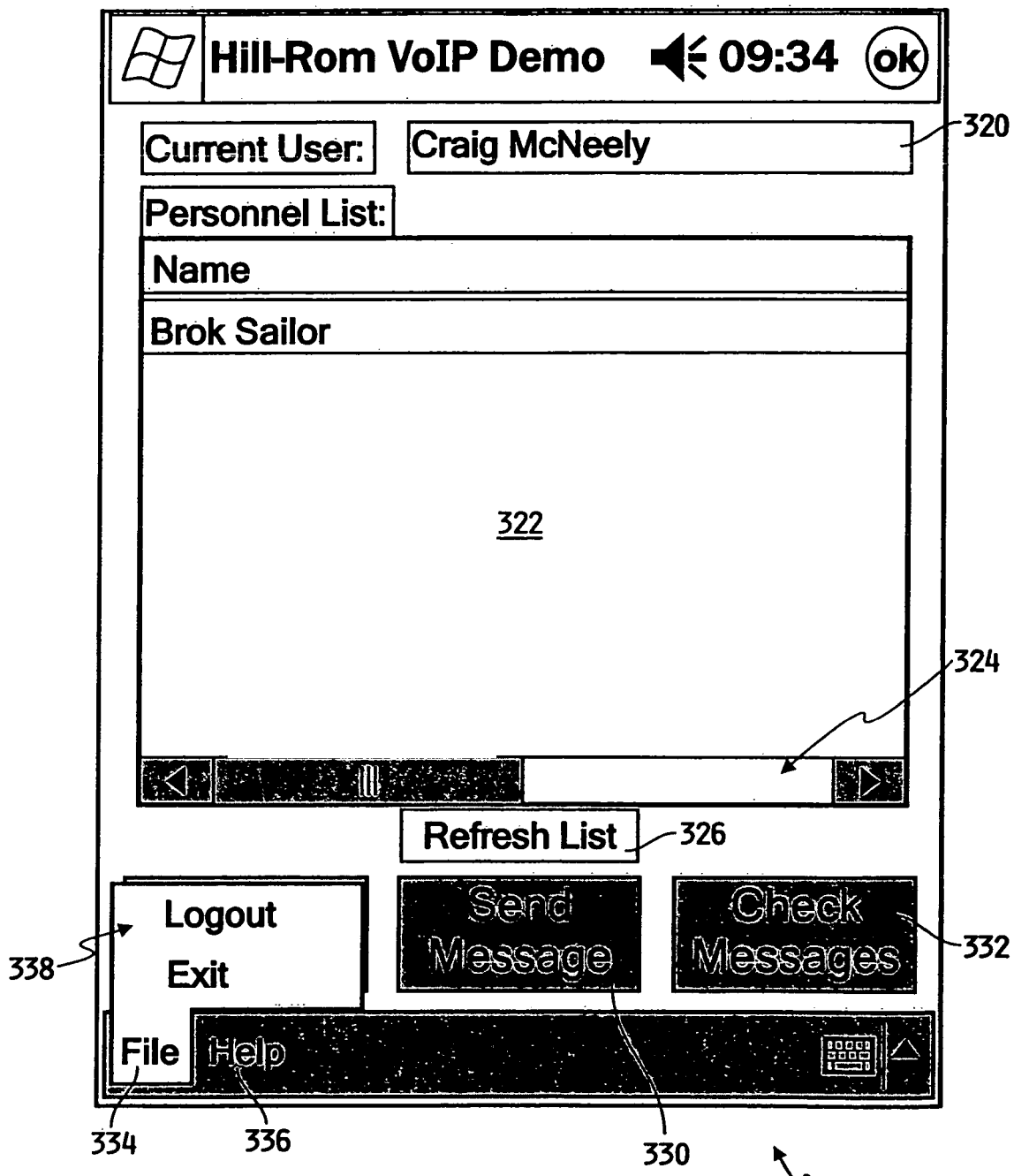

FIG. 8 shows the file drop down menu options displayed in area 338 upon activation of file drop down menu 334. Specifically, the user is presented with the option of exiting the software generating the screens described herein to, for example, run other applications on client device 26, or to log out of network 16 while keeping the software active.

Figure 9:
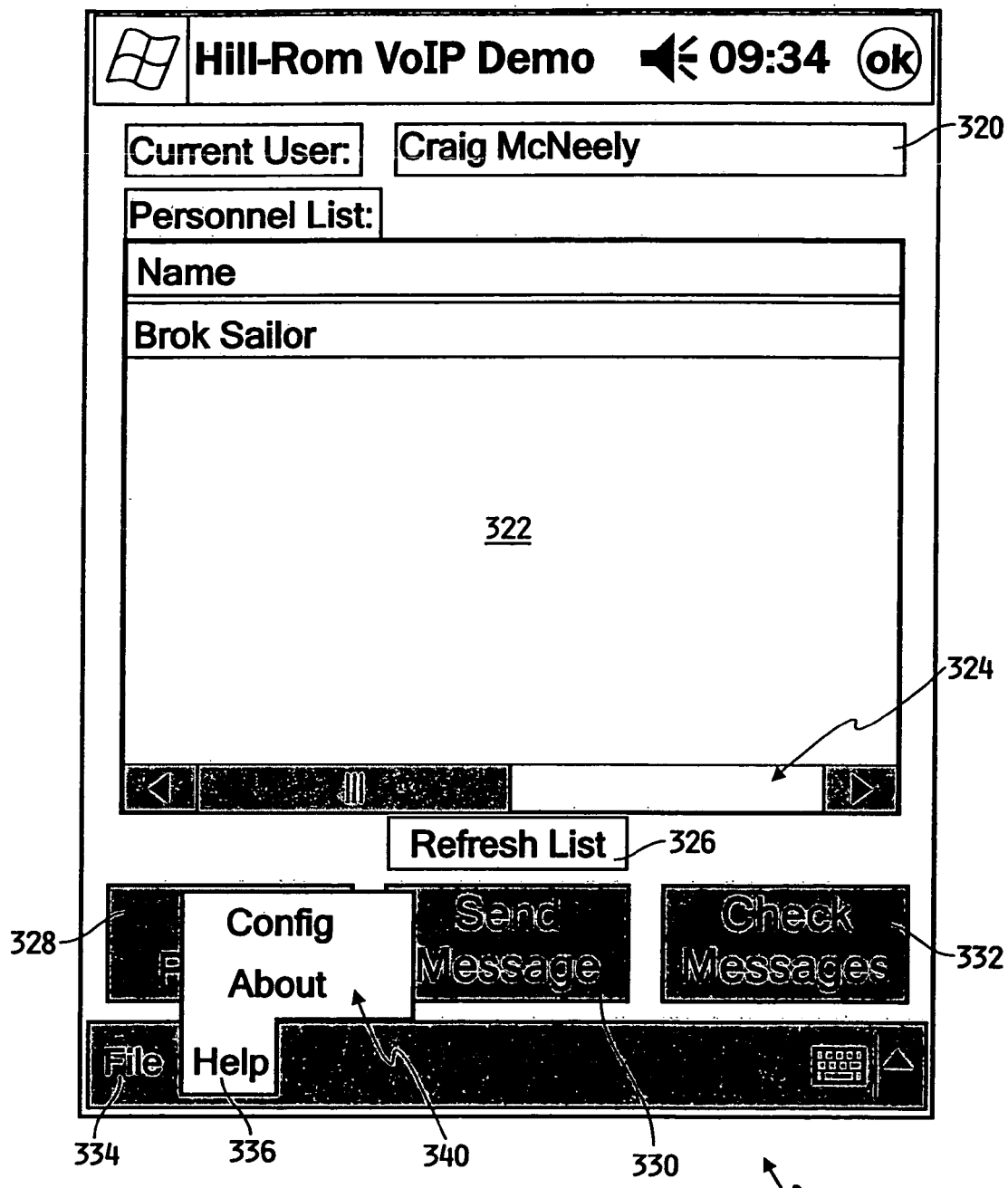
Figure 10:
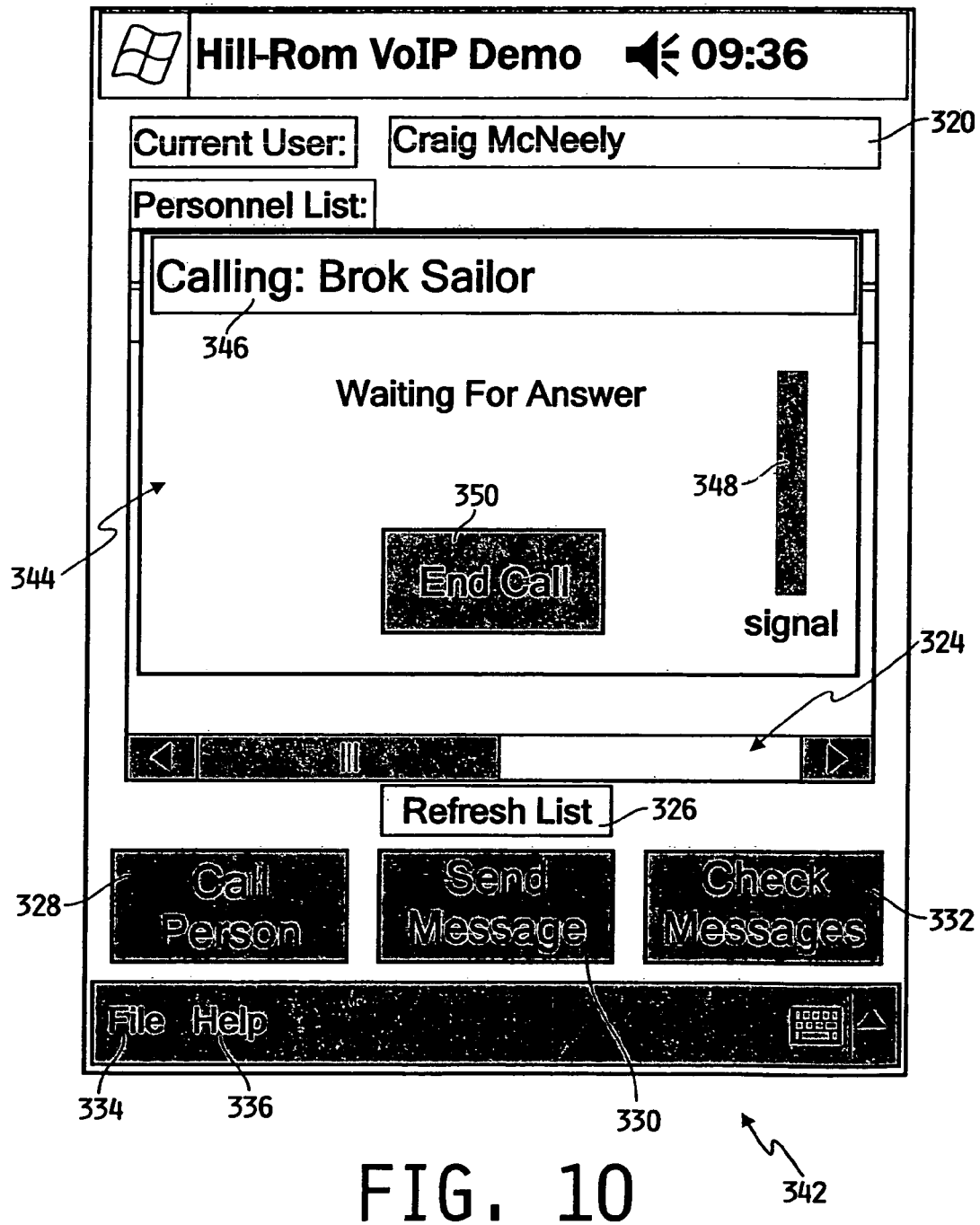

FIG. 9 shows conventional options available upon activation of help drop down menu 336 as displayed in area 340. These options permit the user to configure the system or learn about the application software.

Figure 11:
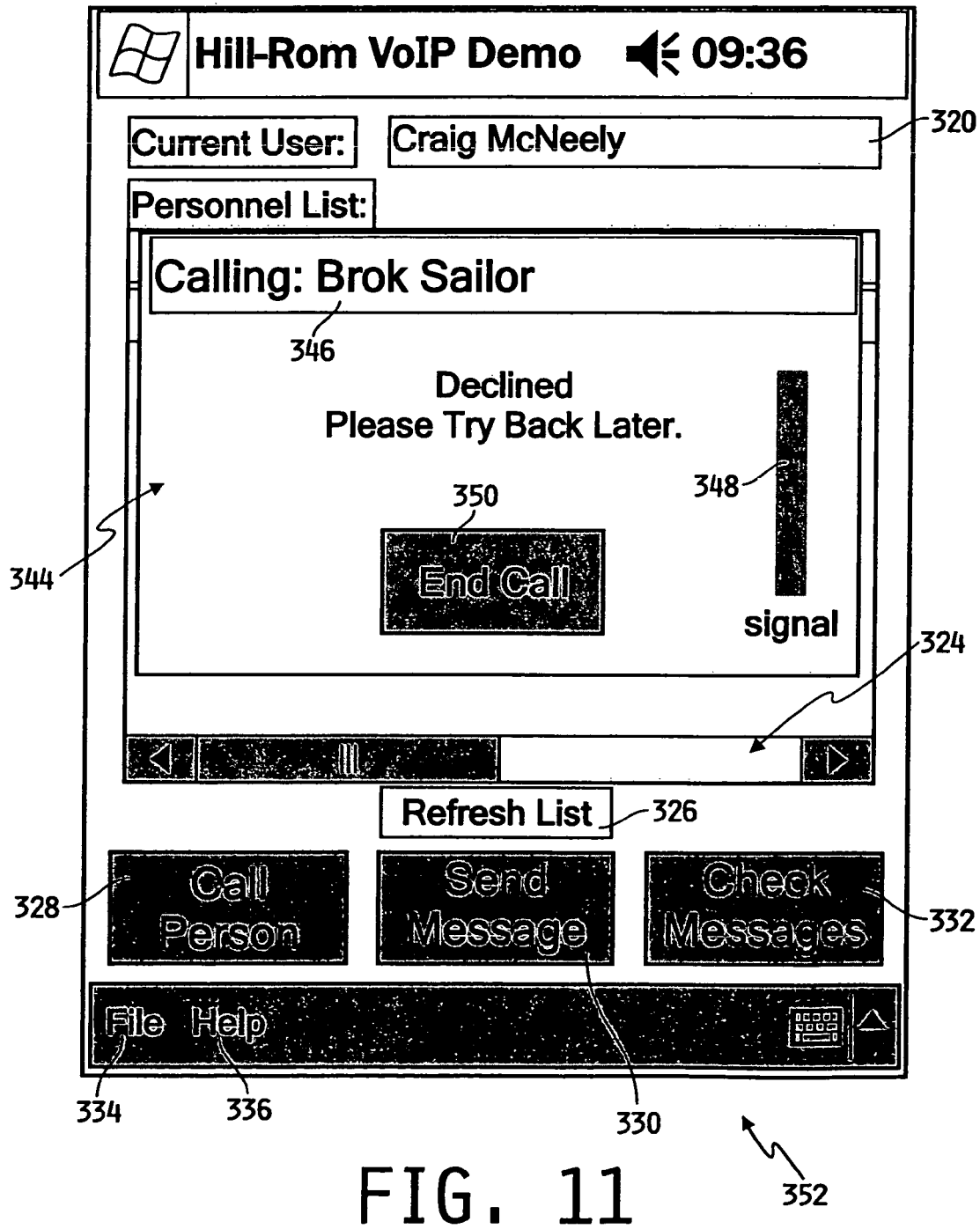

FIGS. 10-14 depict the screens generated during the process of calling another user logged on to network 16 using client device 26. In the following example, the user highlighted the name Brok Sailor on the list of other users logged on to network 16 displayed in area 322 of FIG. 9, and activated call person button 328. While performing this procedure, client device 26 sends a message over network 16 and through one of a plurality of routers 32 to server 12. Server 12 determines the IP address associated with Brok Sailor and generates a signal for transmission to client device 26 associated with Brok Sailor via network 16. During this process, client device 26 of the current user displays screen 342 of FIG. 10, which is essentially identical to screen 318 of FIG. 9 except that personnel list area 322 is replaced with calling user message area 344. Calling user message area 344 includes a status bar 346 that indicates the name of the user being called, a signal strength graphic 348, and end call button 350. If the user being called is busy or otherwise decides not to take the call (as explained below with reference to FIG. 13), message area 344 informs the user that the intended recipient of the call has declined to answer as shown in FIG. 11. Additionally, server 12 may be configured to initiate a timer after a call request is transmitted over network 16 to an intended recipient. If the intended recipient fails to accept the call within a predetermined time, server 12 may send a signal to the calling client device 26 that generates screen 352 of FIG. 11.

Figure 12:
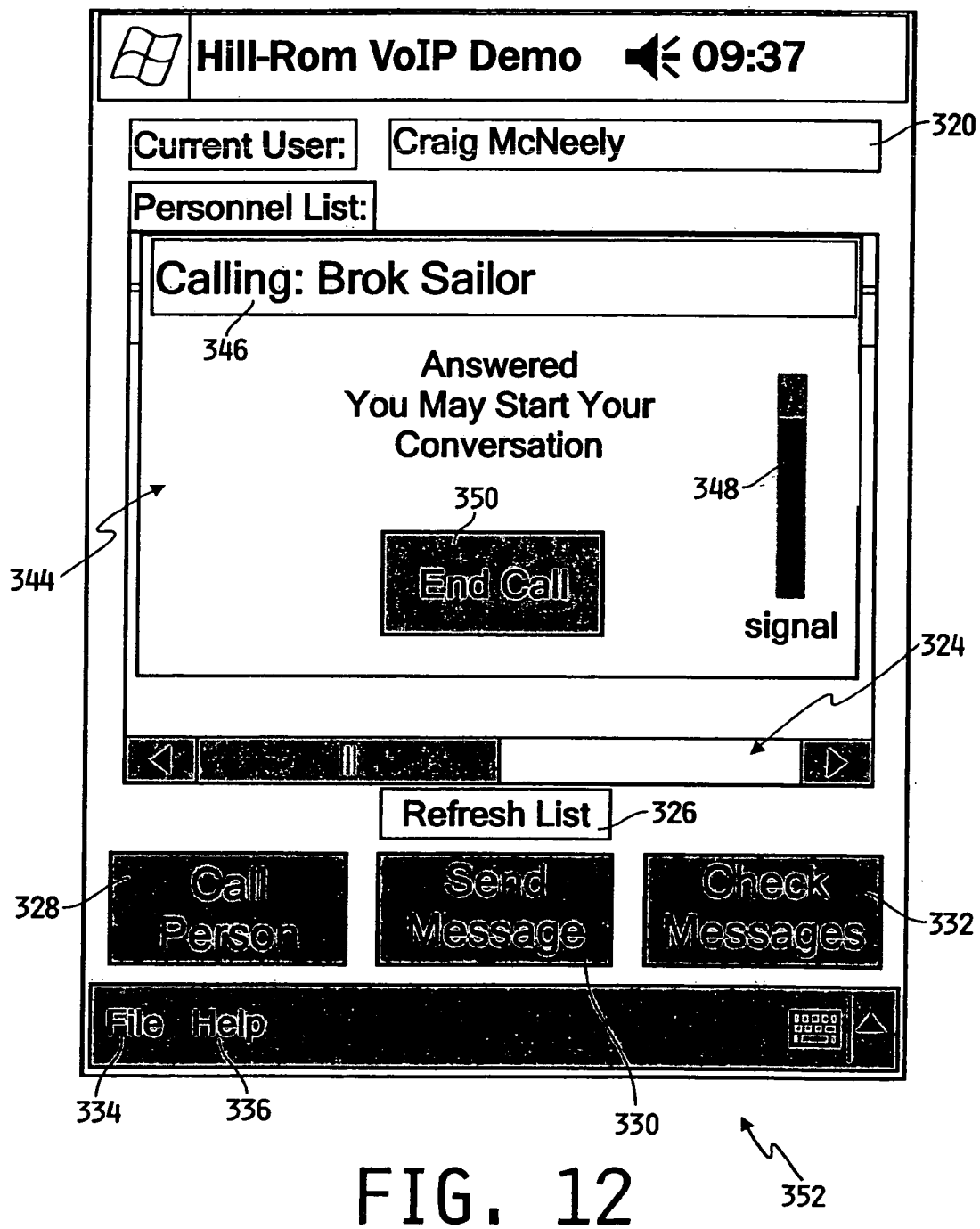

Referring now to FIG. 12, if the intended recipient accepts the call as explained below with reference to FIG. 13, message area 344 displays a prompt to the current user to begin a conversation. Also, signal strength graphic 348 is activated to provide a visual indication of the strength of the signals between the two communicating client devices 26. Signal strength, as is well known in the art, may be dependent upon a variety of factors including the distance between client devices 26 and access points to network 16, obstructions between such locations, etc. Once the connection between client devices 26 has been established, client devices 26 essentially function as walkie talkies wherein the users may speak into the microphones of client devices 26 and listen to the other user through a speaker, headset, or other audio output.

Figure 13:
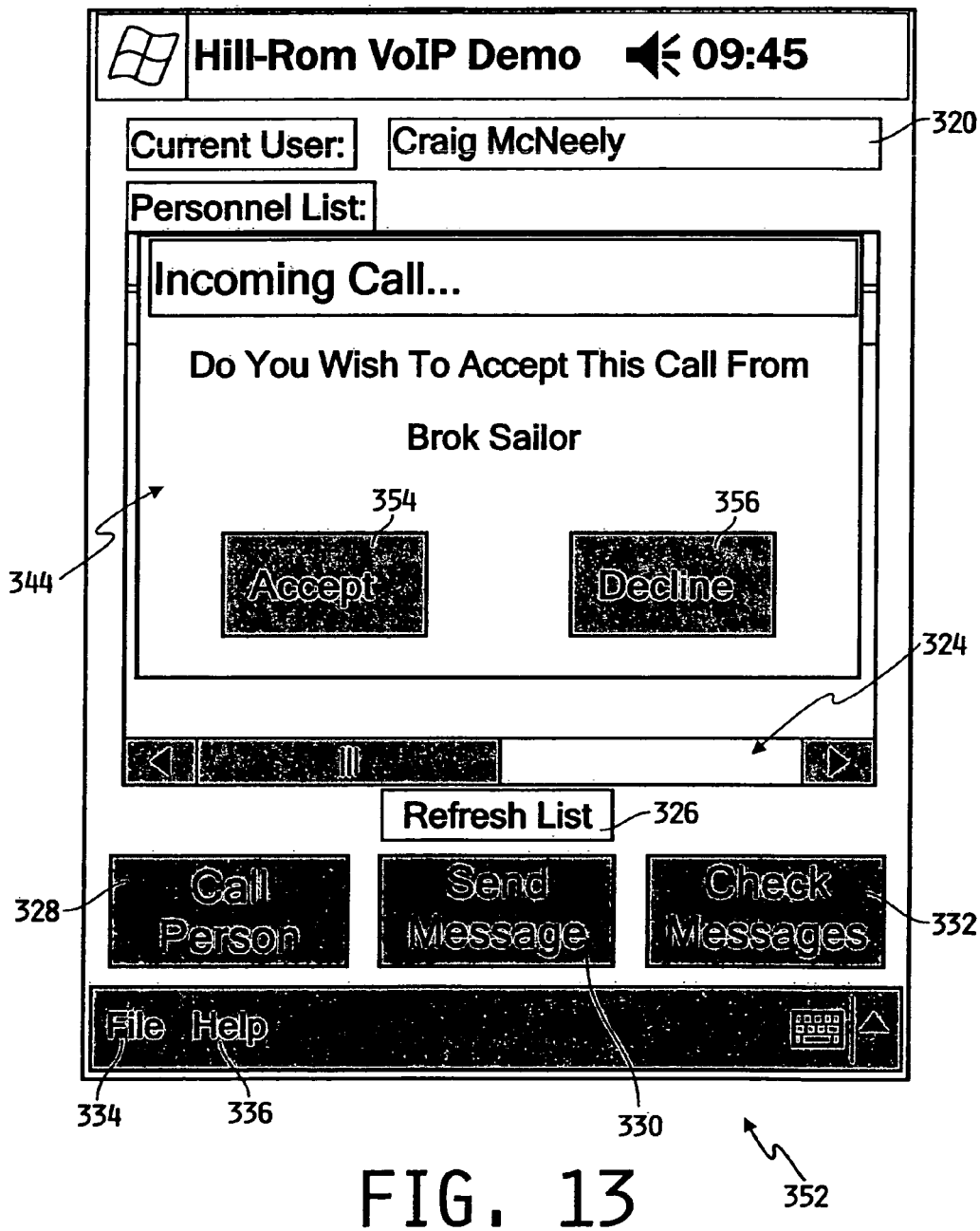
Figure 14:
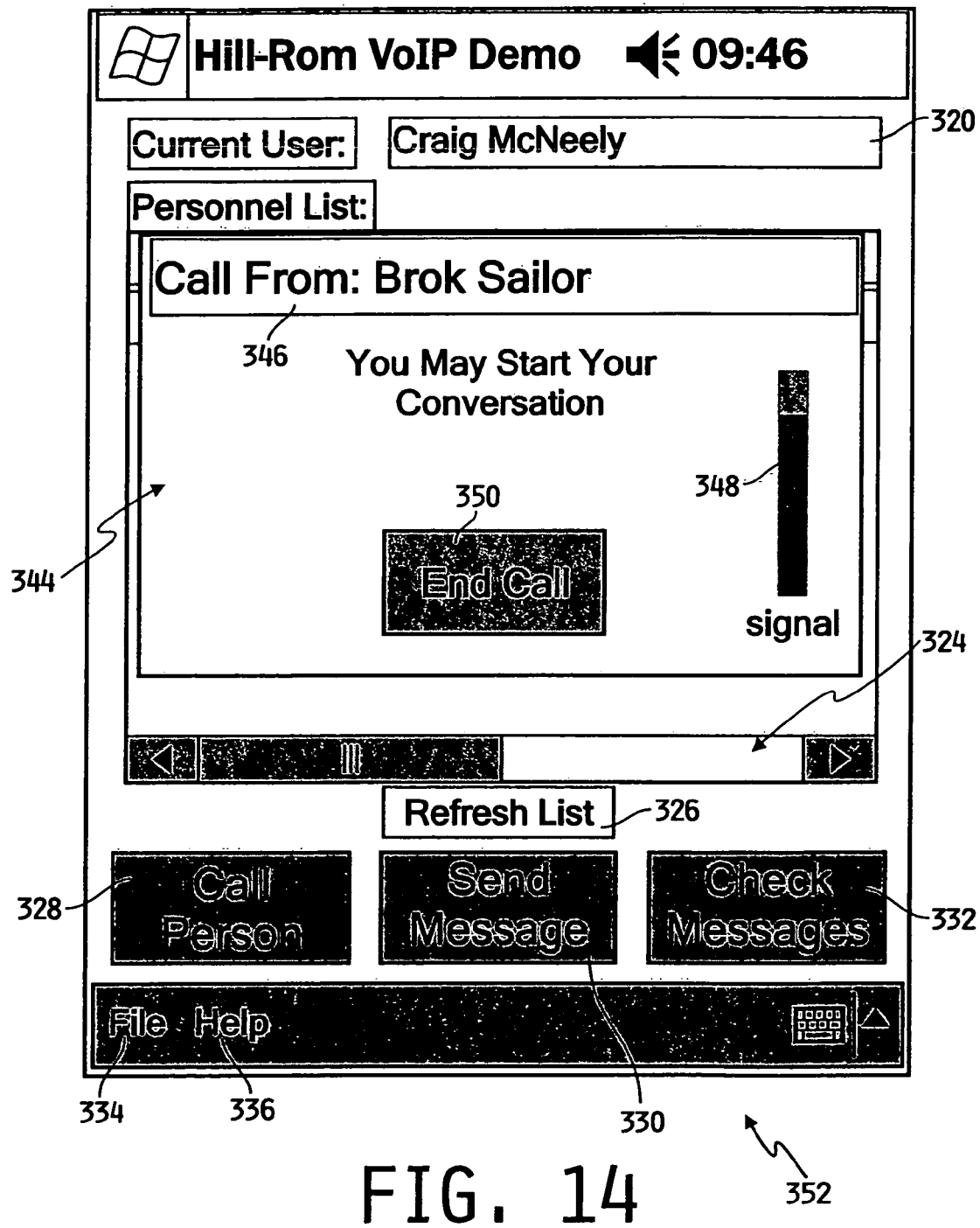

FIG. 13 shows screen 352 as modified to indicate an incoming call. An incoming call may occur either while the user is logged on to network 16 but not actively communicating with another user, or during an active conversation. In either event, message area 344 is generated as shown in FIG. 13 to indicate to the user that an incoming call is being attempted, and who the caller is. The user may activate either the accept button 354 to connect to the incoming caller or the decline button 356. If the user activates accept button 354, then message area 344 is updated as shown in FIG. 14. Message area 344 is similar to that shown in FIG. 12 except that it indicates who is calling in status bar 346 instead of whom the current user is calling.

It should be understood that it is well within the ability of the skilled artisan to configure the communications software of the present invention to enable various other communications features often associated with conventional telephone systems. For example, call forwarding (including automatic shut-off after a predetermined time elapses without an answer), call transferring, call hold features, call history, and call waiting are well within the scope of the teachings of the present invention. Additionally, telephone directories stored in database 40 may be accessed by client device 26. Also, patients may be permitted to use devices similar to client devices 26 to call caregivers. In such an embodiment, the patient name and room number may be displayed in message area 344. A call code may also be displayed to indicate the nature and/or urgency of the call. Moreover, displays of waveforms or other output signals from equipment may be received by client devices 26, displayed on display 27, transferred to database 40, and retrieved at a later time. It should further be understood that distinct ringing sounds may be generated by client devices 26 to indicate certain types of incoming calls and/or messages (e.g., code blue calls).

Figure 15A:
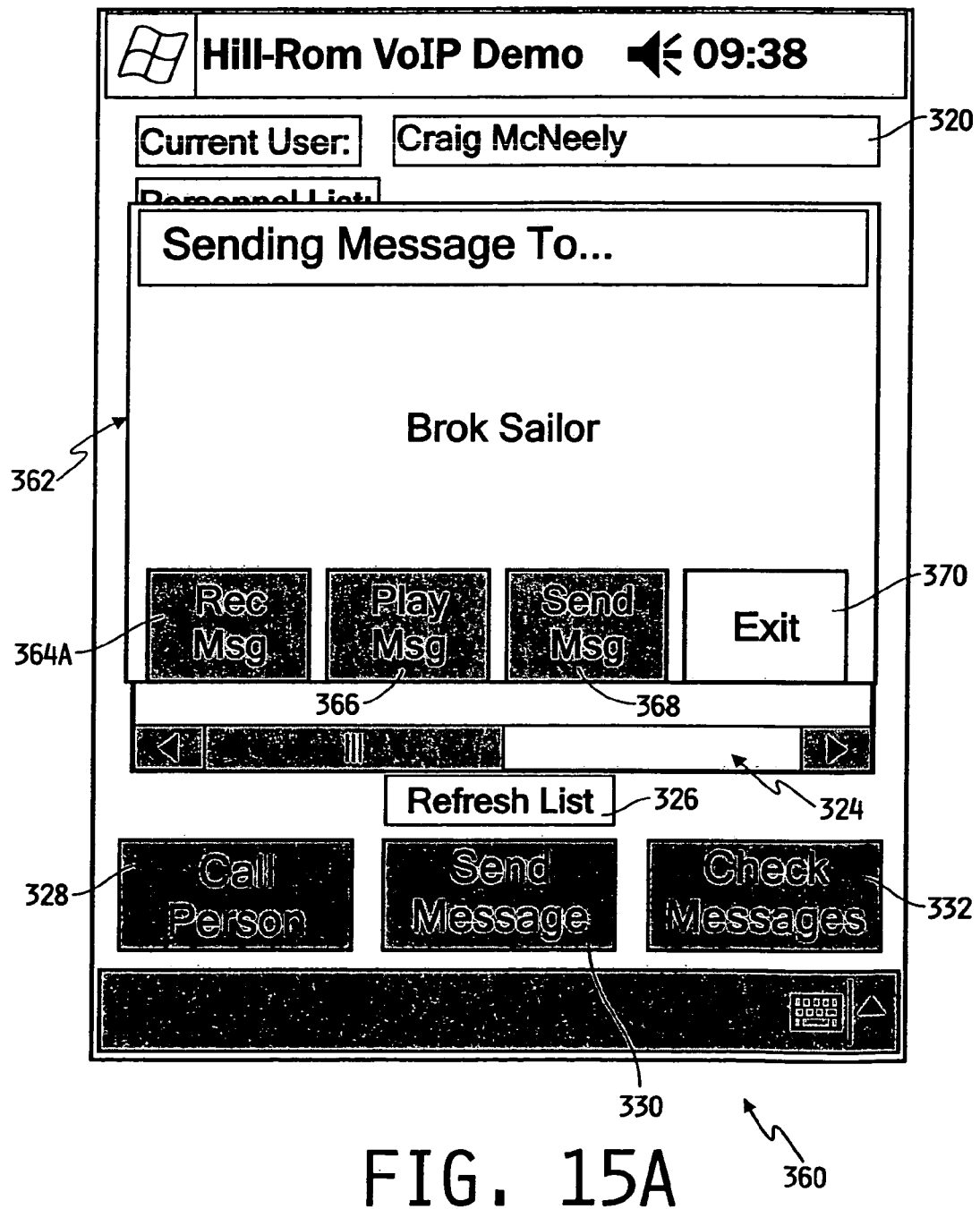
Figure 15B:
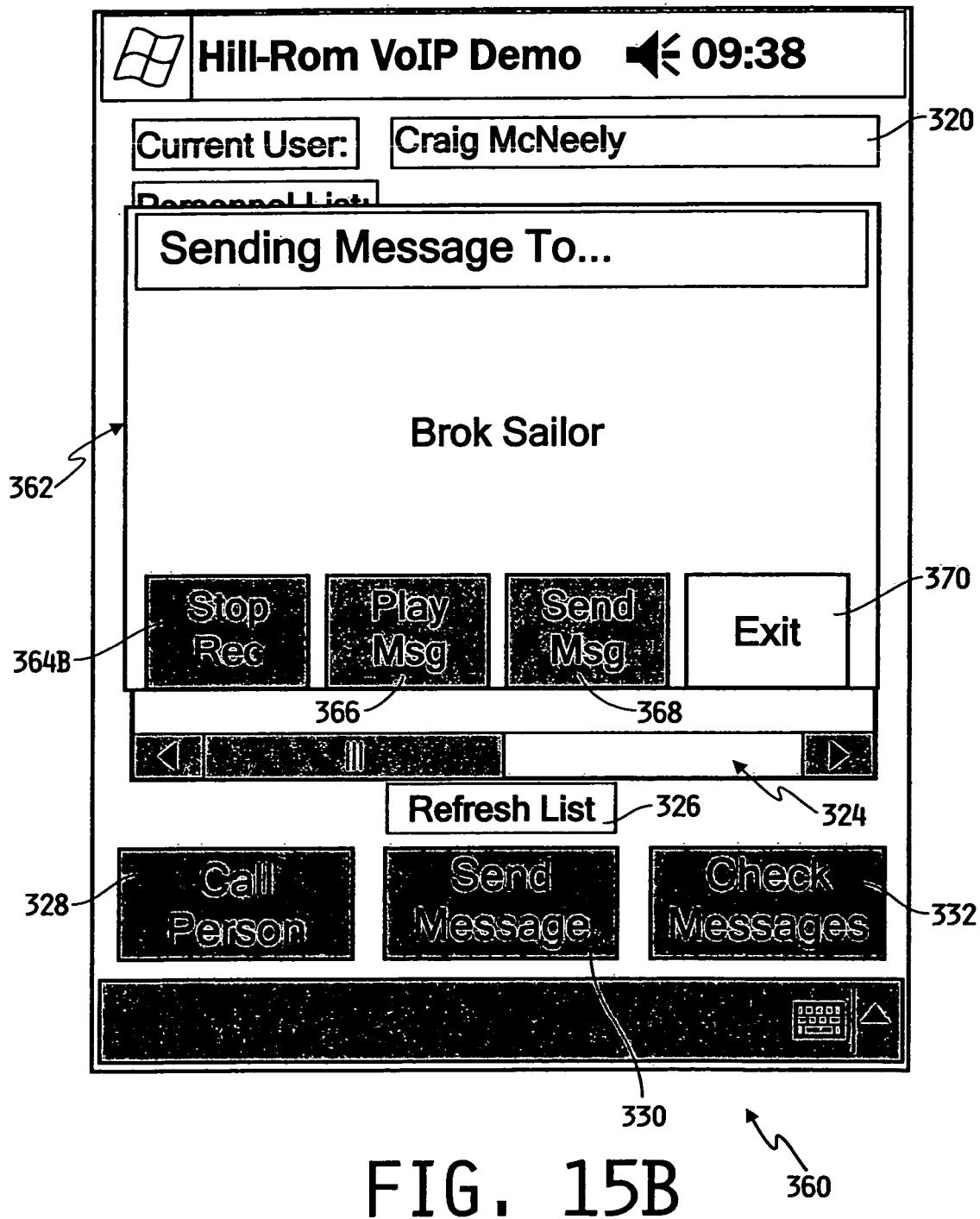
Figure 16:
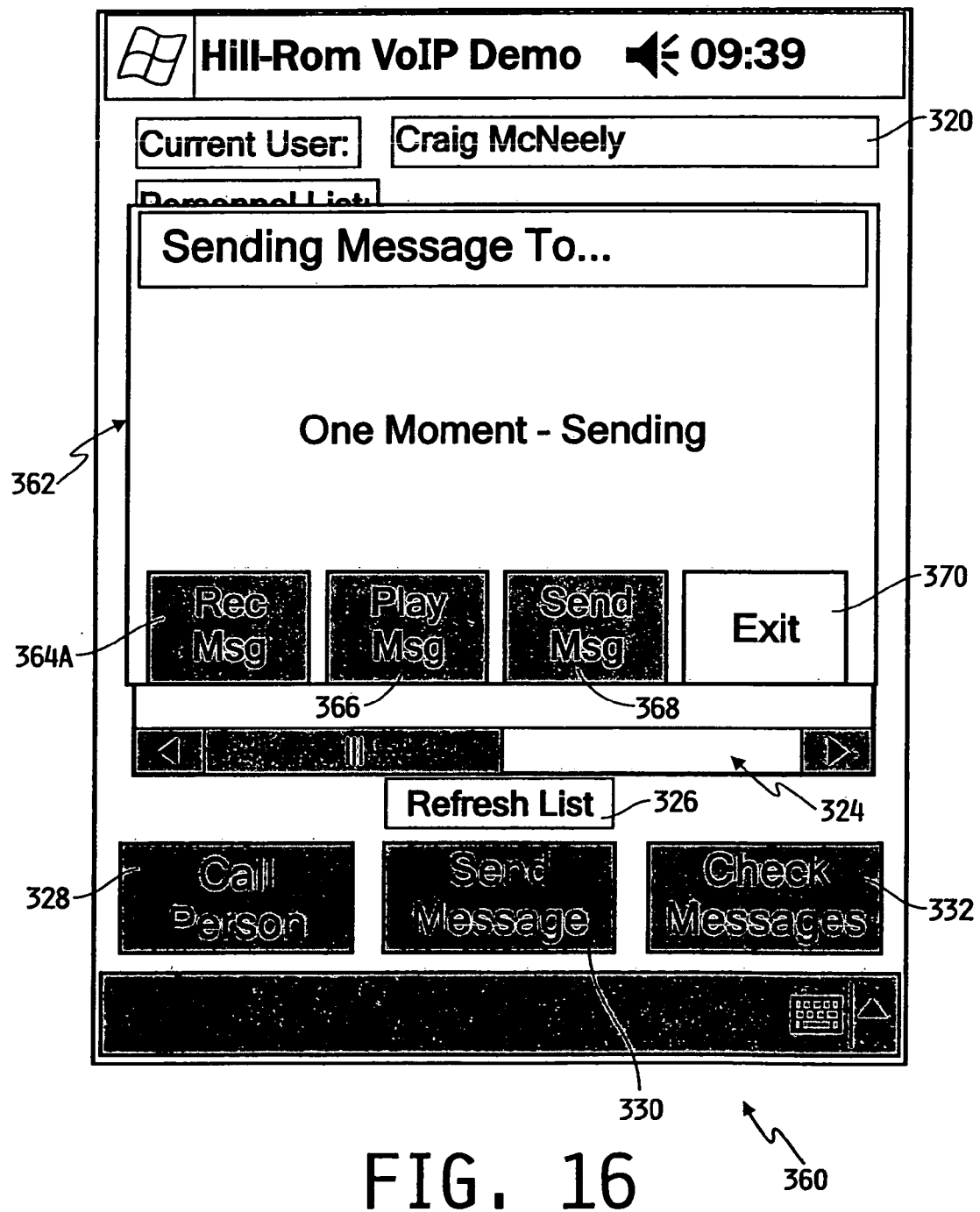
Figure 17:
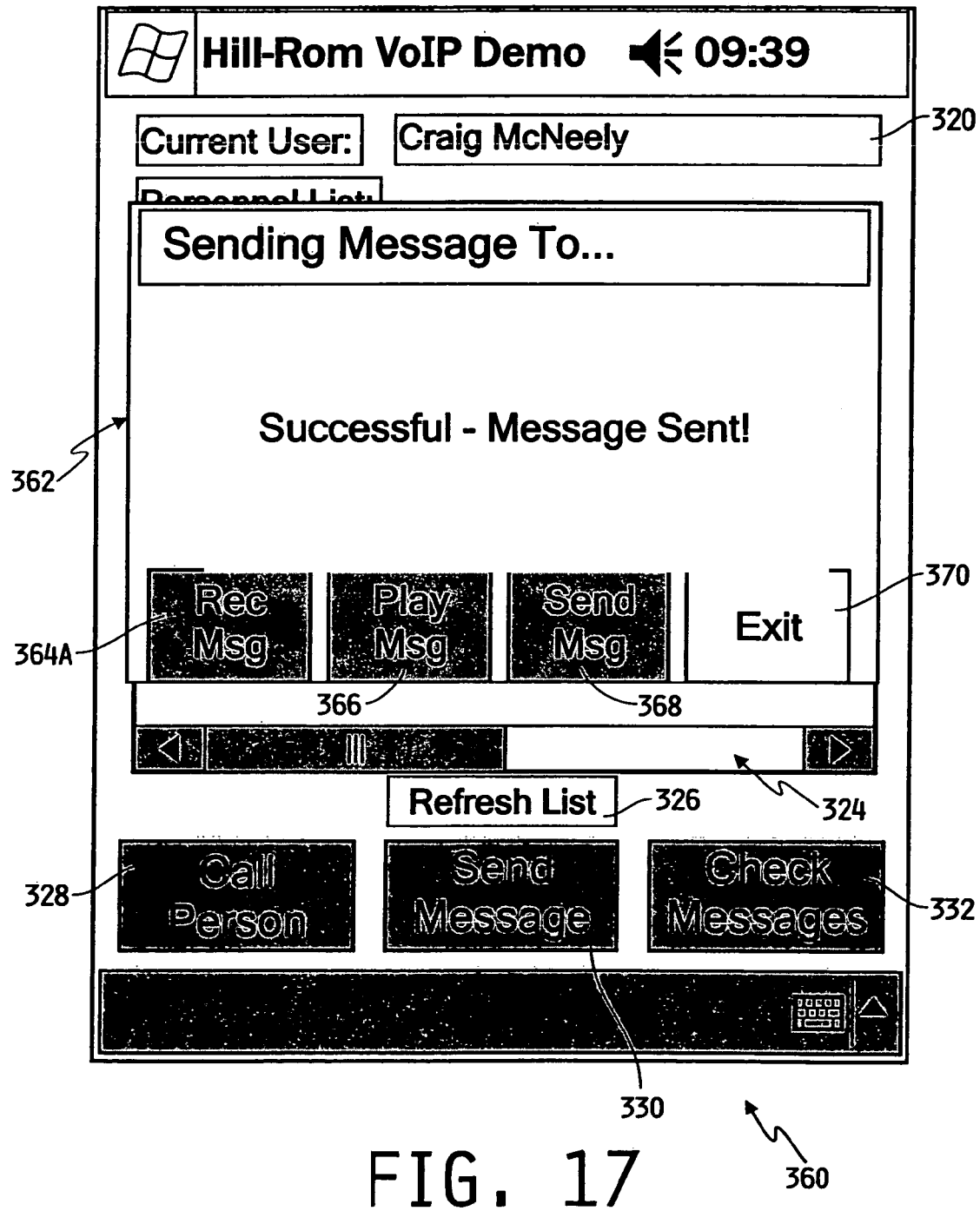

FIGS. 15A-19 show screens generated during the process of creating, reviewing, and sending a message to another user using client device 26. Beginning with screen 318 of FIG. 7, the current user may highlight another logged on user and then activate send message button 330. Upon activating send message button 330, screen 360 is displayed including pop-up message control area 362. As shown in FIG. 15A, message control area 362 indicates the intended recipient for the message as selected by the current user, and includes a record message button 364A, a play message button 366, a send message button 368, and an exit button 370. The user may begin recording a message by activating the record message button 364A and speaking into the microphone of client device 26 to record a message for the intended recipient. When the user is finished recording the message, the user activates the stop recording message button 364B (which is generated after record message button 364A is activated) as shown in FIG. 15B. The user may review the recorded message by activating play message button 366 as shown in FIG. 16. After the user has reviewed the message, the user may activate send message button 368 which causes client device 26 to output the audio message to network 16 for transmission to the intended recipient. At any time during the record, playback, or send procedures, the user may activate exit button 370 to abort the send message process. After the user activates send message button 368, a message is temporarily displayed in control area 362 indicating that the message in the process of being sent as shown in FIG. 16. While audio signals may be sent between users in the manner described above, it should be understood that by employing conventional audio to text technology, messages may be converted prior to sending or upon receipt from audio signals to text. Use of such technology reduces the amount of memory consumed on client device 26 by stored messages, and permits storage of messages on, for example, server 12 for record keeping or other purposes. If stored in a text format, messages may be later searched for key words, printed, or otherwise processed. When transmission of a message, either audio or textual, is completed, client device 26 generates an indication in control area 362 to inform the user that the message was successfully sent as shown in FIG. 17.

Figure 18:
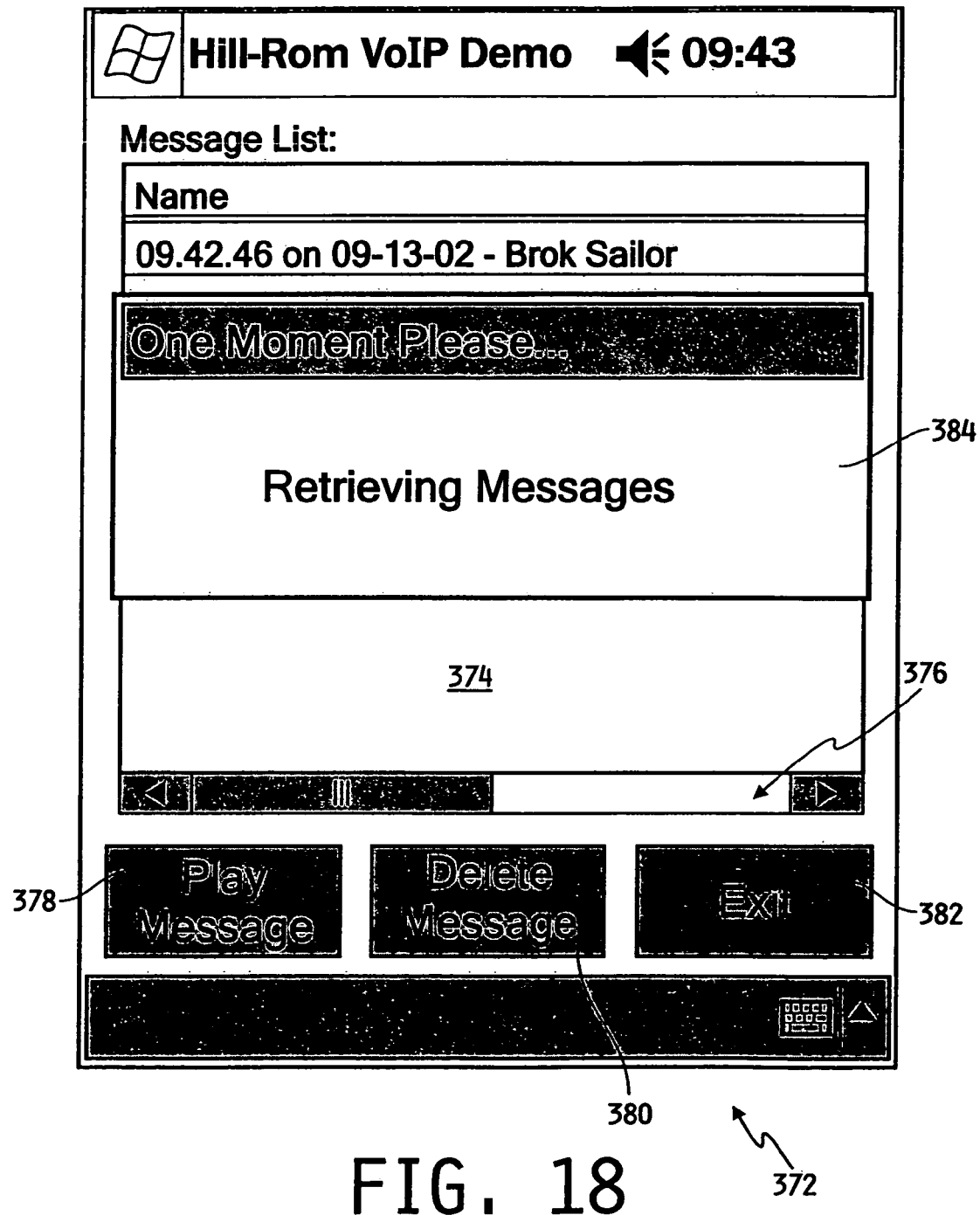
Figure 19:
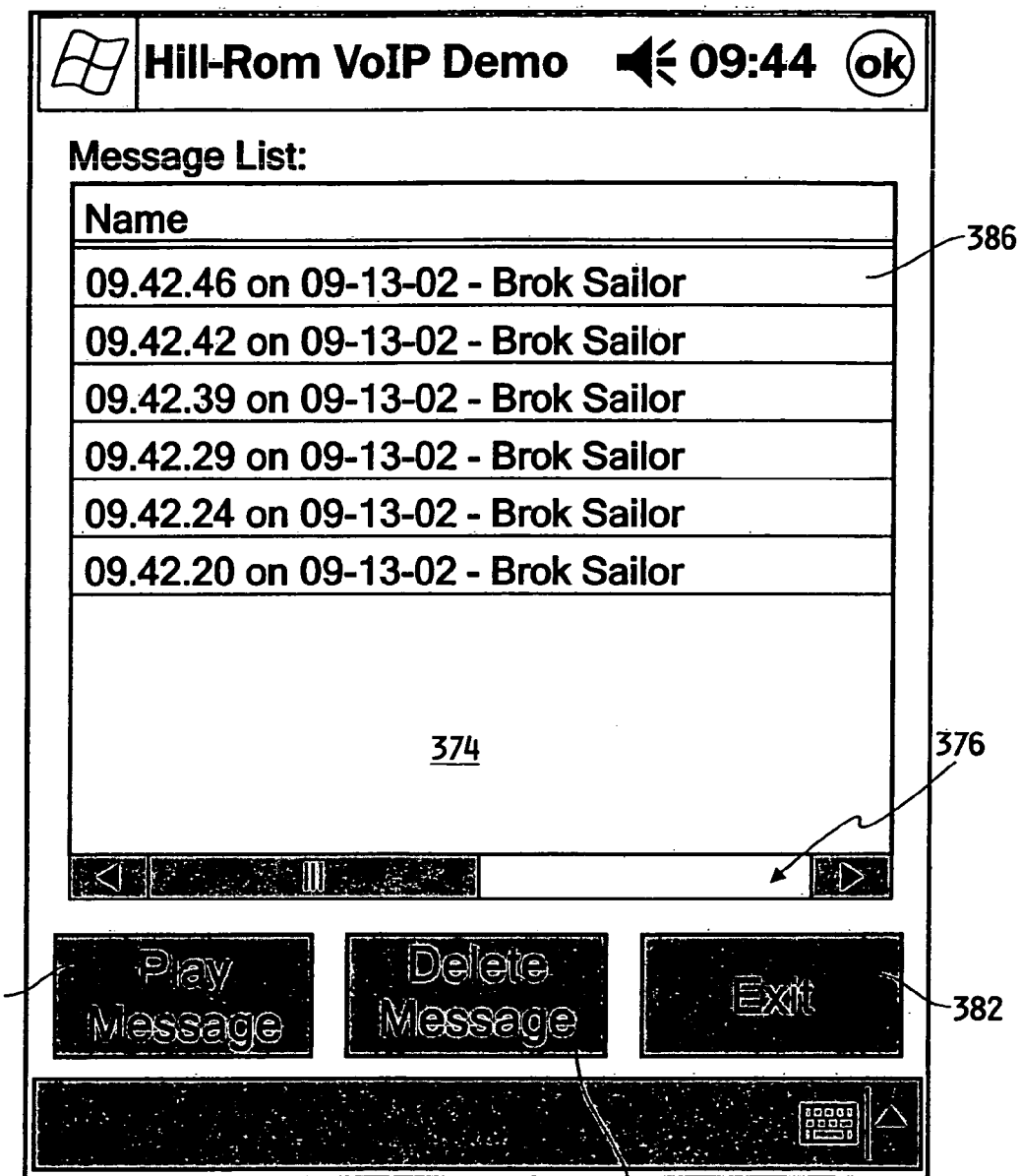

Referring now to FIGS. 18 and 19, users may play back stored messages or delete them by activating check messages button 332 from, for example, main screen 318 as shown in FIG. 7. Upon activating check messages button 332, screen 372 is displayed on display 27 of client device 26. Screen 372 includes a message listing area 374, a scroll bar 376, a play message button 378, a delete message button 380, and an exit button 382. Additionally, as client device 26 retrieves messages stored thereon, the application software generates a pop-up message 384 indicating to the user that retrieval of messages is in process. As shown in FIG. 19, all of the stored messages, once retrieved, are listed in message listing area 374. Each entry 386 includes the date and time the message was received and the name of the author of the message. The user may scroll through the messages using scroll bar 376. The user may also highlight a particular message, play it by activating play message button 378, or delete it by activating delete message button 380. The user may exit screen 372 and return to main screen 318 by activating exit button 382.

Among other things, the various networks and systems described above provide automatic data collection that may be used in a plurality of different ways. By receiving continuously updated information about the location of the various people, equipment, and supplies, system 10 maintains an accurate database (such as database 40) of the current locations of such assets. Additionally, by retaining a history of such location data, the status of assets may readily be determined by applying certain logical rules. For example, if a caregiver is detected at a handwashing station, then system 10 may update the caregiver's hygiene compliance status to "clean." If a caregiver leaves a patient's room without washing his or her hands, then system 10 may update the caregiver's hygiene compliance status to "contaminated." If the caregiver then enters another patient's room, system 10 may automatically prompt the caregiver to wash his or her hands by sending a message to client device 26 associated with the caregiver, activating a light attached to active tag 22 worn by the caregiver, causing indicator light 170 to flash or otherwise indicate a warning condition, causing an automatic message to be played over RAS 172, or otherwise urging compliance with the facility hygiene policy. Other details regarding hygiene compliance applications for system 10 are described in the co-pending U.S. patent application Ser. No. 09/699, 796, entitled "HYGIENE MONITORING SYSTEM," filed Oct. 30, 2000 and referenced above.

Another application of system 10 is automatic dispatching of messages. For example, when wall switch 184 is activated to indicate a code blue condition, the location of the code blue source may be determined by system 10 as well as the identities of caregivers in proximity of room 180. System 10 may then automatically transmit a code blue message indicating the location of the code blue source to those caregivers nearest to the source. Such messages may be transmitted as text (e.g., an email message) over network 16 to client devices 26 carried by the caregivers. Client device 26 may be configured to activate an audible indicator (e.g., the speaker of client device 26) to notify the caregiver of the receipt of a code blue message. Additionally, system 10 may cause transmitters 18 to transmit a signal to an active tag 22 worn by the caregiver to activate a light on tag 22 to indicate that a code blue message has been sent to the caregiver. The caregiver may then respond to the code blue condition by entering room 180. Movement of the caregiver into room 180 may be detected by either of transceivers 18, 20 (FIG. 1) or sensor 188 (FIG. 3). The presence of the caregiver in room 180 may then cause system 10 to send another signal to client device 26 to clear the code blue message. If a caregiver does not respond to the code blue message within a predetermined time period, additional caregivers (e.g., caregivers farther from the code blue source) may be automatically notified by system 10 of the code blue condition. Any other type of activity based automatic notification process may be employed using system 10.

Another application of system 10 is associating information with assets and updating the information to indicate the present status of the assets. In one embodiment, system 10 facilitates association of information with patients, caregivers, and other assets in a hospital and, in addition to automatically updating the associated information as further described herein, enables caregivers, administrators, and other personnel to update the information as the status of the tagged person or other asset changes. In this embodiment, a patient may be processed using a conventional admissions procedure wherein information relating to the patient is manually entered at a processing terminal such as workstation 28. This information may then be provided to server 12 via network 14 for storage in database 40. Additionally, RFID interface 30 may be used to create an RFID tag 24 for the patient as further described below. RFID tag 24 may include a conventional plastic wristband with an RFID device attached thereto (or printed thereon using an RFID printer as described in co-pending U.S. patent application Ser. No. 10/154,644 referenced above). As the patient moves throughout the facility as detected by transceivers 20, the location information associated with the patient (as identified by the RFID unique identification number stored in the memory (not shown) of RFID tag 24) may be automatically updated by server 12 in database 40. As is also further described herein, caregivers and/or other personnel may write information to the patient's RFID tag 24 to indicate the occurrence of certain events including administration of medications, completion of therapies, evaluations, etc. This updated status information may be read by transceivers 20 (or RFID interfaces 30 or 42), transmitted over the appropriate network 14, 16 or combination thereof, and stored in database 40 by server 12. One software application for associating information with RFID tags 24 is depicted in FIGS. 20-33 and described below.

FIGS. 20-33 are screen shots generated by RFID software for execution by an administrator or other facility personnel on a computing device such as server 12, workstation 28, or other suitable device connected to server 12. In this description, it is assumed for simplicity that the software is executed on workstation 28. In general, the RFID software application functions as an interface between RFID interface 30 and database 40. More specifically, the RFID software enables the user to create RFID tags 24 for patients, personnel, and other assets, as well as inputting information for association in database 40 with the particular asset corresponding to the created RFID tag 24.

Figure 20:
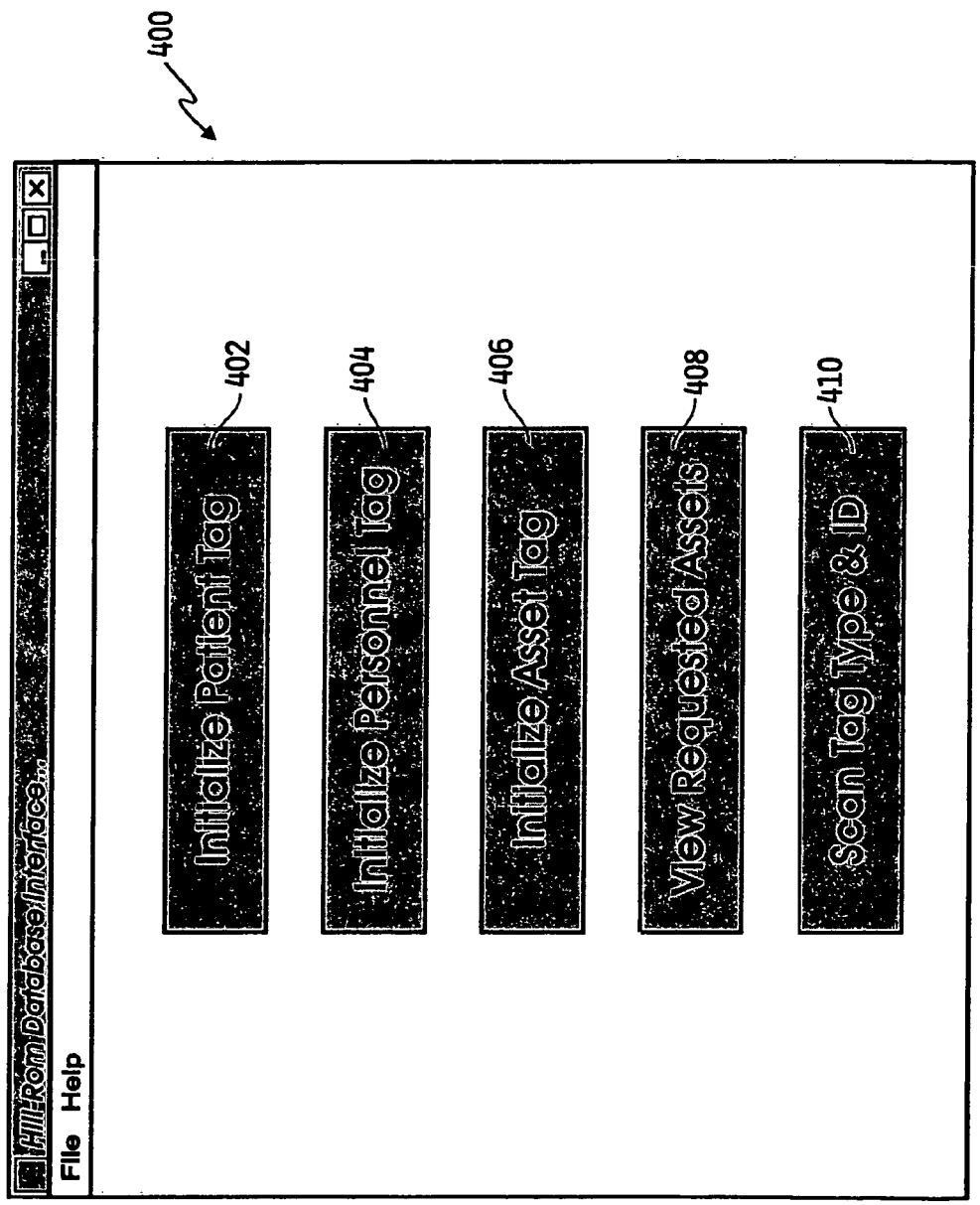

Referring now to FIG. 20, the RFID software first generates a main screen 400 including an initialize patient tag button 402, an initialize personnel tag button 404, an initialize asset tag button 406, a view requested assets button 408, and a scan tag type and ID button 410. The functions of each of these buttons are discussed in turn below.

Figure 21:
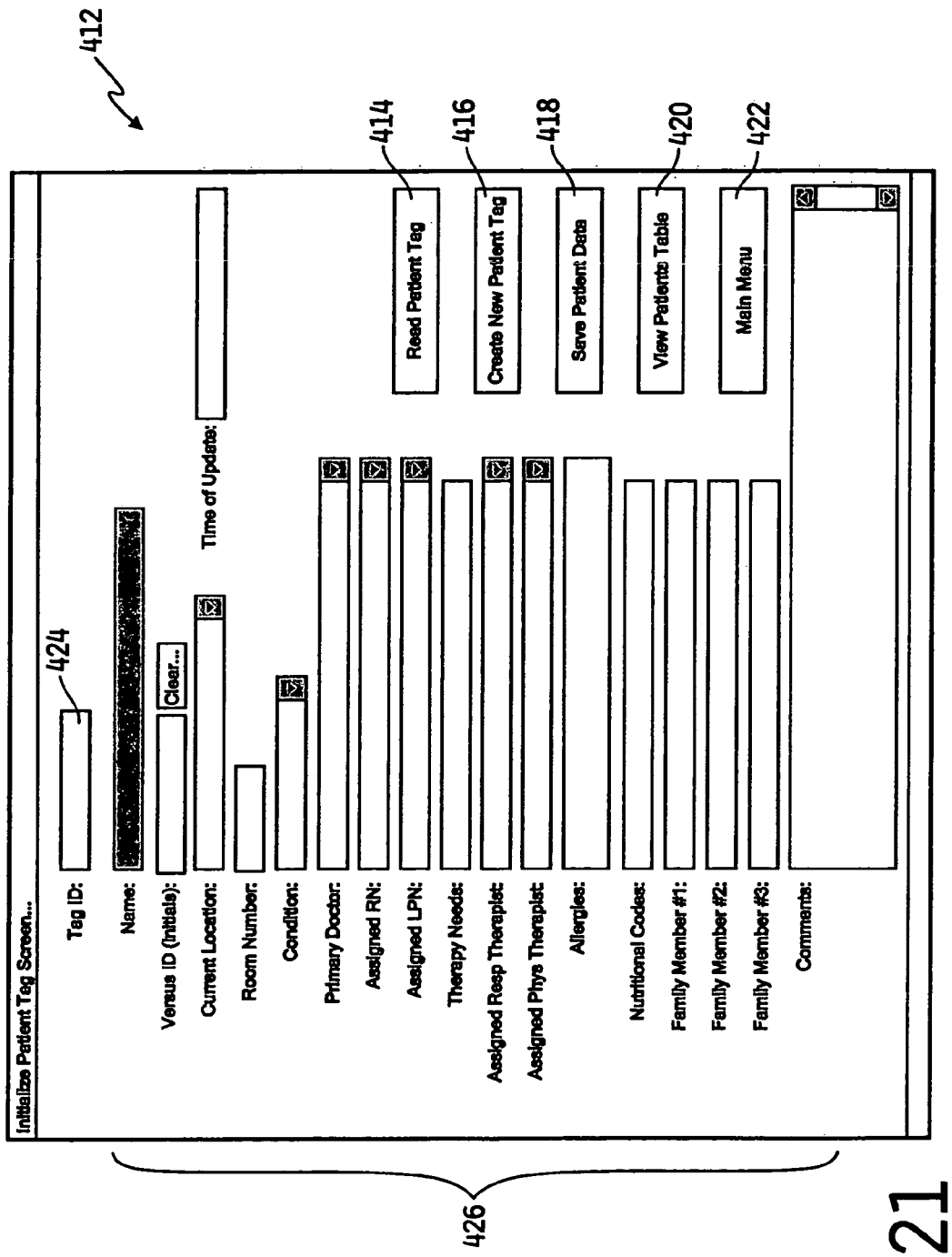
Figure 22:
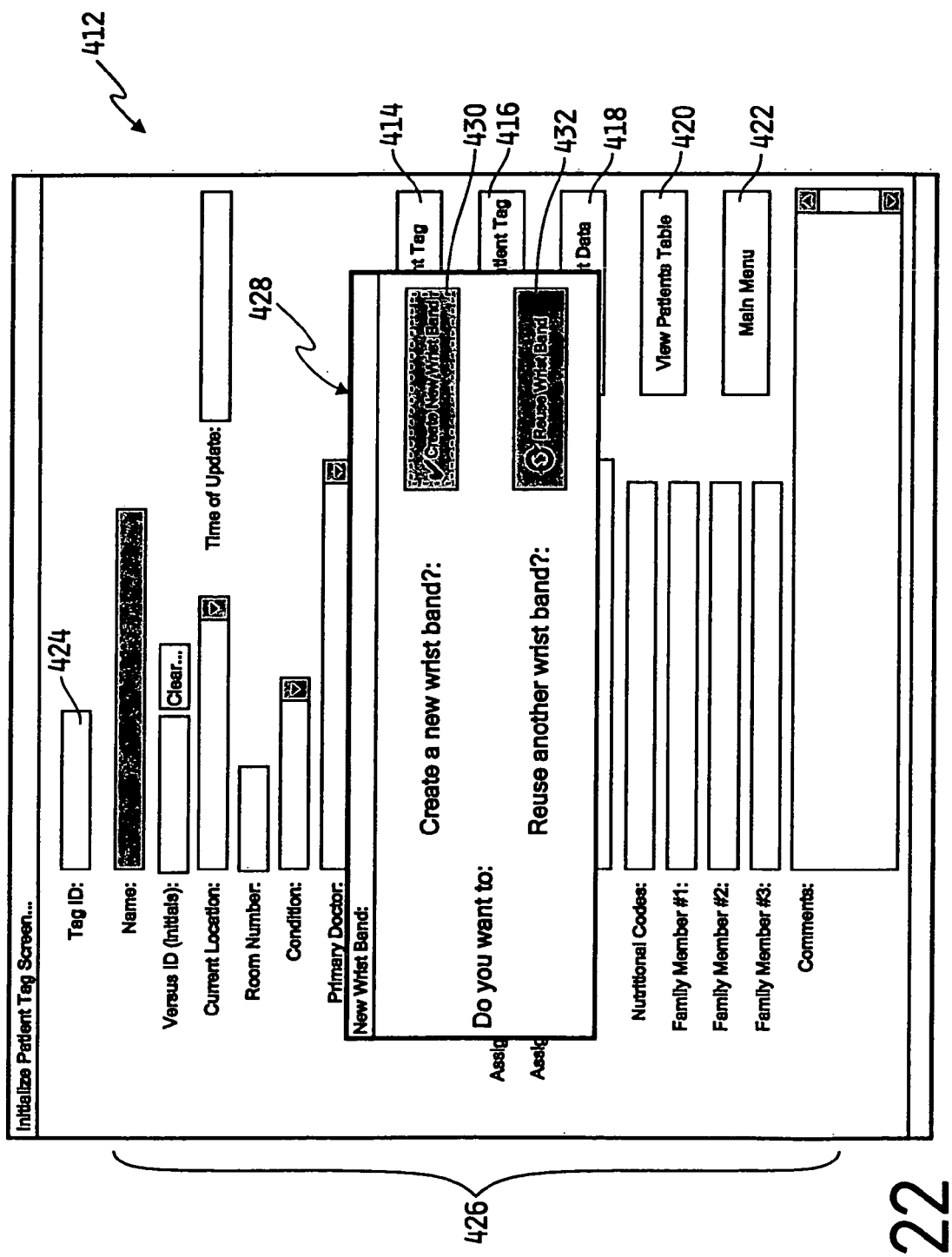

When a patient enters a facility for admission, an administrator operating workstation 28 may be begin the admission process by assigning an RFID tag 24 to the patient. The administrator may activate initialize patient tag button 402, which causes the software to generate screen 412 as shown in FIG. 21. Screen 412 includes a read patient tag button 414, a create new patient tag button 416, a save patient data button 418, a view patients table button 420, a main menu button 422, a tag ID field 424, and a plurality of other fields collectively designated 426 for containing information describing the patient and the patient's location, condition, physician, nurses, therapy needs, allergies, nutrition codes, family members, and any other data the administrator desires to associate with the patient in database 40 as described below. The administrator may next select an unused wristband containing and RFID tag 24 to be assigned to the patient. When the administrator activates create new patient tag button 416, a pop-up screen 428 is generated on screen 412 as shown in FIG. 22. Pop-up screen 428 includes a create new wristband button 430, and a reuse wristband button 432. Since RFID tags 24 contain memory that may be overwritten, reuse wrist band button 432 permits a tag ID of an RFID tag 24 to be reassociated with a different patient or asset. As will become apparent from the following description, reuse of a wristband would require generation of new written text to provide a visual indication of some of the information contained on the wristband RFID tag 24.

Figure 23:
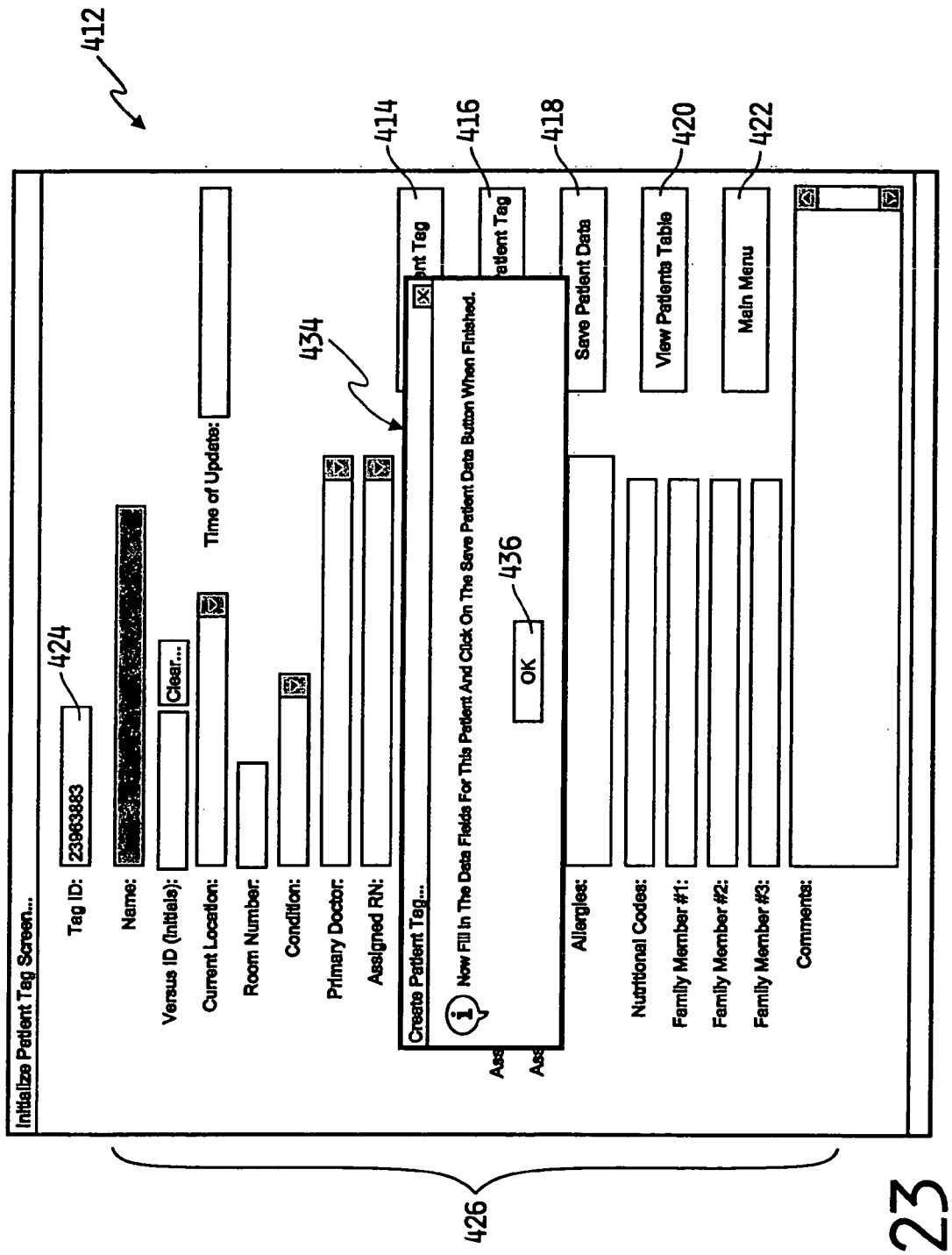

When the administrator activates create new wristband button 430, the software causes workstation 28 to communicate with RFID interface 30. RFID interface 30 then reads the RFID tag 24 of the new wristband to obtain the unique tag ID number stored in RFID tag 24. This number is provided by RFID interface 30 to workstation 28 which populates tag ID field 424 as shown in FIG. 23. Pop-up screen 428 (FIG. 22) is replaced in FIG. 23 with a prompt to the administrator in message box 434 to obtain additional information from the patient to populate fields 426. The administrator activates OK button 436 of message box 434 to begin the process of populating fields 426. The administrator manually enters information into fields 426 using an input device with workstation 424 such as a keyboard. When fields 426 are sufficiently populated, the administrator activates save patient data button 418 which causes workstation 28 to supply the information displayed on screen 412 to server 12 via network 14. Server 12 then stores the information in database 40, thereby associating all of the entered information with RFID tag 24. Additionally, RFID interface 30 prints appropriate textual information to be affixed to the wristband including RFID tag 24 and may write certain information to the memory of RFID tag 24. The textual information may include the patient's name, primary doctor, or any other information that may be useful to facility personnel that do not have access to database 40, or in the event that database 40 is for some reason inoperable. The information stored in the memory of RFID tag 24 may be information of critical importance to the facility personnel such as condition information, allergy information, current medications, etc. It is desirable to include certain information on the limited memory of RFID tag 24 in the event server 12 is for some reason inoperable.

Referring now to FIG. 24, activation of view patients table button 420 of screen 412 (FIG. 23) causes the software to generate screen 438. As shown, screen 438 includes an information area 440 presenting the contents of database 40 relating to current patients in tabular format. Scroll bars 442, 444 permit the administrator to view all of the generated information in a conventional manner.

Figure 25:
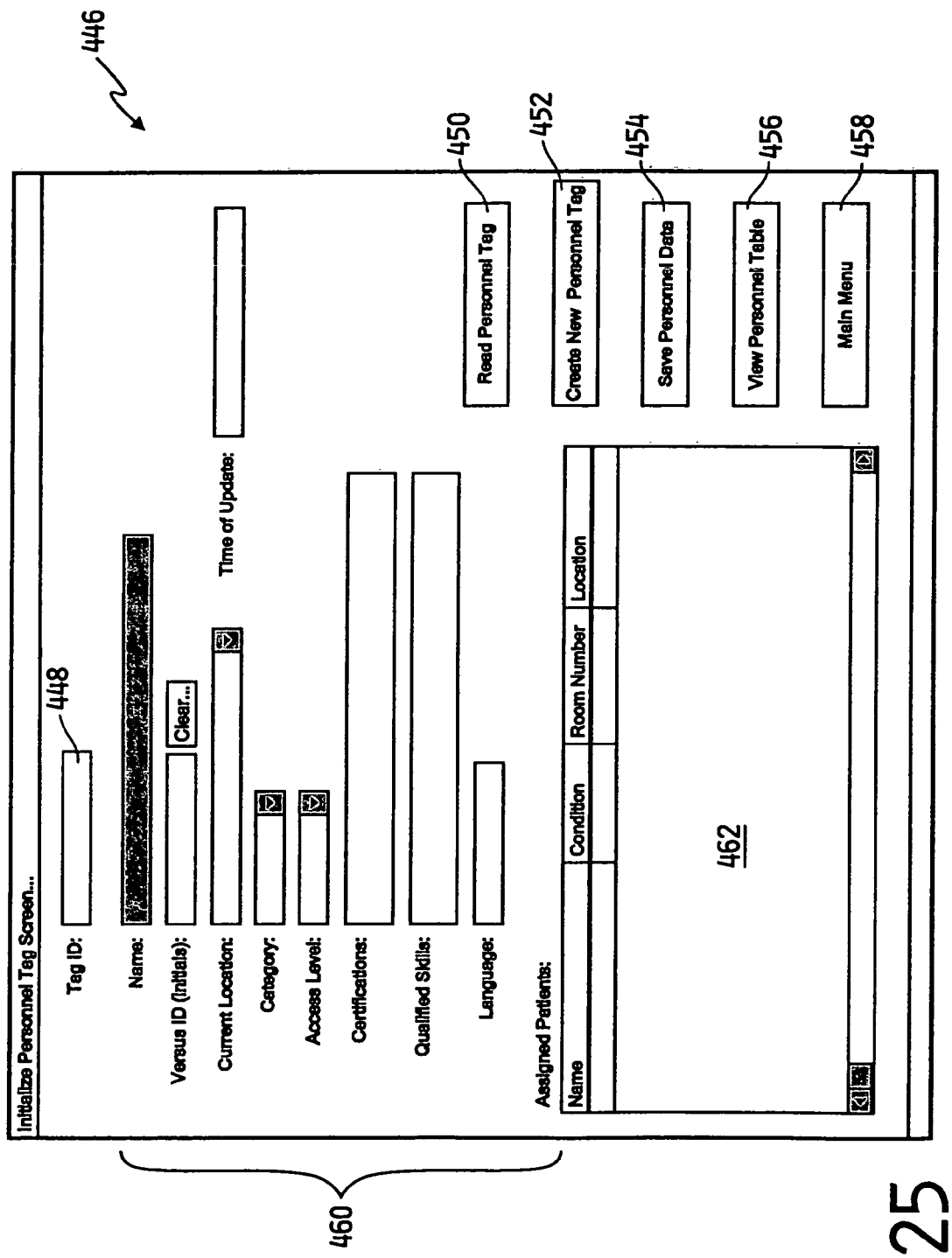

As indicated by main screen 400 of FIG. 20, a similar function is provided for initializing an RFID tag 24 for facility personnel. Specifically, by activating initialize personnel tag button 404 on screen 400, an administrator causes the software to generate screen 446 as shown in FIG. 25. Like screen 412 of FIG. 21, screen 446 includes a tag ID field 448, a read personnel tag button 450, a create new personnel tag button 452, a save personnel data button 454, a view personnel table button 456, and a main menu button 458. Additionally, screen 446 includes a plurality of other fields collectively designated 460 for receiving information describing the person for whom RFID tag 24 is being initiated. Finally, screen 446 includes an assigned patients field 462 for displaying the names, conditions, room numbers, and locations of patients assigned to the personnel member in the event that member is caregiver. At screen 446, the administrator may activate create new personnel tag button 452 to cause RFID interface 30 to read the unique tag ID of RFID tag 24 in the manner described above. The administrator then populates fields 460 and 462, and activates save personnel data button 454 to transfer the entered information to server 12 for storage in database 40, to cause RFID interface 30 to print information for the wrist band (or other selected form factor) containing RFID tag 24, and to write desired information to the memory of RFID tag 24 in the manner described above.

Figure 27:
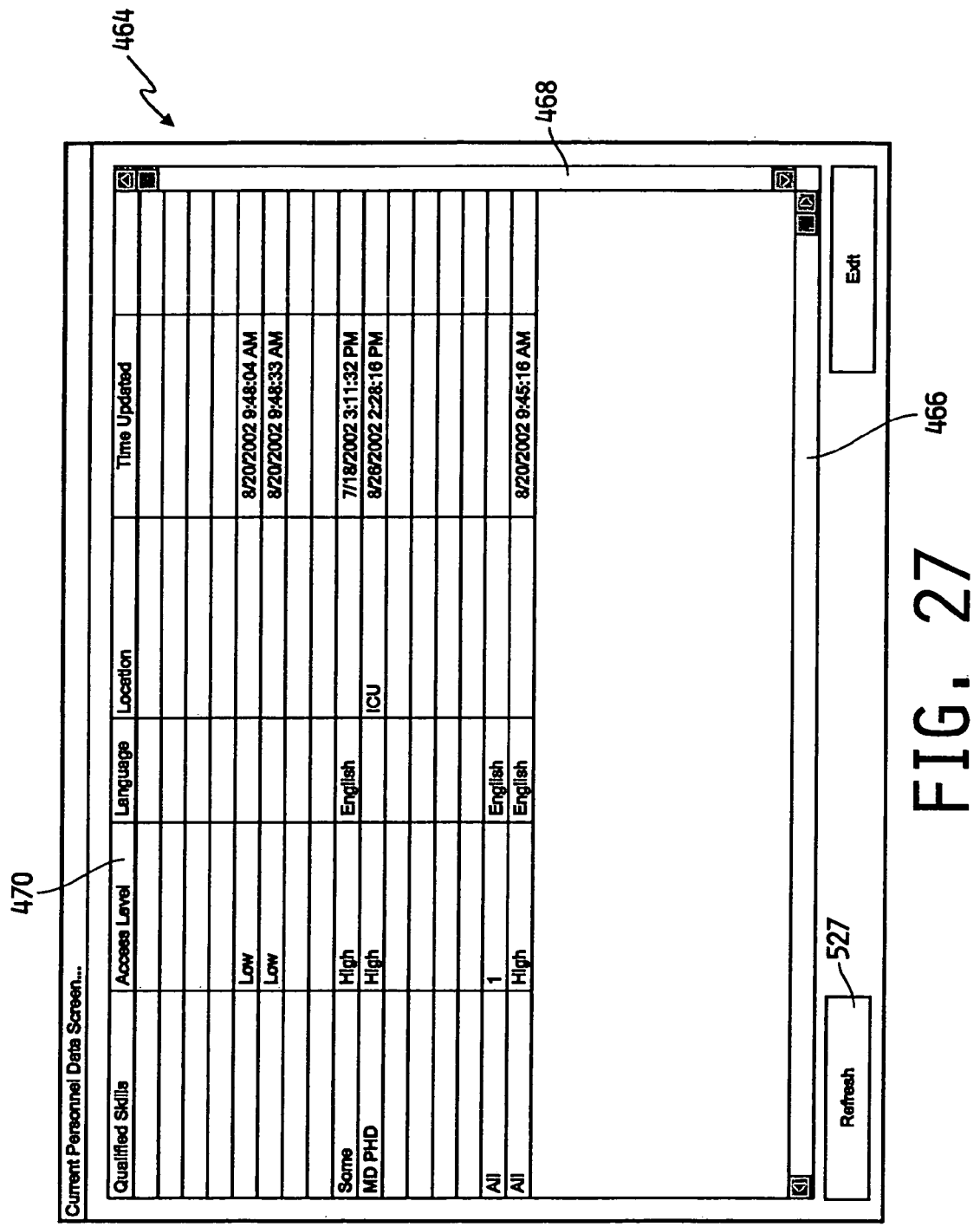

FIGS. 26 and 27 depict screen 464 which is generated upon activation of view personnel table button 456 of screen 446 (FIG. 25). Screen 464 provides the tag IDs of currently tagged personnel and all of the information associated with such tag IDs as stored in database 40 in tabular format. Scroll bars 466 and 468 permit navigation through the information in a conventional manner. It should be noted that in column 470 of FIG. 27, an access level is assigned by the administrator to each personnel member (see fields 460 of FIG. 25). System 10 may use this access level in any of a variety of different ways. For example, the access level may be stored in the memory of RFID tags 24 so that when a personnel member enters an area of the facility, transceivers 20 located in that area may automatically detect the access level of the individual personnel member and report that access level via network 14 to server 12. Logic software 38 of server 12 may then communicate with, for example, a room controller 168 in the area of the transceiver 20 that detected the personnel member. Room controller 168 may communicate with bed station 190 to mute entertainment equipment controlled by the bed electronics (not shown), disable lockout features of controls of bed 192, change the activated configuration of indicator light 170 to indicate the presence of, for example, a nurse having a medium access level, turn on a night light in the room or otherwise automatically configure the environment such that it corresponds with the anticipated needs of a personnel member having a particular access level. Of course, the same type of automatic configuration may be accomplished simply by detecting the unique tag ID associated with RFID tag 24 worn by the personnel member, accessing database 40 to determine the access level of the personnel member associated with that tag ID, and configuring the equipment and environment in the area according to that access level, or even according to the anticipated needs of the specific individual associated with the unique tag ID.

Figure 29:
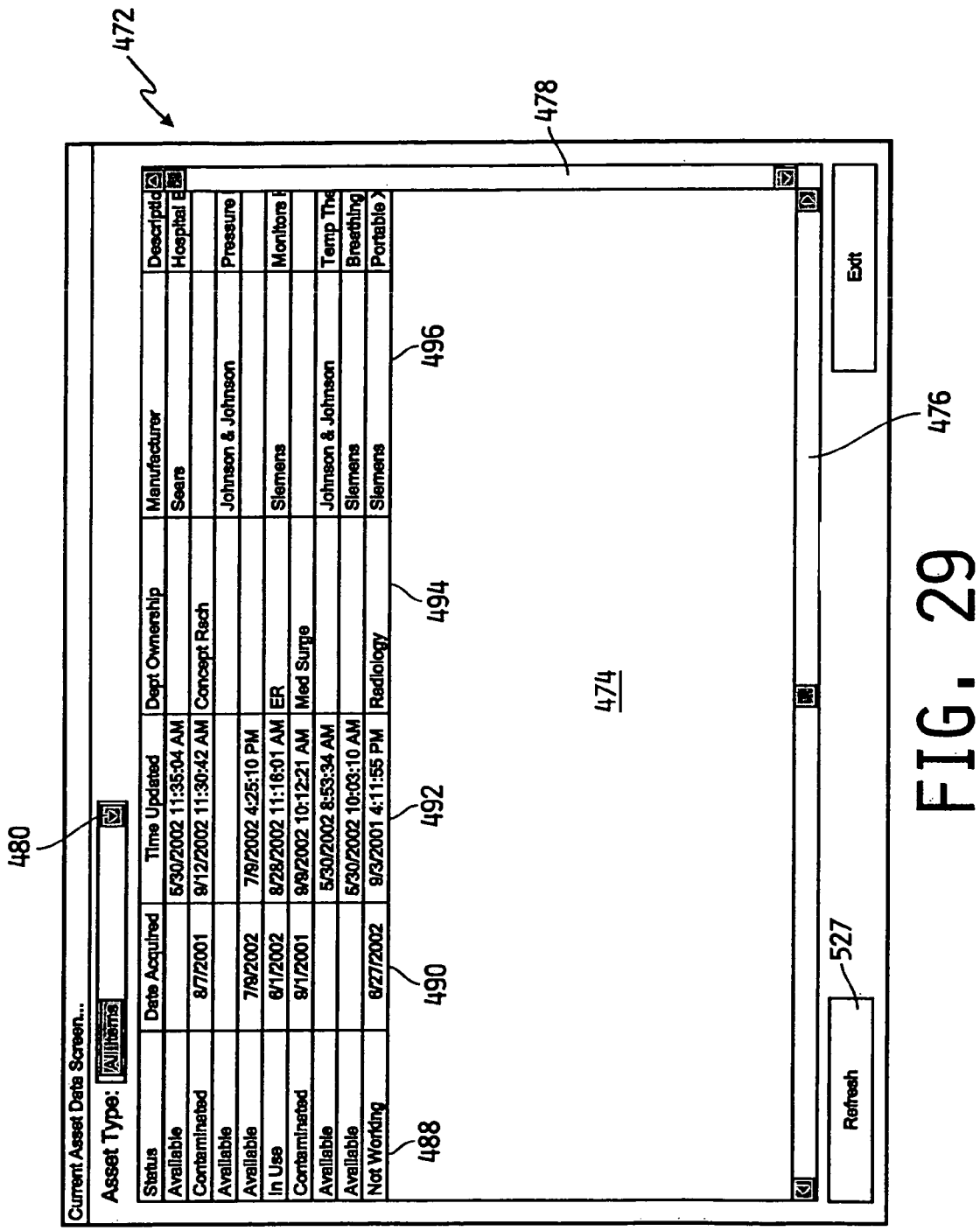
Figure 30:
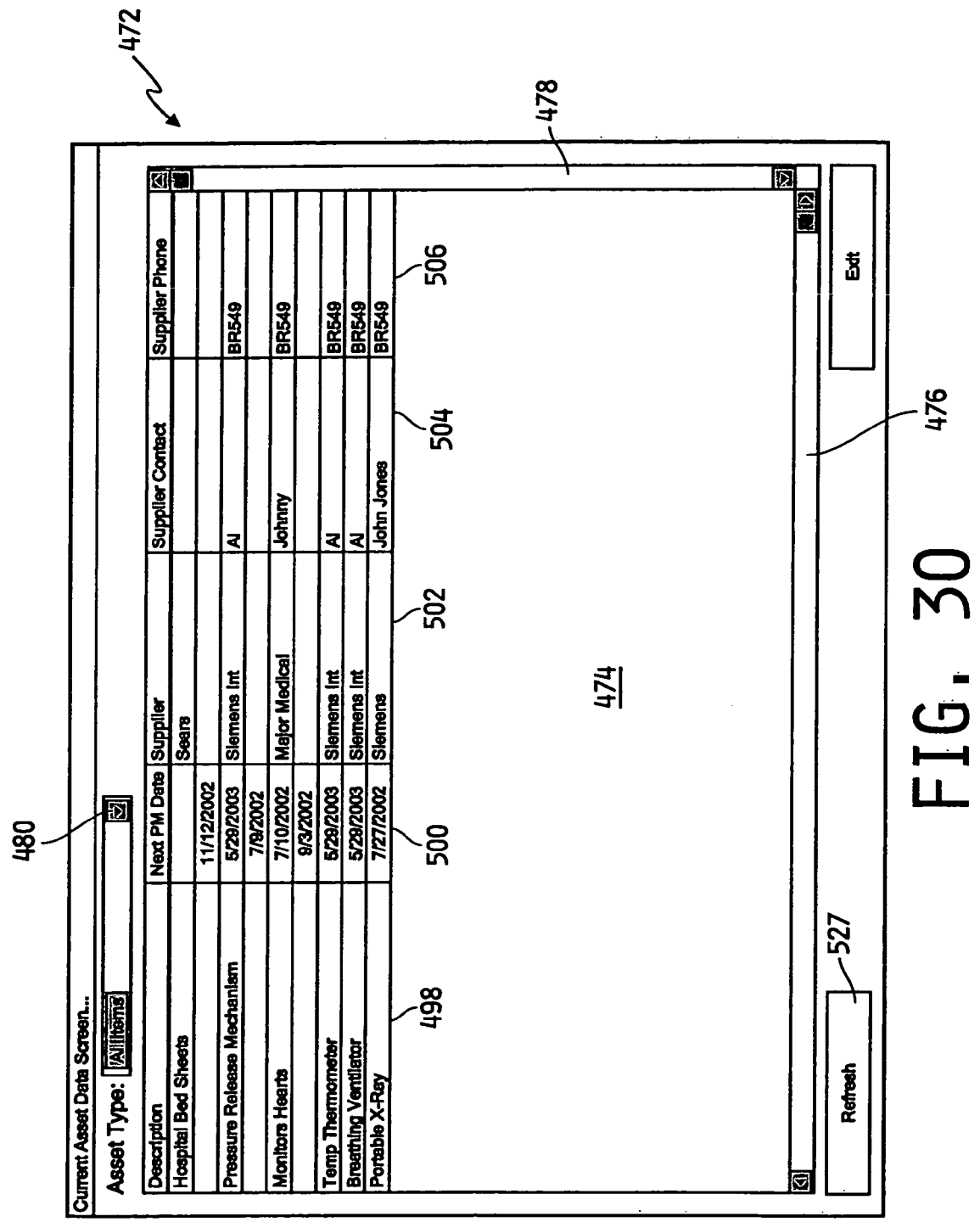

Activation of initialize asset tag button 406 of screen 400 (FIG. 20) generates screens similar to those described above for associating information with an asset such as a piece of equipment, medication, supplies, etc. Such screens include a view assets table button (not shown) that permits a user to obtain a tabular listing of all tagged assets as well as the information stored in database 40 associated with each of the assets as shown in FIGS. 28-30.

Figure 28:
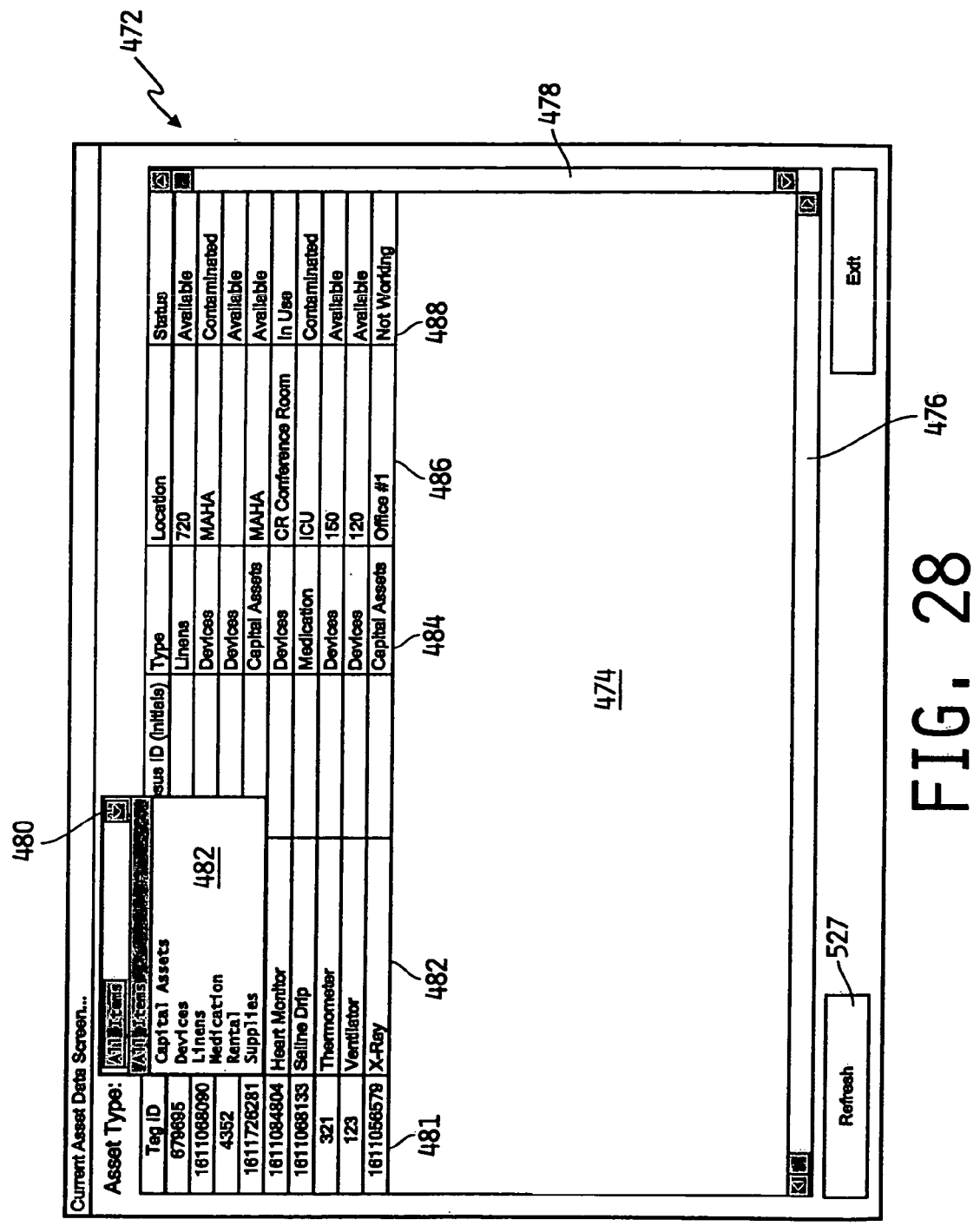

Referring to FIG. 28, current assets data screen 472 includes an asset description area 474, scroll bars 476, 478 and an asset type pull down menu button 480. Activation of asset type pull down menu button 480 generates a pull down menu 482 that lists all of the different types of assets described in database 40. Accordingly, a user can select a particular type of asset (such as medication). Once an asset type is selected, area 474 is populated with the tag IDs of the selected asset type as well as all of the other information generated during initiation of the various RFID tags 24 associated with the assets. As shown in FIGS. 28-30, area 474 includes a tag ID column 481, a description column 482, a type column 484, a location column 486, a status column 488, a date acquired column 490, a time updated column 492, a department ownership column 494, a manufacturer column 496, an additional description column 498, a preventative maintenance date column 500, a supplier column 502, a supplier contact column 504, and a supplier telephone column 506. As should be apparent from the foregoing, by accessing database 40 either via server 12, workstation 28, or client device 26, a user can quickly look-up the location and status of a particular asset. Additionally, any of the various entries on screen 472 may be linked via logic software 38 on server 12 to additional information. For example, a user could select or click on a particular asset or the supplier name for a particular asset and cause server 12 to connect the user through network 36 to the supplier's website. Alternatively, files may be stored on server 12 including schematics, flow diagrams, user's manuals, and other technical information associated with a particular asset. By clicking on an appropriate field in screen 472, the user may access one or more such files to obtain additional information regarding the selected asset.

As will become apparent from the following description, as an asset having an RFID tag 24 is moved within the facility, transceivers 20 may detect the location of the asset and transmit updated location information via network 14 to server 12 for storage in database 40, thereby updating information displayed in location column 486 of screen 472. Additionally, as an asset is moved into and out of contaminated areas within the facility (as identified in database 40), logic software 38 of server 12 may determine that the asset is contaminated and update status column 488 accordingly. Alternatively, personnel may write to an RFID tag 24 associated with a particular asset using client device 26 to change the contents of the memory of RFID tag 24 to indicate the contaminated status of the asset. In that instance, as transceivers 20 read the tag ID from RFID tag 24, transceivers 20 will also obtain status information (and any other information stored in the memory of RFID tag 24) and provide that information to server 12 for storage in database 40. Moreover, each time an asset undergoes scheduled maintenance, another portion of the memory of RFID tag 24 associated with the asset may be written to using client device 26 or other RFID interface to update the preventative maintenance information stored in RFID tag 24. As the data from the memory of RFID tag 24 is read by transceivers 20, the updated preventative maintenance date is provided to server 12 via network 14 for storage in database 40. Server 12 may be configured to update column 500 based on a predetermined preventative maintenance schedule corresponding to the asset.

Figure 31:
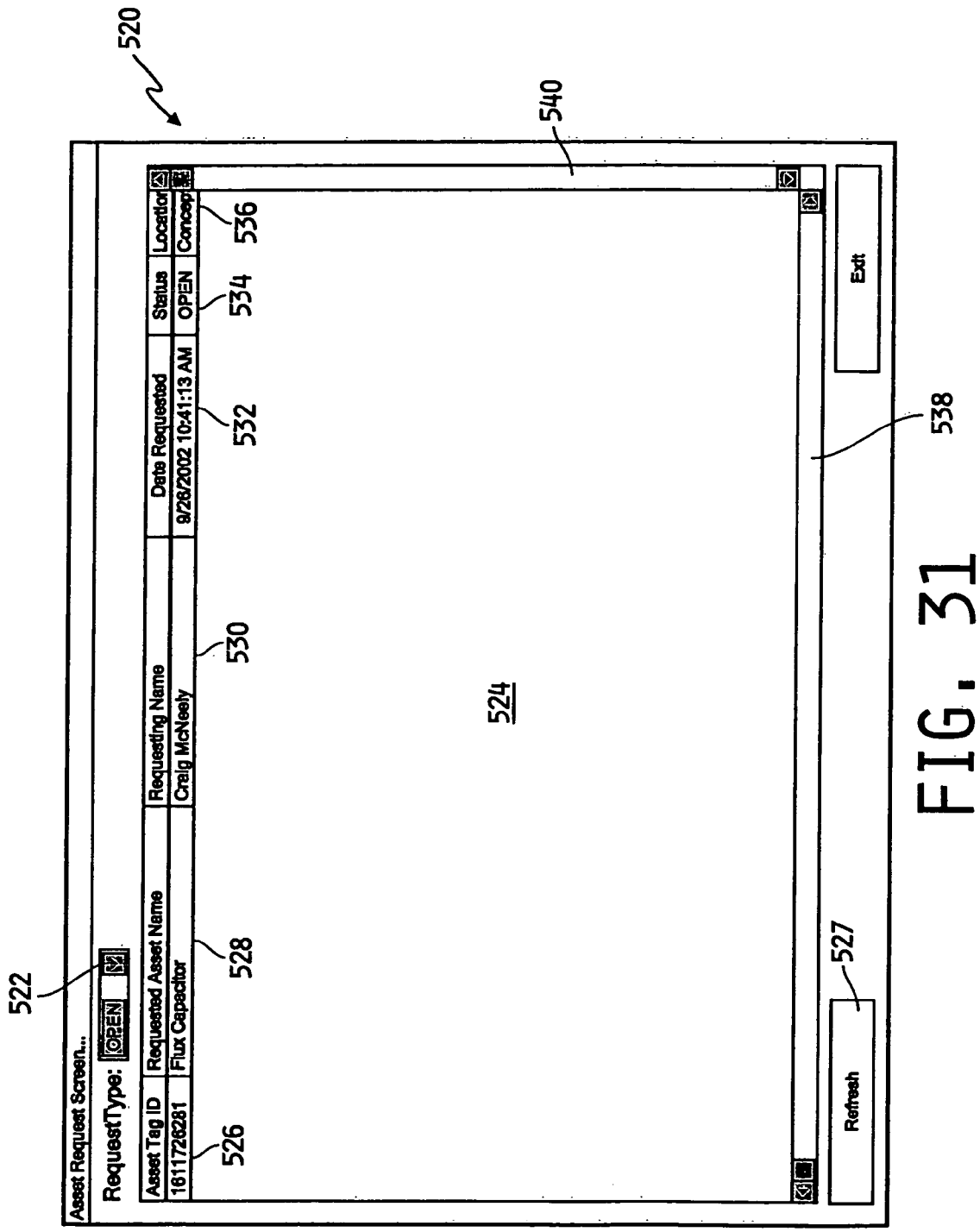

As is further described below, users of client devices 26 (or any other device providing access to server 12) may, in one embodiment of the invention, request assets by submitting requests to server 12. Personnel responsible for delivering assets such as equipment and supplies may be provided access to the RFID software described herein. Upon activation of the view requested assets button 408 of screen 400 (FIG. 20), the user will be presented with screen 520 as shown in FIG. 31. Screen 520 includes a request type drop down menu button 522, which permits the user to select one of either open asset requests or issued asset requests in a conventional manner. As shown in FIG. 31, open asset requests are displayed to the user in area 524. Area 524 includes an asset tag ID column 526, a requested asset name column 528, a requesting name column 530, a date requested column 532, a status column 534, and a location column 536. Area 524 also includes scroll bars 538, 540. The user responsible for delivering assets may receive a message, for example, on client device 26 over network 16 as initiated by server 12 in response to an asset request. The message may be an e-mail message, an audible message, or some other type of notification that an asset request has been posted to system 10. The person responsible for delivering assets may check the current location of the asset (as reflected in area 524 and stored in database 40), retrieve the asset, and deliver it to the requesting person at the location designated in the asset request.

Figure 32:
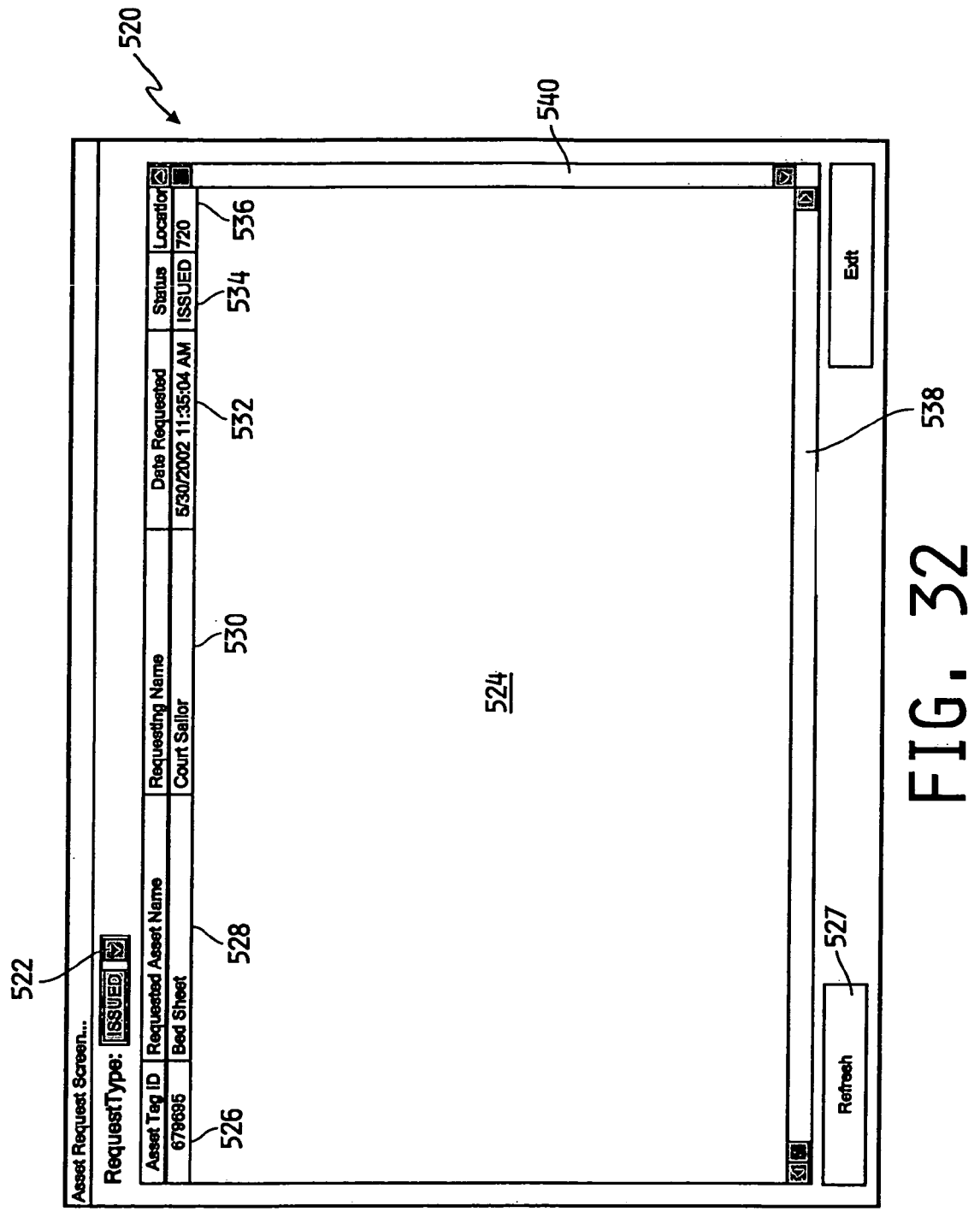

FIG. 32 is identical to FIG. 31, except that area 524 displays information regarding issued assets as selected using asset type drop down button 522.

Figure 33:
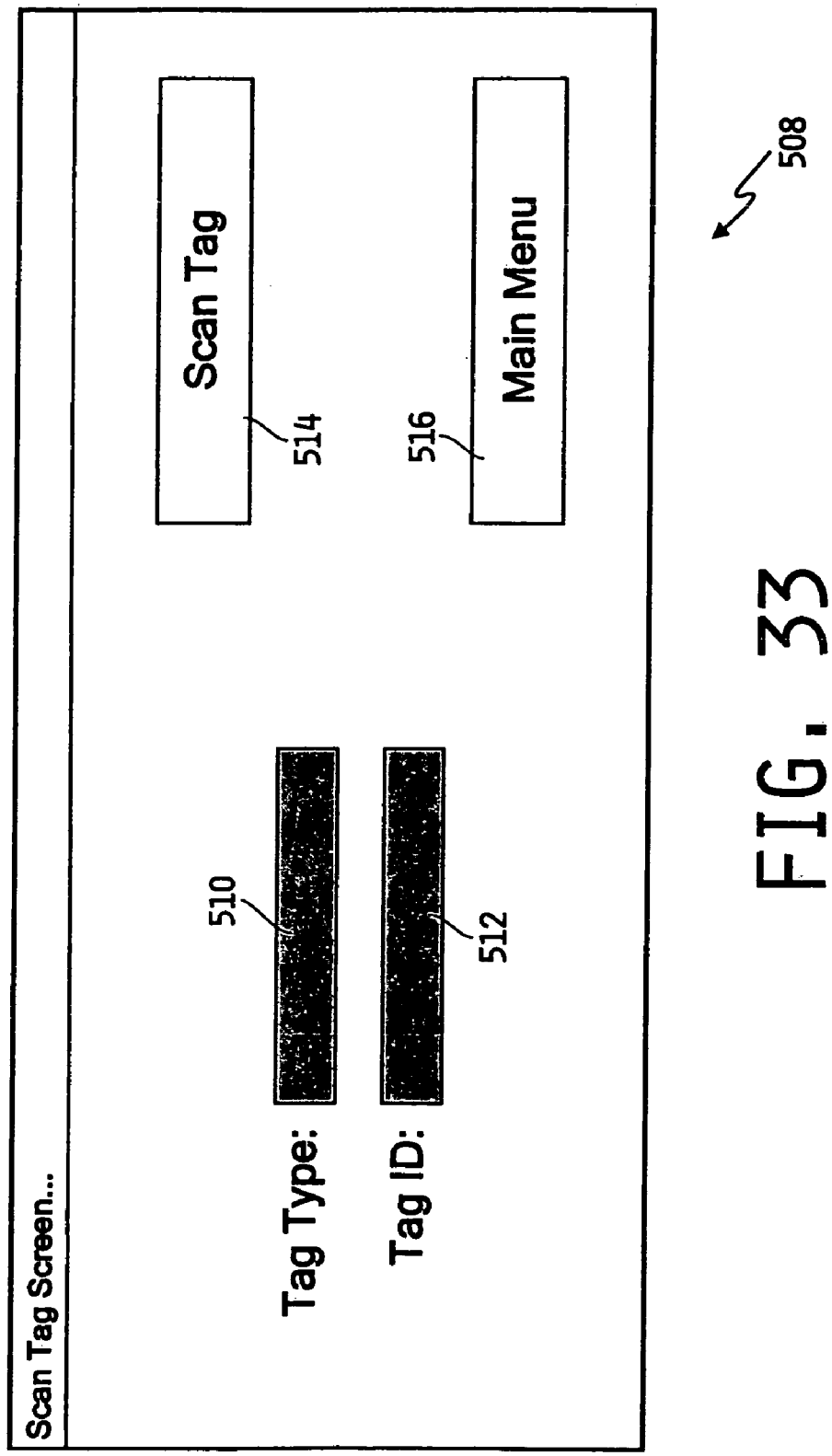

Finally, when an administrator activates scan tag type and ID button 410 on screen 400 (FIG. 20), a screen 508 is generated on display 27 of client device 26 as shown in FIG. 33. Scan tag screen 508 includes a tag type field 510, a tag ID field 512, a scan tag button 514, and a main menu button 516. The administrator or other facility personnel may place an unidentified tag near an RFID reader such as RFID interface 30, 42, and activate scan tag button 514. The RFID reader will read the tag type and tag ID information from the RFID tag 24. The tag type information denotes a particular category of RFID tags as is will known in the art.

It should also be noted that the various patient, personnel, and asset data screens described above (e.g., FIGS. 24, 26-32) include a refresh button 527. Refresh button 527 may be activated at any time while the RFID software is active to cause workstation 28 to access database 40 and update the displayed information with any changes that have occurred since the user last accessed database 40. Of course, system 10 could readily be configured to automatically update the displayed information any time a relevant change is made to the information stored in database 40.

Figure 34:
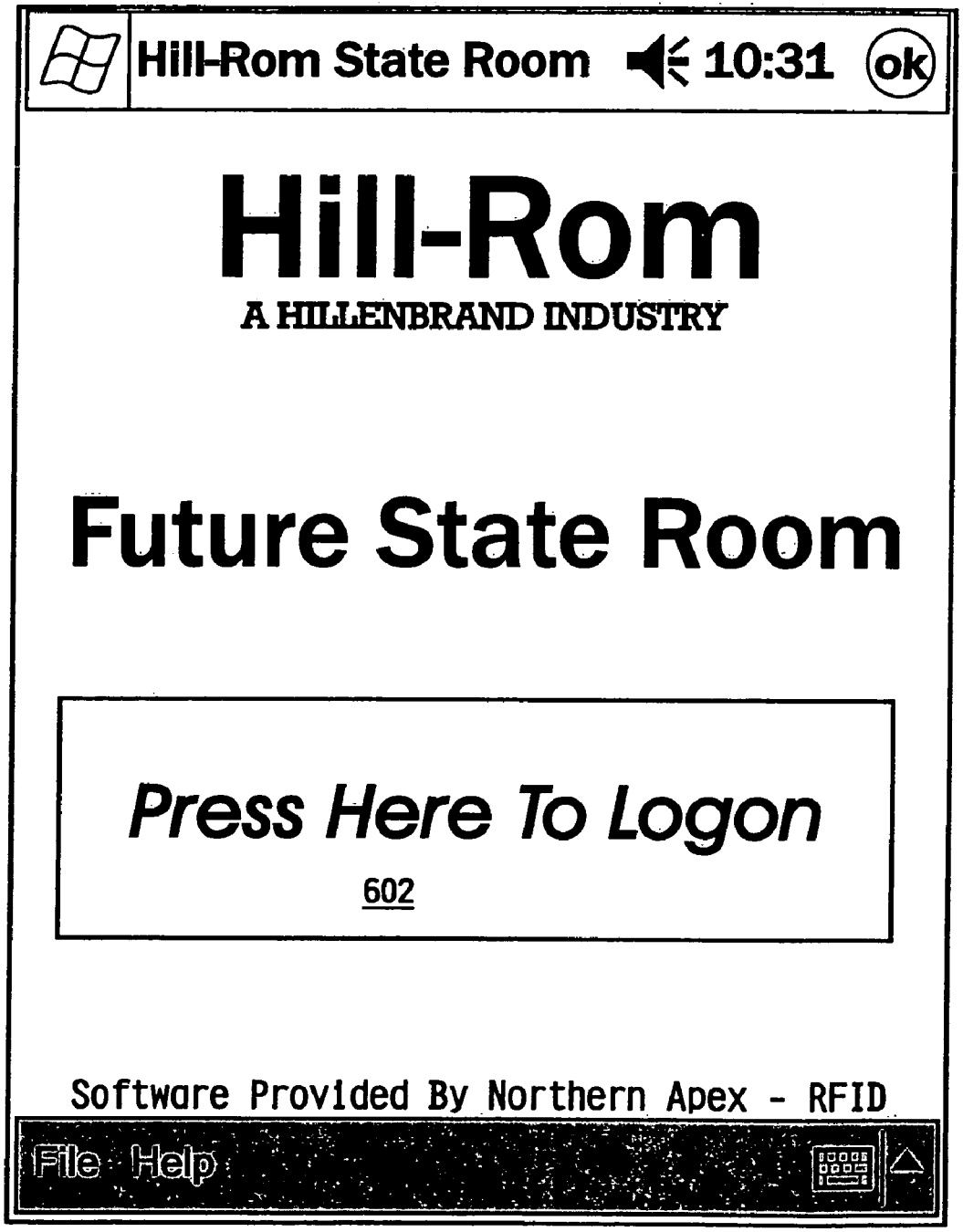

FIGS. 34-43 depict screens generated on client device 26 as part of RFID application software executed by client device 26. Upon activating the RFID software, screen 600 is generated on display 27 of client device 26 as shown in FIG. 34. The user activates log in area 602 and scans his or her RFID tag 24 using RFID interface 42 of client device 26. RFID interface 42 reads the unique ID from RFID tag 24, and client device 26 transmits that ID via network 16 to server 12. Server 12 accesses database 40 to determine the identity of the person associated with the read RFID tag 24. Once the person is identified, server 12 communicates back to client device 26 via network 16 information corresponding to the name (and any other configuration information such as access rights, etc.). Client device 26 responds by generating screen 604 shown in FIG. 35. Screen 604 is the RFID software main screen and includes current user field 606, current patient info button 608, current personnel info button 610, asset tag data button 612, equipment request button 614, nurse call module button 616, and scan tag button 618.

From main screen 604, the user may scan an RFID tag 24 associated with an asset or generate a request for equipment. Assuming the user scans an RFID tag 24 associated with a patient, the user places RFID interface 42 near RFID tag 24 and activates scan tag button 618. Client device 26 then generates screen 620 as shown in FIG. 36. Client device 26 generates screen 620 by receiving the unique identification number of RFID tag 24 from RFID interface 42, transmitting that identifier via network 16 to server 12, and receiving the information associated with that ID in database 40 from server 12 via network 16. That information is then displayed in the various fields shown in screen 620. As shown, screen 620 includes a name field 622, a room field 624, a location field 626, a condition field 628, and a plurality of other fields collectively designated 630. Screen 620 further includes a post-updates button 632, a next page button 634, and an exit button 636. Any of the fields 626, 628, 630 including drop down buttons 638 may be changed by the user of client device 26. Specifically, a physician using client device 26 may activate drop down button 638 associated with field 628 and update the patient's condition from stable to, for example, critical. When a physician makes such a change, the physician activates the post-updates button 632 which causes client device 26 to send the updated information via network 16 to server 12 for storage in database 40. Additionally, if the changed data is stored on the memory of RFID tag 24 associated with the patient's wristband, the physician may write the updated information to RFID tag 24 while simultaneously transmitting it via network 16 to server 12. In yet another alternative, the physician may simply write updated data to the patient's wristband. That data is then received by transceivers 20 and transmitted to server 12 via network 16. Activation of the exit button 636 on screen 620 returns the user to screen 604 of FIG. 35. Activation of the next page button 634 causes client device 26 to generate screen 640 as shown in FIG. 37. Screen 640 includes further fields collectively designated 642 for containing additional information as shown related to the patient associated with RFID tag 24 scanned by the user. Screen 640 further includes a previous page button 644, activation of which causes client device 26 to return the user to screen 620 of FIG. 36.

Figure 35:
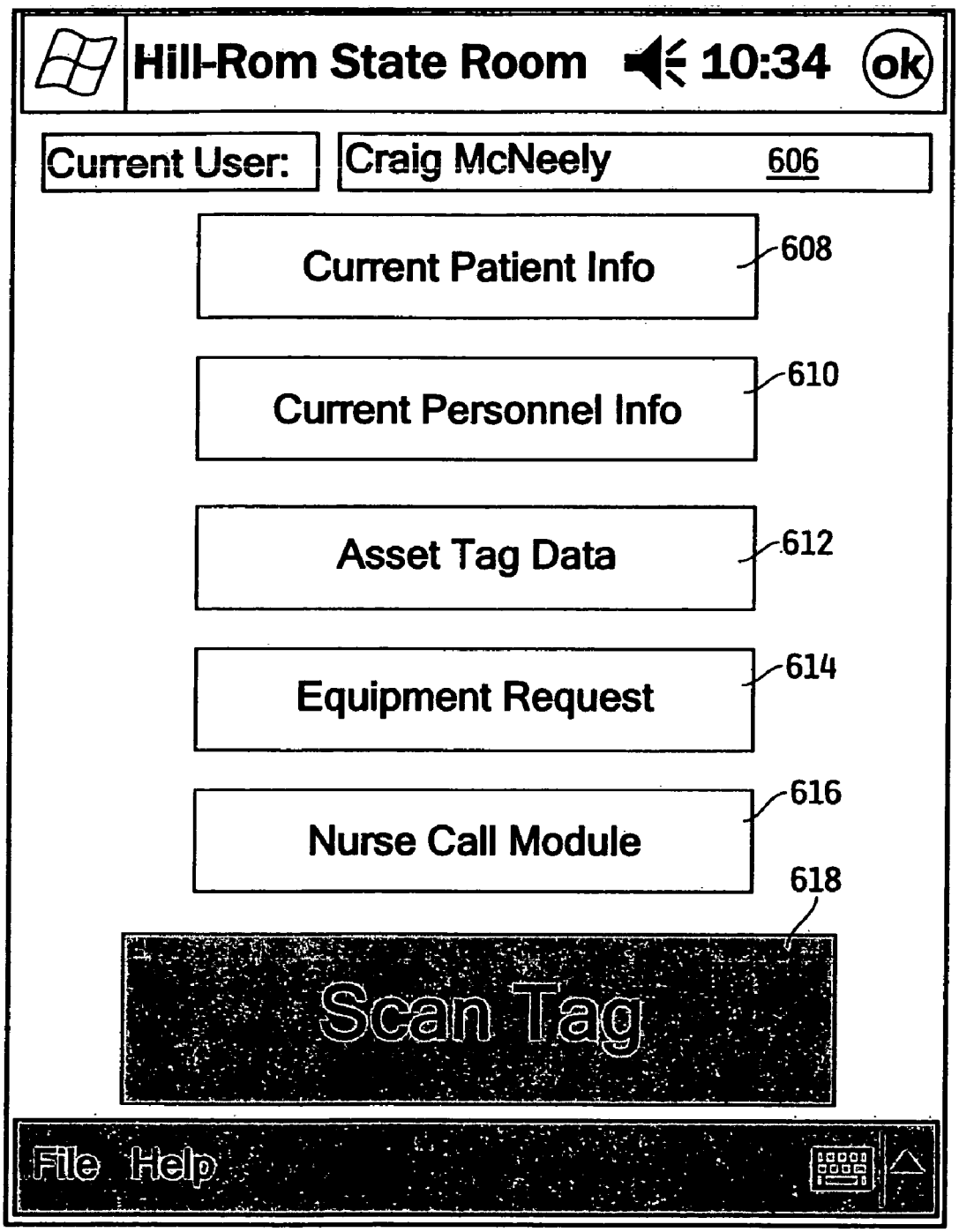
Figure 36:
Figure 38:
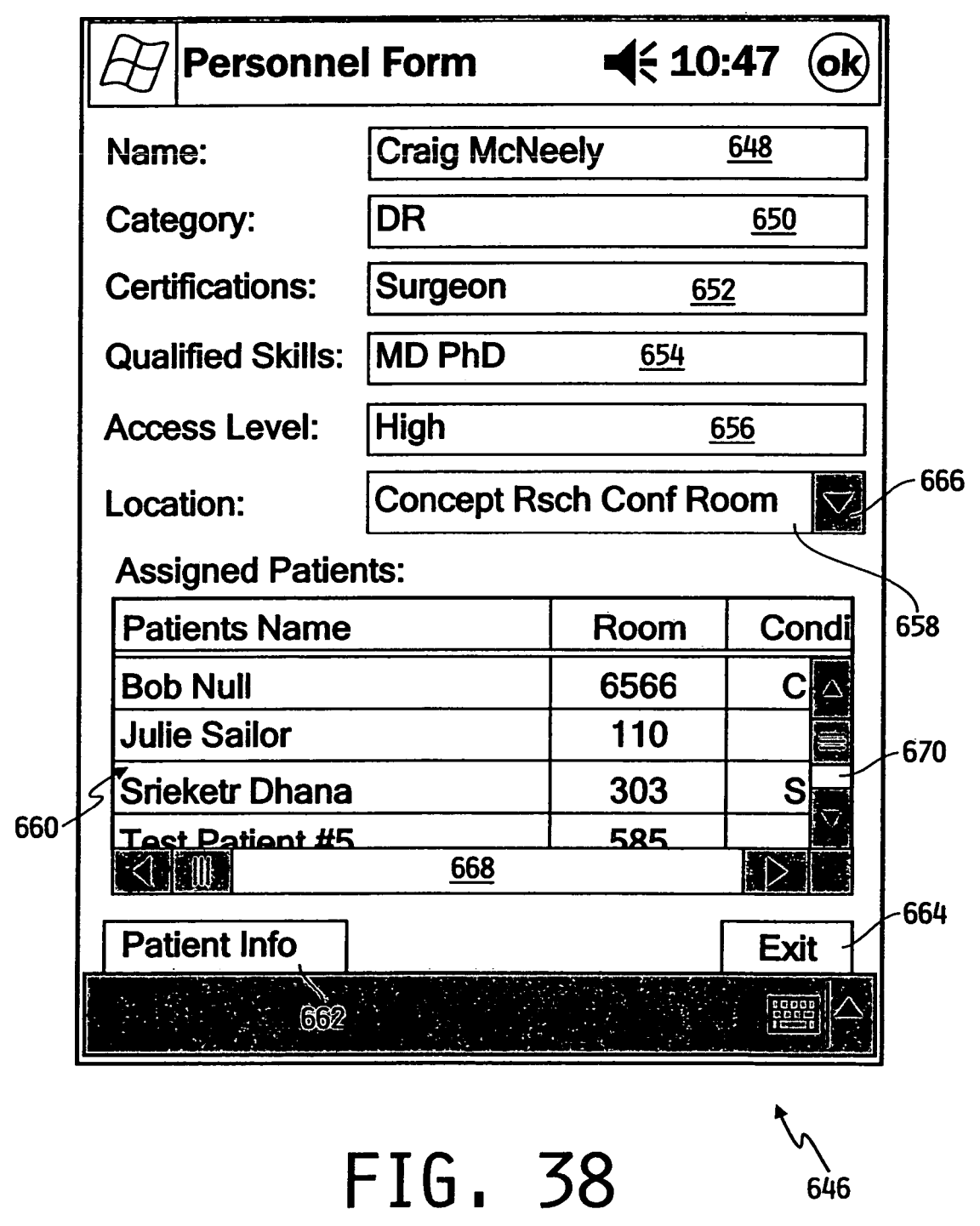

In the event the user scans an RFID tag 24 associated with facility personnel, such as a physician's identification badge, and activates scan tag button 618 of FIG. 35, client device 26 generates screen 646 as shown in FIG. 38. Screen 646 includes a name field 648, a category field 650, a certifications field 652, a qualified skills field 654, an access level field 656, a location field 658, an assigned patient's information area 660, a patient info button 662, and an exit button 664. When the user scans RFID tag 24 associated with the facility personnel member, RFID interface 42 reads the identification number associated with RFID tag 24, and provides that information to client device 26, which transmits the identification number via network 16 to server 12. Server 12 accesses information in database 40 associated with the identification number and transmits that information via network 16 back to client device 26 for populating the various fields shown in screen 646. As shown, location field 658 includes a drop down button 666 which permits the user to change his or her present location by selecting a different location from the drop down menu (not shown) in the manner described above.

Area 660 includes information about the various patients assigned to, in this example, the physician, Craig McNeely. The patient information is presented in tabular format which may be navigated using scroll bars 668, 670. The user may highlight a particular patient's name and activate the patient info button 662 to receive information about the patient. Specifically, activation of the patient info button 662 may cause client device 26 to transmit a patient information request via network 16 to server 12. Server 12 would respond to such a request by obtaining additional information relating to the selected patient from database 40, and transmitting that information via network 16 back to client device 26.

It should be noted at this point that if the user activates the exit button 664 shown in FIG. 38, client device 26 will respond by generating screen 604 of FIG. 35. Assuming the user had previously scanned an RFID tag 24 associated with a patient as described above, the user could then activate current patient info button 608 to return to screens 620, 640. In other words, client device 26 retains the information obtained in association with the last RFID tag 24 in each of the three categories (patient, personnel, and asset) scanned by RFID interface 42. The user could also activate current personnel info button 610 and return to screen 646 of FIG. 38.

Figure 39:
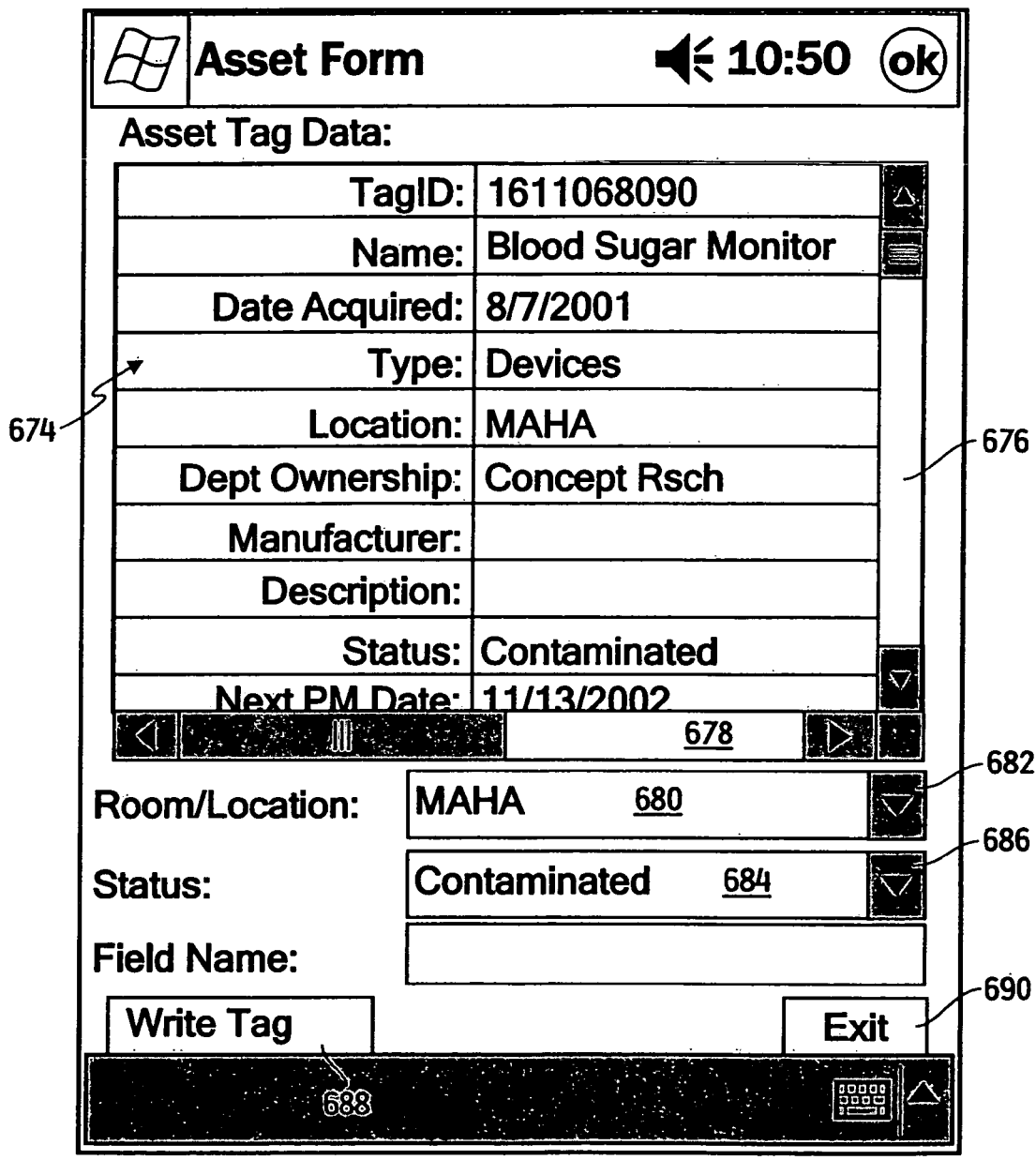
Figure 40:
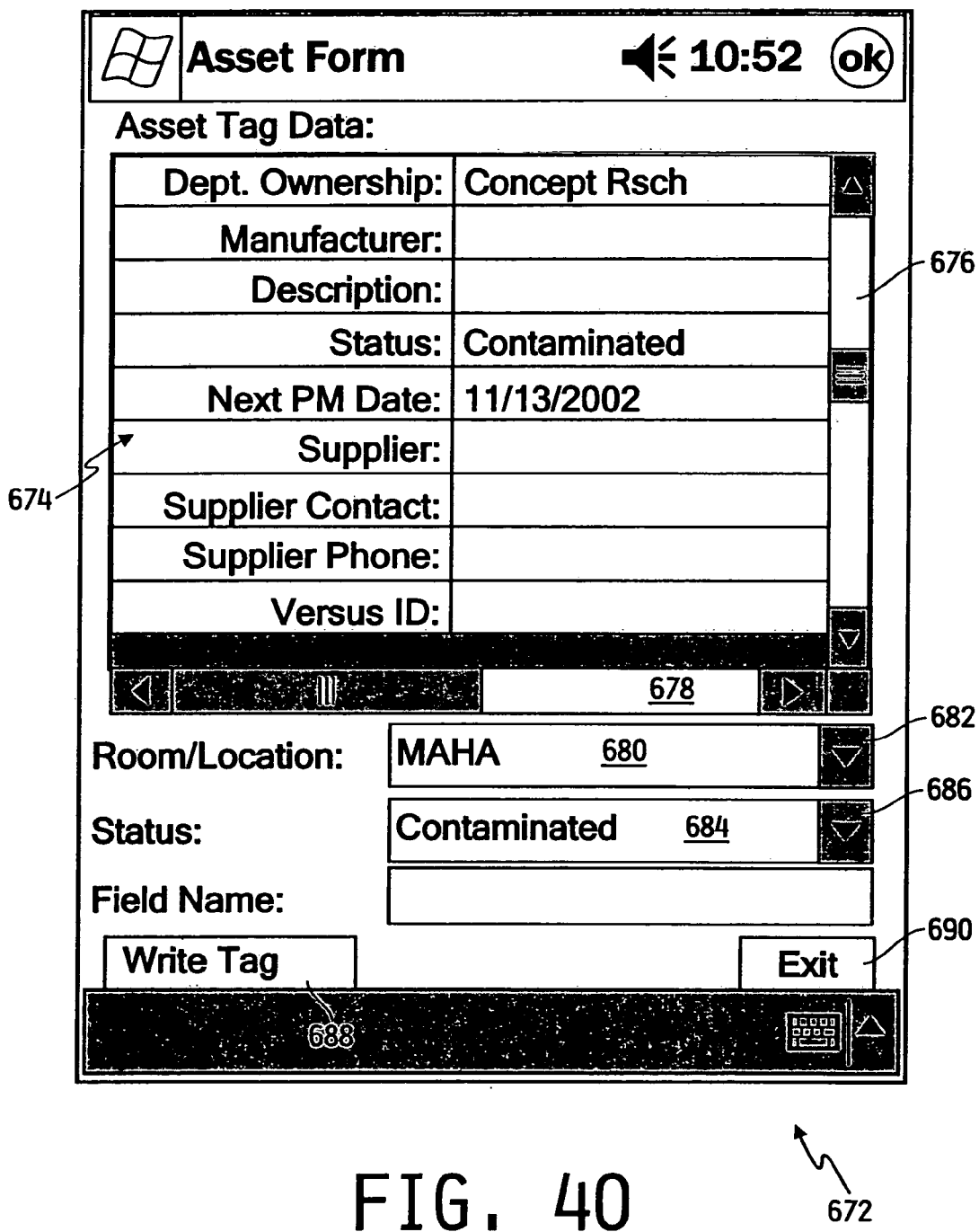

If the user scans an RFID tag 24 associated an asset (e.g., a piece of equipment) by placing RFID interface 42 adjacent RFID tag 24 and activating scan tag button 618 of FIG. 35, client device 26 generates screen 672 of FIG. 39 by reading the unique identification number from RFID tag 24, transmitting the number to server 12, and receiving information associated with the number from server 12 as stored in database 40 and described above. Screen 672 includes an asset information area 674 having scroll bars 676, 678, a room/location field 680 having a drop down button 682, a status field 684 having a drop down button 686, a write tag button 688, and an exit button 690. As shown, a plurality of different types of information associated with the scanned asset and stored in database 40 are displayed in area 674 of screen 672. As indicated above, client device 26 may readily be configured such that one or more of the various fields contained in area 674 are linked to additional information. For example, links may be provided to schematics, users manuals, manufacturer websites, and any other desired source of information that may be stored in database 40 of server 12 or accessible via network 34 or network 36. FIG. 40 is similar to FIG. 39, except that scroll bar 676 has been moved to display additional information about the scanned asset in area 674.

Figure 41:
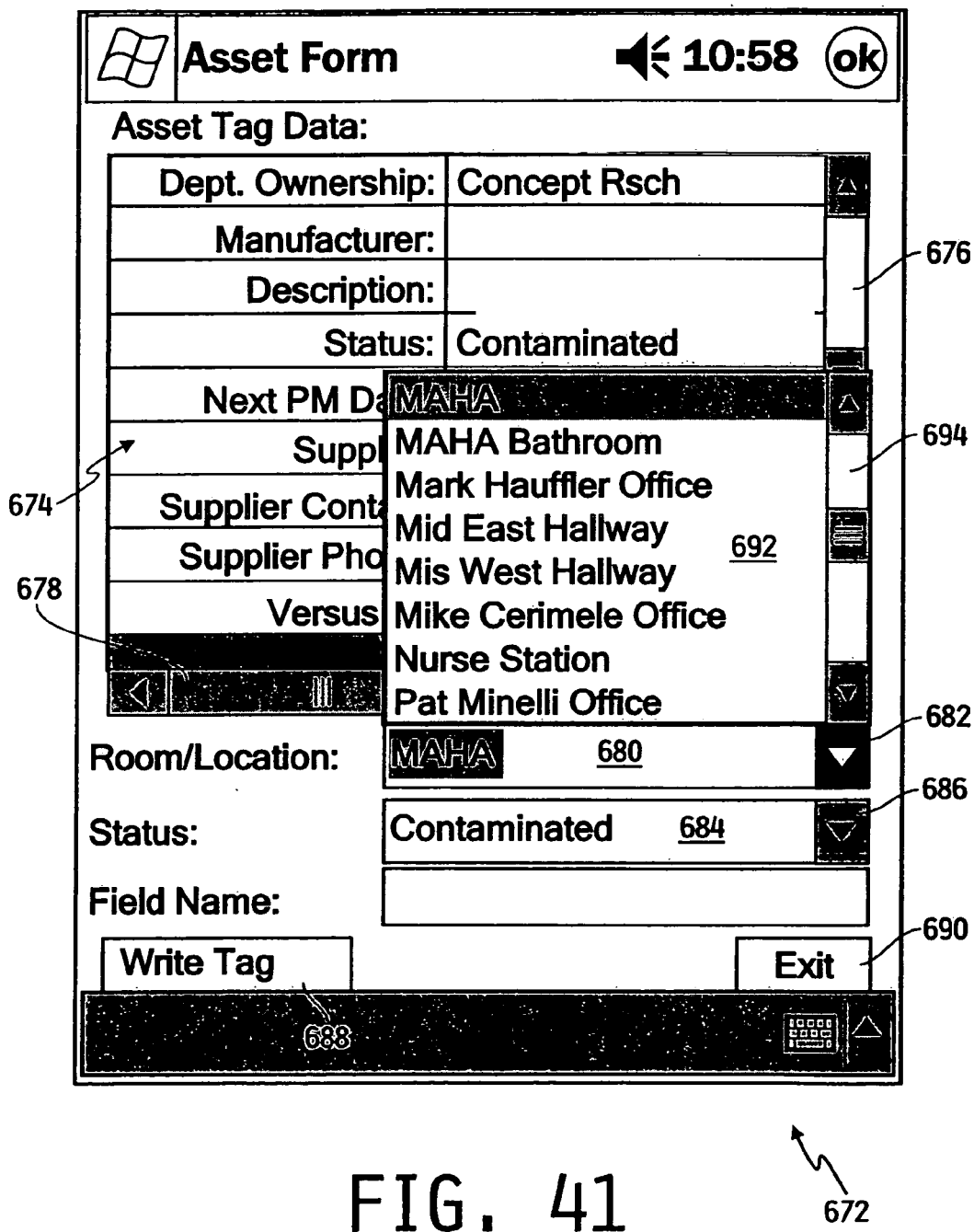

Referring now to FIG. 41, screen 672 is shown with drop down button 682 activated. A user may activate drop down button 682 to obtain options for different locations for the scanned asset. For example, if a user desires to move a blood sugar monitor from one location to another, the user may activate drop down button 682, highlight a desired destination location by scrolling through the various locations displayed in area 692 using scroll bar 694, and activating write tag button 688. By activating write tag button 688, the user causes client device 26 to either write new location information to the RFID tag 24 associated with the asset, transmit the new location information to server 12 via network 16 for updating in database 40, or both as described above. Similarly, the user may update the status of the asset by activating drop down button 686 and selecting from the various status options (not shown). For example, after an asset has been cleaned, the personnel member cleaning the asset may update the asset's status from contaminated to available. Since this information will reside in database 40, anyone accessing database 40 via system 10 can determine that the cleaned asset is now available for use. The user may return to screen 604 of FIG. 35 by activating exit button 690. At that point, the user may toggle between the latest scanned information associated with a patient, personnel member, or an asset, by activating buttons 608, 610, 612, respectively.

Figure 42:
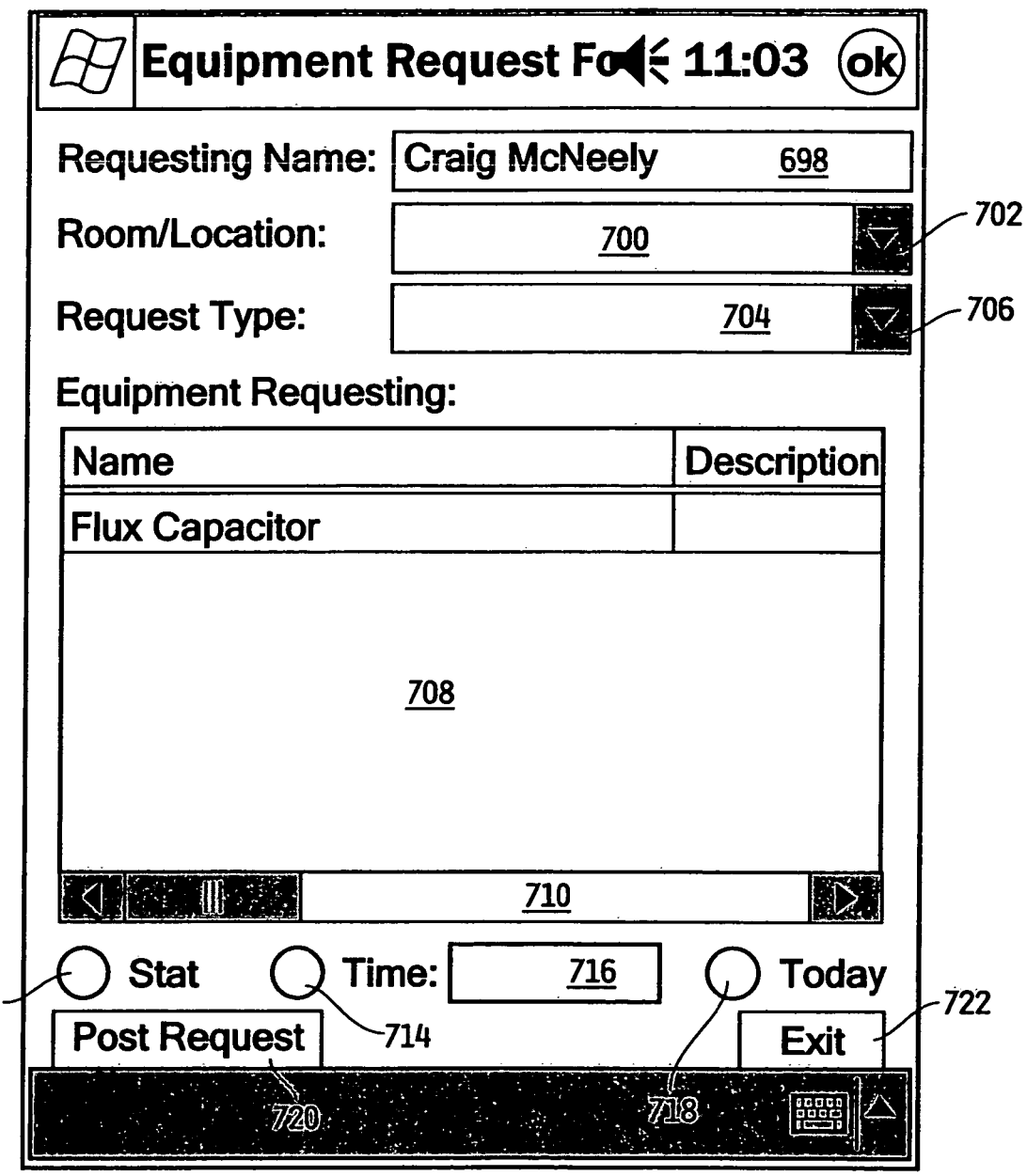
Figure 43:
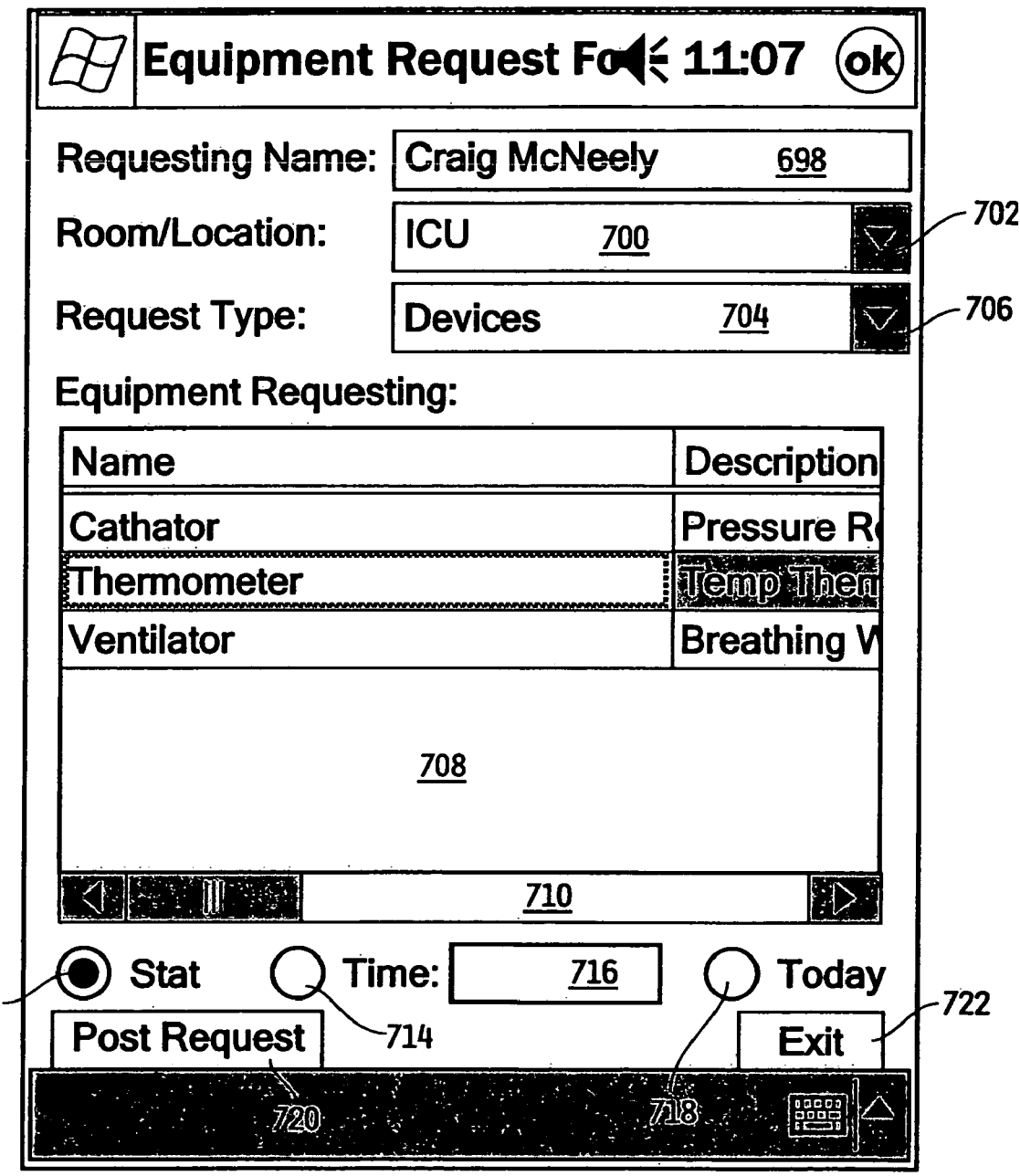

When the user activates equipment request button 614 of screen 604 (FIG. 35), client device 26 responds by generating screen 696 as shown in FIG. 42. Screen 696 includes the requesting name field 698, a room/location field 700 having a drop down button 702, a request type field 704 having a drop down button 706, an equipment requesting area 708 having a scroll bar 710, a stat radio button 712, a time radio button 714, a time field 716, a today radio button 718, a post request button 720, and an exit button 722. If a user desires to request a particular asset, such as a piece of equipment or new bed linens, the user must first populate room/location field 700 and request type field 704 by selecting from options available using drop down buttons 702, 706, respectively. Once the user has selected a desired location and equipment type, client device 26 accesses database 40 via network 16 and server 12 to obtain a listing of all available equipment of the selected type. The listing is displayed in area 708. The user may then highlight a desired asset from those listed in area 708. Next, the user may indicate the urgency of the equipment request or asset request by activating one of radio buttons 712, 714, 718. If time radio button 714 is activated, the user may populate time field 716 with information indicating the desired time of arrival of the requested asset. Finally, the user activates post request button 720 which causes client device 26 to transmit a request for the selected asset to server 12 via network 16. As explained above, the information associated with the asset request may then be available for display on screen 520 of FIG. 32 as an open asset request. Additionally, personnel responsible for delivering assets may be notified by system 10 in any of a variety of ways. For example, such personnel may be called, paged, e-mailed, or otherwise receive notification of an open asset request using system 10. FIG. 43 shows screen 696 configured to post an asset request for an ICU location of a device asset type (specifically, a thermometer) with a stat urgency level.

Figure 44:
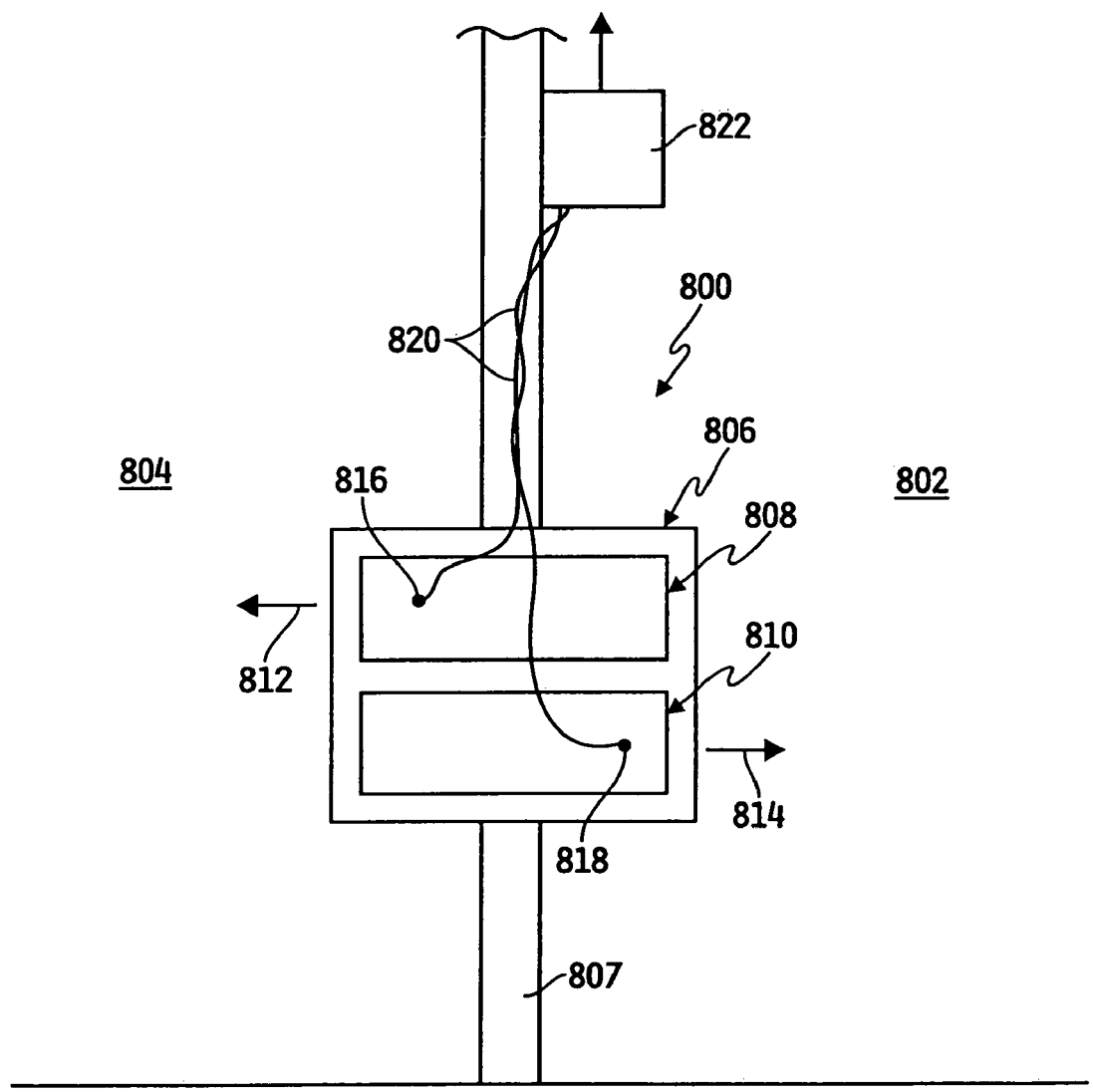
FIG. 44 is a conceptual, side elevational view of a pass through wall component of the system shown in FIGS. 1 and 2.

FIG. 44 depicts another feature of one embodiment of system 10 for monitoring the status and movement of assets within the facility. FIG. 44 depicts a pass through wall 800 for moving assets between area 802 and area 804. Pass through wall 800 may include a housing 806 mounted within a wall 807 supporting a pair of movable drawers 808, 810. It should be understood that in accordance with the principles of the present invention, one or more than two drawers may be used, and such drawers may be arranged in any desired fashion relative to one another in addition to the vertically stacked arrangement shown in FIG. 44. Also, the drawers may be housed separately and spaced apart from one another such that one drawer extends through one wall of a room and another draw extends through another wall of the room. Moreover, the drawers may be of any acceptable configuration or shape. In fact, a simple opening in a wall or barrier may be configured as a pass through wall according to the present invention, with no moving parts.

In the example shown in FIG. 44, drawer 808 is designated for moving assets into area 804 as indicated by arrow 812, and drawer 810 is designated for moving assets out of area 804 as indicated by arrow 814. Mounted adjacent drawer 808 is at least one RFID sensor 816 for reading unique identification numbers stored on RFID tags 24 associated with assets moved from area 802 to area 804 in drawer 808. Similarly, at least one RFID sensor 818 is mounted adjacent drawer 810 for reading unique identification numbers from RFID tags 24 associated with assets moved from area 804 to area 802 in drawer 810. In one embodiment of the invention, a pair of RFID sensors 816 are mounted adjacent drawer 808 (e.g., one on either side of drawer 808). Additionally, a pair of RFID sensors 818 are mounted adjacent drawer 810 in a similar fashion. RFID sensors 816, 818 are connected via conductors 820 (e.g., coax) to an interface module 822. In one embodiment of the invention, RFID sensor 816, 818 are conventional RFID antenna, and interface 822 is a conventional RFID interface that provides power to sensors 816, 818, interprets the signals provided by sensor 816, 818, and provides a serial output to a computing device. In this embodiment, interface 822 may be connected to a personnel computer or workstation 28 coupled to server 12 via network 14. Workstation 28 may be used to configure pass through wall 800 by assigning a location to each of RFID sensors 816, 818 and a direction for the drawers monitored by sensors 816, 818. For example, RFID sensors 816 may be associated with a particular patient's room (area 804) and designated to indicate movement of assets through drawer 808 into area 804. RFID sensors 818 may be also associated with area 804 and designated to indicate movement of assets out of area 804 through drawer 810. As such, when RFID sensors 816 detect an identification number from an RFID tag 24 associated with a particular asset, system 10 can interpret the corresponding signal from interface 822 as indicating the movement of that asset into area 804. Signals detected by RFID sensors 818 may similarly indicate movement of assets out of area 804.

One use of pass through wall 800 includes controlling (in addition to monitoring) the movement of assets into and out of, for example, a patient's room. For example, when assets such as used bed linens are moved out of area 804 into drawer 810, sensors 818 detect the presence of the RFID tag 24 attached to the bed linens, and interface 822 provides a signal to workstation 28 indicating the presence of the bed linens in drawer 810. The software of the present invention is configured to interpret the presence of bed linens in drawer 810 by associating a contaminated status with the bed linens in database 40 of server 12. Facility personnel responsible for collecting contaminated bed linens may be notified in any of the ways described above to collect the bed linens disposed in drawer 810. If the bed linens are taken to a cleaning area to be laundered, transceivers 20 located in the cleaning area may detect the presence of RFID tag 24 associated with the bed linens and transmit the new location information to server 12 in the manner described above. Logic software 38 of server 12 may determine, based upon the presence of the bed linens in a cleaning area, that the status of the bed linens should be changed to "cleaned." As such, the bed linens may be moved into another patient's room or back into area 804 through drawer 808. If, on the other hand, facility personnel attempt to return the bed linens to area 804 prior to cleaning them, sensors 816 will detect the presence of the bed linens in drawer 808 by reading the identification number of the RFID tag 24 associated with the bed linens. Interface 822 will notify workstation 28 and server 12 in the manner described above. Workstation 28 or server 12 may then activate a lock out feature such as a mechanical or electromechanical lock that prevents movement of drawer 808 into area 804. Additionally, an alarm may be sounded or a visual indication of the lock out condition may be provided to alert personnel of an attempt to move a contaminated asset into area 804.

It should be understood that RFID sensors 816, 818 may, like RFID interfaces 30, 42 described above, also include the ability to write information to RFID tags 24. In such an embodiment, RFID sensor 818 could write information to RFID tag 24 associated with the bed linens when the bed linens are placed drawer 810 to indicate in the memory of RFID tag 24 that the bed linen status is "contaminated." As such, even if server 12 is inoperable for some reason, the contaminated status of the bed linens may still be detected by RFID sensors 816, 818 when the bed linens are placed into drawer 808. Accordingly, workstation 28 may initiate a lock out condition as described above without accessing status information stored in database 40 in association with RFID tag 24 attached to the bed linens. Obviously, the movement and status of any of a variety of different types of assets may be monitored and controlled in the manner described above.

The above-described linen example is illustrative of the types of business rules incorporated into logic software 38 of server 12. Any of a variety of types of responses to detected situations may be implemented by system 10. For example, by detecting the movement of a patient from a location such as an operating room (via RFID tag 24 associated with the patient), logic software 38 may automatically cause server 12 to issue messages to appropriate personnel to prepare a recovery room or deliver required equipment to the destination of the patient. If, after a predetermined period of time, server 12 does not receive information from transceivers 18, 20, client devices 26, workstations 28, or otherwise, indicating that the patient is located in an acceptable location, accompanied by appropriate personnel, equipment and supplies, server 12 may again issue messages in the manner described above to personnel responsible for ensuring the appropriate response to movement of the patient out of the operating room. In this manner, system 10 not only monitors heath care situations, but automatically intervenes and corrects inappropriate responses to situations based on predetermined business rules. Moreover, logic software 38 may be configured such that it automatically modifies certain business rules based on data reflecting historical responses to situations using available principles of artificial intelligence.

Another example of activity based responses enabled by system 10 involves the discharge or transfer of a patient. When system 10 detects movement of a patient as described above in conjunction with receipt of a discharge order, for example, from a physician using client device 26, system 10 may automatically respond based on a predetermined protocol. For example, an automatic message may be distributed to a receiving nurse and a receiving charge nurse to indicate that the discharge has initiated. Other personnel copied on the message may include dietary personnel (to avoid misrouting of future meals), pharmacy and IV personnel (to avoid misrouting of equipment and medicine), housekeeping personnel (to permit prompt cleaning of the vacated room), case management personnel, therapy personnel, and other physicians associated with the patient. Family members may further be notified of changes in location or status of patients by automatic posting of information to displays 17 positioned within the facility for viewing by family members, etc. Periodic follow-up messages may automatically be sent if the desired movement of appropriate personnel and/or equipment, or the desired changes in status of the patient or assets are not detected by system 10 in the manner described herein.

It should be understood that interface 822 and workstation 28 may utilize conventional anti-collision technology to enable RFID sensors 816, 818 to simultaneously process signals from a plurality of different RFID tags 24 placed in drawers 808, 810. It should further be understood that pass through wall(s) 800 could be located at a centralized or distributed receiving area for inventory tracking purposes, at a centralized or distributed shipping area to monitor movement out of the facility of materials such as contaminated items, biological samples in containers having RFID tags 24 attached thereto, or other items. Additionally, pass through wall 800 may be used to track and control movement of medications such as initiating an above-described lock out condition if the medication detected by RFID sensors 816 are not associated with, for example, a patient located in area 804 as indicated by data stored in database 40.

Additionally, assets that require preventative maintenance after a certain number of uses may be monitored using pass through wall 800. For example, information reflecting the number of uses of a particular asset may be updated each time the asset is detected as moving into and out of area 804. This updated use information may be stored in database 40, in the memory of RFID tag 24 associated with the asset, or both. When the number of uses exceeds a predetermined threshold indicating the need for preventative maintenance, logic software 38 of server 12 may automatically change the status information associated with the asset in database 40 to "unavailable" and send notification to the appropriate facility personnel responsible for completing the preventative maintenance required. Of course, information describing the use and/or consumption of assets (e.g., IV pumps, medication, etc.) may be provided to server 12 in the manner described above and used for accounting purposes such as billing the patient.

While the invention has been illustrated and described in detail in the drawings and foregoing description, such illustration and description is to be considered as exemplary and not restrictive in character, it being understood that only exemplary embodiments have been shown and described and that all changes and modifications that come within the spirit of the invention and the attached claims are desired to be protected.

What is claimed is:

1. An asset management and communication system for a healthcare facility, including:

a server coupled to a database;

a plurality of tags coupled to a corresponding plurality of assets, each tag being configured to transmit a tag ID that is uniquely associated in the database with asset data describing the corresponding asset;

a first network coupled to the server including a plurality of first transceivers configured to receive the tag IDs and transmit the tag IDs and a transceiver ID to the server via the first network, whereby, in response to receipt of a tag ID and a transceiver ID from a transceiver, the server is configured to update the database with location information for the asset corresponding to the tag ID to indicate that the corresponding asset is adjacent the transceiver;

a second network coupled to the server including a plurality of access points; and a plurality of portable client devices, each client device including a display and a transceiver configured to wirelessly transmit to the server via one of the plurality of access points a client device ID that is uniquely associated in the database with a user of the client device, whereby, in response to receipt of the client device ID, the server is configured to update the database with location information for the user to indicate that the user is within a reception range of the one access point, wherein each portable client device of the plurality of portable client devices is capable of being used to establish voice communications with each of the other portable client devices, wherein each of the portable client devices has a reader configured to read data directly from each of the plurality of tags, wherein each of the portable client devices is configured to control equipment associated with a patient room, and wherein each of the portable client devices are capable of being used to access information that relates to patients and that is stored on the server.

2. The system of claim 1, further including an external network coupled to the server.

3. The system of claim 2, wherein the external network is the internet.

4. The system of claim 1, wherein the database is a distributed database having portions of data stored at a plurality of different physical locations.

5. The system of claim 1, further including a plurality of routers connected to the second network and the server, the routers being configured to process communications between the second network and the server.

6. The system of claim 1, wherein the first plurality of transceivers are mounted at a corresponding plurality of fixed locations within the facility.

7. The system of claim 1, wherein each of the plurality of portable client devices is configured to write information for storage on the plurality of tags.

8. The system of claim 7, wherein each client device responds to information read from a tag via the interface by obtaining from the server asset data associated with the tag.

9. The system of claim 1, wherein each of the plurality of client devices is a thin client device.

10. The system of claim 1, wherein each of the plurality of client devices is configured to communicate with other client devices within a range of the client device without accessing an access point.

11. The system of claim 1, wherein the client device transceivers are configured to transmit and receive text, audio, and video content.

12. The system of claim 1, wherein each of the client devices includes a cellular telephone.

13. The system of claim 1, wherein each of the client devices includes one of the plurality of tags.

14. The system of claim 1, further including a plurality of workstations coupled to the first network.

15. The system of claim 14, wherein one of the workstations includes an interface configured to read information from and write information to any of the plurality of tags.

16. The system of claim 14, wherein each of the workstations includes a local database including a portion of the data stored in the database coupled to the server.

17. The system of claim 1, further including a nurse call server coupled to the server, the nurse call server being configured to respond to input signals from an input device operated by a user by transmitting a request signal to the server, the server being configured to respond to the request signal by transmitting a signal to a particular client device.

18. The system of claim 1, further including a nurse call server coupled to the server, the nurse call server being configured to respond to input signals from an input device operated by a user by changing the status of an indicator.

19. The system of claim 1, further including a monitoring server coupled to the server, the monitoring server being configured to receive output data generated by a piece of equipment and to transmit the output data to the server.

20. The system of claim 1, wherein each of the client devices includes software configured to generate a plurality of screens on the display.

21. The system of claim 20, wherein the display is a touch sensitive display.

22. The system of claim 20, wherein the plurality of screens includes a log on screen having icons for facilitating access to the second network.

23. The system of claim 20, wherein the plurality of screens includes a users screen including a list of users authorized to access the second network.

24. The system of claim 20, wherein one of the plurality of screens includes a call person button, activation of which causes the client device to send a signal to a specified other client device to establish a communications link between the client device and the specified other client device.

25. The system of claim 20, wherein the plurality of screens includes a message screen having a record message button, activation of which causes the client device to record input signals from a microphone coupled to the client device.

26. The system of claim 25, wherein the message screen further includes a send message button, activation of which causes the client device to transmit a signal corresponding to the recorded input signals to a specified other client device.

27. The system of claim 1, wherein the asset data includes historical data describing past locations of the corresponding asset.

28. The system of claim 27, wherein the server is configured to automatically perform a plurality of operations based upon a plurality of predefined rules.

29. The system of claim 28, wherein one of the operations is updating the status of an asset based upon a current location of the asset and a past location of the asset.

30. The system of claim 28, wherein one of the operations is transmitting a signal to a particular client device based upon a current location of the asset and a past location of the asset.

31. The system of claim 28, wherein the asset data includes an access level associated with an asset, the server performing one of the plurality of operations based upon a rule including a determination of the access level of the asset.

32. The system of claim 1, wherein each of the client devices is configured to access the database to determine the location and status of an asset having asset data stored in the database.

33. The system of claim 32, wherein the database further includes a file linked to the asset data of the asset, the file including additional information about the asset.

34. The system of claim 32, wherein each of the client device displays is configured to generate an asset request button, activation of which causes the client device to transmit a request signal to the server, the server responding to the request signal by transmitting a notification to a person responsible for delivering requested assets.

35. The system of claim 34, wherein the each of the client device displays is further configured to receive a user-selected designation of an urgency level of a request.

36. An asset management and communications system for a healthcare facility, including: a server coupled to a database;
a plurality of tags associated with a corresponding plurality of assets, each tag having a unique ID;
a plurality of sensors, each sensor configured to read the tag IDs of tags adjacent the sensor and to transmit a signal to the server indicating that the tags are adjacent the sensor, thereby permitting the server to update the database with location information indicating that the tags are adjacent a known location of the sensor; and
a plurality of portable client devices coupled to the server via access points positioned at known locations within the facility, each client device including a transceiver configured to transmit a unique ID signal to the server via an access point, thereby permitting the server to update the database with location information indicating that the client device is within a reception range of the access point;
the client device transceivers being further configured to access the tag location information in the database, wherein each portable client device of the plurality of portable client devices is capable of being used to establish voice communications with each of the other portable client devices, wherein each of the portable client devices has a reader configured to read data directly from each of the plurality of tags, wherein each of the portable client devices is configured to control equipment associated with a patient room, and wherein each of the portable client devices are capable of being used to access information that relates to patients and that is stored on the server.

* * * * *